(12) United States Patent
Markowitz et al.

(10) Patent No.: US 8,642,271 B2
(45) Date of Patent: Feb. 4, 2014

(54) ABERRANT METHYLATION OF C6ORF150 DNA SEQUENCES IN HUMAN COLORECTAL CANCER

(75) Inventors: Sanford D. Markowitz, Pepper Pike, OH (US); Helen Moinova, Beachwood, OH (US); Lois Myeroff, Chardon, OH (US); Jean-Pierre Issa, Bellaire, TX (US); Osamu Maeda, Nagoya (JP)

(73) Assignees: Case Western Reserve University, Cleveland, OH (US); Board of Regents, The University of Texas System, Austin, TX (US)

( * ) Notice: Subject to any disclaimer, the term of this patent is extended or adjusted under 35 U.S.C. 154(b) by 368 days.

(21) Appl. No.: 12/870,674

(22) Filed: Aug. 27, 2010

(65) Prior Publication Data

US 2011/0165567 A1    Jul. 7, 2011

Related U.S. Application Data

(60) Provisional application No. 61/275,355, filed on Aug. 27, 2009.

(51) Int. Cl.
*C12Q 1/68* (2006.01)
*G01N 33/53* (2006.01)

(52) U.S. Cl.
USPC .................. 435/6.14; 435/6.12; 435/7.1

(58) Field of Classification Search
None
See application file for complete search history.

(56) References Cited

U.S. PATENT DOCUMENTS

| | | | |
|---|---|---|---|
| 5,786,146 A | 7/1998 | Herman et al. | |
| 6,017,704 A | 1/2000 | Herman et al. | |
| 6,200,756 B1 | 3/2001 | Herman et al. | |
| 6,265,171 B1 | 7/2001 | Herman et al. | |
| 6,858,388 B2 | 2/2005 | Markowitz et al. | |
| 7,485,420 B2 | 2/2009 | Markowitz | |
| 2008/0075722 A1* | 3/2008 | DePinho et al. | 424/138.1 |
| 2008/0085867 A1* | 4/2008 | Baylin et al. | 514/44 |
| 2008/0172183 A1* | 7/2008 | Karger et al. | 702/19 |
| 2008/0188428 A1* | 8/2008 | Bentwich | 514/44 |
| 2009/0155180 A1 | 6/2009 | Jump et al. | |
| 2011/0144076 A1 | 6/2011 | Williams et al. | |
| 2011/0229479 A1 | 9/2011 | Vogelstein et al. | |

OTHER PUBLICATIONS

Abd El-Aziz et al., "Large-scale Molecular Analysis of a 34 Mb Interval on Chromosome 6q: Major Refinement of the RP25 Interval," Annals of Human Genetics, vol. 72: 463-477 (2008).

Estécio et al., "High-throughput methylation profiling by MCA coupled to CpG island microarray," Genome Research, vol. 17: 1529-1536 (2007).

Gonzalgo and Jones, "Rapid quantitation of methylation differences at specific sites using methylation-sensitive single nucleotide primer extension (MS-SNuPE)," Nucleic Acids Research, vol. 25(12): 2529-2531 (1997).

Herman et al., "Methylation-specific PCR: A novel PCR assay for methylation status of CpG islands," Proc. Natl. Acad. Sci., vol. 93: 9821-9826 (1996).

Kane et al. "Methylation of the *hMLH1* Promoter Correlates with Lack of Expression of hMLH1 in Sporadic Colon Tumors and Mismatch Repair-defective Human Tumor Cell Lines," Cancer Research, vol. 57: 808-811 (1997).

Shen et al., "Genome-Wide Profiling of DNA Methylation Reveals a Class of Normally Methylation CpG Island Promoters," PLo5 Genetics, vol. 3(10): 2023-2036 (2007).

Xiong and Laird, "COBRA: a sensitive and quantitative DNA methylation assay," Nucleic Acids Research, vol. 25(12): 2532-2534 (1997).

\* cited by examiner

*Primary Examiner* — James Martinell
(74) *Attorney, Agent, or Firm* — Ropes & Gray LLP

(57) ABSTRACT

This application describes methods and compositions for detecting and treating C6Orf150-associated neoplasia. Differential methylation of the C6Orf150 nucleotide sequences has been observed in C6Orf150-associated neoplasia such as colon neoplasia.

24 Claims, 18 Drawing Sheets
(15 of 18 Drawing Sheet(s) Filed in Color)

Figure 6    MS-PCR condition for C6orf150-MSP8 (methylated)

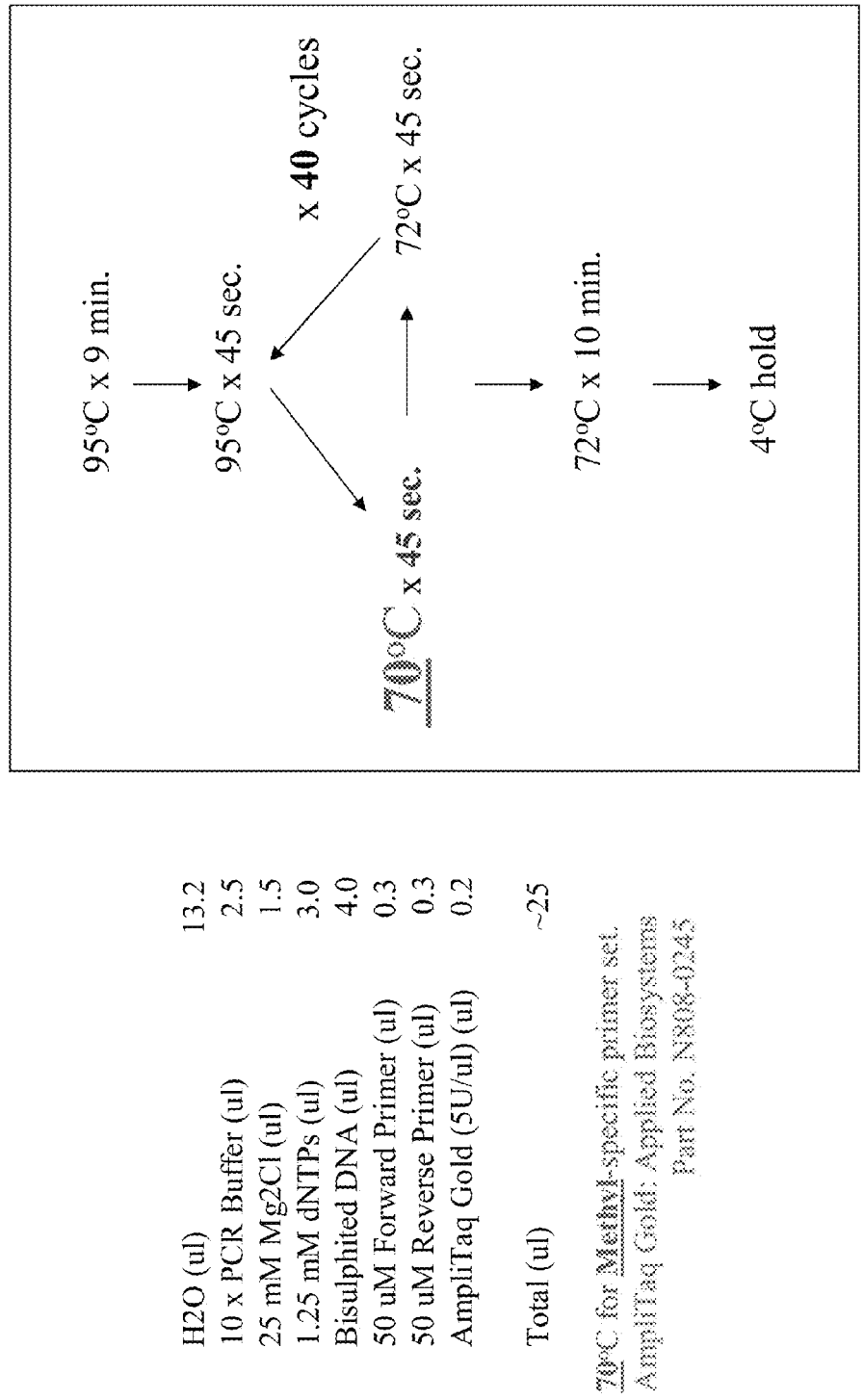

| | |
|---|---|
| H2O (ul) | 13.2 |
| 10 x PCR Buffer (ul) | 2.5 |
| 25 mM Mg2Cl (ul) | 1.5 |
| 1.25 mM dNTPs (ul) | 3.0 |
| Bisulphited DNA (ul) | 4.0 |
| 50 uM Forward Primer (ul) | 0.3 |
| 50 uM Reverse Primer (ul) | 0.3 |
| AmpliTaq Gold (5U/ul) (ul) | 0.2 |
| Total (ul) | ~25 |

70°C for Methyl-specific primer set.
AmpliTaq Gold: Applied Biosystems
Part No. N808-0245 c6orf150-MSP8 Methyl-specific primer set:
5c6-1200FM: 5'-GAGTTTCGGTTGTTTTCGAGGTCGT -3'
37c6-1329RM: 5'-CCCCAATTACGCGAACGAACGA-3'

Figure 11

C6orf150 MS-PCR summary on Exon array samples

| | Total | c6orf150 methylated (MSP8) | Percent |
|---|---|---|---|
| cell lines-test set | 34 | 14 | 41% |
| Non-cancer normals | 13 | 0 | 0% |
| Cancer normals (including crypts) | 16 | 0 | 0% |
| Validation Set — xenografts | 33 | 11 | 33% |
| Validation Set — Dukes Bs | 35 | 9 | 26% |
| Validation Set — Dukes C | 23 | 4 | 17% |
| Validation Set — Dukes' D | 30 | 9 | 30% |
| Validation Set — mets | 33 | 8 | 24% |
| Totals for validation set | 154 | 41 | 27% |

Figure 14A

SEQ ID NO: 1

Figure 14B

CCGTAACAGGGCAGTGTTTGATGGTGTGGACCTGAGGTCCGAGTCAGATCAGAGAAAAAGAGATCTCAGTTCTTCTTTTCTTTTTTTTGAAGATAATTGAATATTGAAGTGGTCTGTCTCCTG
TTCCACGTAGACTTCTCATGGAGGAAGACCTCATAAGAAAAAGAGATCTCAGTTCTTCTTTTCTTTTTTTTGAGGCGGAG
CCCCTCTCTGCTATCCGTGACTGCCCCAGTGGAGTGCTGGAGTCGGCAGTAGCTCGAAGCTCCGGCTATCCGGCTCGCAAGCTCCGGTTCAGCCATTCCCT
TCTCGCTGCGTCCCCAGTCAGCTAGTGCTGGGATTACAGGCGCCCGGCCACCATGCCCGGCCACCCGGTCAGCCATTCCCT
GCCTCAGCTTCCCGAGTAGCTGGGATTACAGGCGCCCGGCCACCATGCCCGGCCACCTGGTTAGTAGAGACGGGTG
TTCACCGTGTTAGCCAGGATGGTCTCGATCTCTGACCTCGTGATCCGCCCAGTTCTCACAGATACACATTCGTATAATTCGTGTATATTACAGTCCATTT
TSAGCTACCCGCGCCGGCCTCGTCCCCAGTTCTCACAGATACACATTCGTATAATTCGTGTATATTACAGCTCCATTT
AGAATATCCTACAGATACTAAAGCTTCATTCCCTGTAGTATAATTGAAGAGCAGTTCCTGACGTGTCTTGTACCAGGC
AGCAGAGATTGTTCTTTTCTTTTCTTCACCTCAACCCTGGCTAATTTTGTATTTTAGTAGAGACGGGTTTCACCATGTTGGCTCAGGCTGGTCT
TGGAGTGCAATGCAGAGCATGAGCTCCCGACCTCAGGTGATCCAGCCTGCCTCGGCCTCCCAAAGTGCTGGGATTACAGGCGTAGCCACCAGCCTGGCC
AGAGACTCCCACTCTCTCTCTCTCTCTCTCTCTTATTCTCTCCCAGTCAGCCTTCAAGCGATTCTCCAGCTGTCTCCAGGCTAGT
CTCTCTATTTTGTCTTTCTTTCTTTCTCTCTCACTCAAGTTCAGTCGATTCTCCAGCTGTCTCCAGGCTAGT
GCAATGGTGCCATCTAGGTTTGCTCCCCACTCCGGCTAATTTTTATGTATTTTTAGTAGAGACGGGGCTTCACCATGTTGGCCAGGCTGGTCTCGA
TTACAGGTGCCTGGCCACCAGGATCCACTCCGGCTAATTTTTATGTATTTTTAGTAGAGACGGGGCTTCACCATGTTGGCCAGGCTGGTCTCGA
ACTCTGAGCATGAGTCATTTTTAATTACTAATTACTTTTCAGCATCAGATATGTCTCTGATTGAAGCATGAAGCATTGATT
GTCTTGAGCATGAGTCAGTTTTAATTACTAATTACTTTTCAGCATCAGATATGTCTCTGATTGAAGCATGAAGCATTGATT
GTATCAATTCAGTGCATTCAGAACCACTTTGTTGTGTCTCACTGCAAGCCCTAATTTTGTATTTTTAGTAGAGACAGTCCACTCTTGTCACC
AGGCTGGGACTACAGGCGCCCACCACCACGGCCTATCTCGGCTATCCCCAGCCTAATTTTGTATTTTTAGTAGAGACAGTCCACTCTTGTCACC
GTAGCTGGGACTACAGGCGTAGGCCACCACCACGGCCCCAGCCTAATTTTGTATTTTTAGTAGAGACGGGGTTTCACCGTGTTAGCCAGG
CTGGT

SEQ ID NO: 1 (con't)

Figure 15A

SEQ ID NO: 4

Figure 15B

SEQ ID NO: 4 (con't)

ABERRANT METHYLATION OF C6ORF150 DNA SEQUENCES IN HUMAN COLORECTAL CANCER

RELATED APPLICATIONS

This application claims the benefit of priority to U.S. provisional application No. 61/275,355, filed Aug. 27, 2009, the disclosure of which is hereby incorporated by reference in its entirety.

FUNDING

Work described herein was supported by National Institutes of Health Grant R01CA 120237, U54 CA 116867, and CA98006. The United States Government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 3, 2010, is named CWRU0921.txt and is 72,424 bytes in size.

BACKGROUND

Colorectal cancer is among the leading causes of cancer-related morbidity and mortality in industrialized nations. The pathogenesis is related to hereditary influences, modified by the quantity and quality of dietary fat. In 1995, the American Cancer society estimated that 135,000 new cases of colon cancer were diagnosed; 71% were in the colon and 30% were in the rectum. Patients diagnosed at an early stage, prior to lymph-node spread, are potentially cured with surgery. Approximately 40% of patients are diagnosed at an early stage. The remaining cases frequently undergo peri-operative radiation and/or chemotherapy to attempt to control the metastatic spread of disease. Ultimately, 50% of patients thought to have undergone curative resections eventually develop recurrent disease. Unfortunately, 55,000 Americans die each year due to recurrent or metastatic colon or rectal cancer. The key to enhanced survival is early diagnosis. Colon and rectal cancers are often silent and slowly progressive. Most patients exhibit symptoms such as rectal bleeding, pain, abdominal distension or weight loss only after the disease is advanced and not surgically curable.

Early detection depends upon availability of high-quality methods. Such methods are also useful for determining patient prognosis, selecting therapy, monitoring response to therapy and selecting patients for additional therapy. Although methods for detecting colon cancer exist, the methods are not ideal. Digital rectal exams (i.e., manual probing of rectum by a physician), for example, although relatively inexpensive, are unpleasant and can be inaccurate. Fecal occult blood testing (i.e., detection of blood in stool) is nonspecific because blood in the stool has multiple causes. Colonoscopy and sigmoidoscopy (i.e., direct examination of the colon with a flexible viewing instrument) are both uncomfortable for the patient and expensive. Double-contrast barium enema (i.e., taking X-rays of barium-filled colon) is also an expensive procedure, usually performed by a radiologist. Consequently, there is a need for cancer diagnostic methods that are specific, accurate, minimally invasive, technically simple and inexpensive.

Because of the disadvantages of existing methods for detecting or treating cancers, new methods are needed for cancer diagnosis and therapy.

SUMMARY OF THE INVENTION

The present invention is based in part on Applicants' discovery of a particular human genomic DNA region, starting within and extending beyond the C6Orf150 genomic locus (NM_138441.2) that spans coordinates chr6:74191577-74218764 in the (hg18) assembly of the UCSC Genome Browser), in which the cytosines within CpG dinucleotides are differentially methylated in tissues from human cancers (e.g., colon cancer) and unmethylated in normal human tissues. The genomic sequence is disclosed herein as SEQ ID NO: 1, corresponding to (hg18) coordinates 74,219,719-74,215,720. The present methods are also based, in part, on Applicants' discovery that the levels of C6Orf150 transcript in tissues from human cancers are lower than the levels of C6Orf150 transcript in normal tissues.

In one aspect, the invention provides a method for detecting the likelihood that a human patient has a gastrointestinal neoplasia, comprising obtaining a human sample; and assaying said sample for the presence or absence of methylation within a nucleotide sequence set forth in SEQ ID NO: 1 or its reverse complement sequence set forth in SEQ ID NO: 4, or fragments thereof, wherein the presence of methylation within any one of said nucleotide sequence is indicative of the likelihood that the human patient has colon neoplasia. In certain embodiments, the fragment contains at least one site of methylation, and is of a length amenable to MS-PCR and/or digestion by methylation-sensitive restriction enzyme. In some embodiments, the method comprises assaying for the presence or absence of methylation of the C6Orf150 gene sequence selected from SEQ ID NOs: 7 or 10. In other embodiments, the method comprises assaying for the presence or absence of methylation of the C6Orf150 sequence selected from SEQ ID NOs: 13 or 16.

In another aspect, the invention provides a method for detecting the likelihood that a human patient has a gastrointestinal neoplasia, comprising obtaining a human sample; and assaying said sample for the presence or absence of methylation within a nucleotide sequence set forth in SEQ ID NO: 7 or its reverse complement sequence set forth in SEQ ID NO: 10, or fragments thereof, wherein the presence of methylation within any one of said nucleotide sequence is indicative of the likelihood that the human patient has colon neoplasia. In certain embodiments, the fragment contains at least one site of methylation, and is of a length amenable to MS-PCR and/or digestion by methylation-sensitive restriction enzyme.

In yet other aspects, the invention provides a method for detecting the likelihood that a human patient has a gastrointestinal neoplasia, comprising obtaining a human sample; and assaying said sample for the presence or absence of methylation within a nucleotide sequence set forth in SEQ ID NO: 13 or its reverse complement sequence set forth in SEQ ID NO:16, or fragments thereof, wherein the presence of methylation within any one of said nucleotide sequence is indicative of the likelihood that the human patient has colon neoplasia. In certain embodiments, the fragment contains at least one site of methylation, and is of a length amenable to MS-PCR and/or digestion by methylation-sensitive restriction enzyme.

In any of the foregoing aspects, the gastrointestinal neoplasia is a colon neoplasia, e.g., colon cancer, colon adenoma, and other colonic neoplasia types. In some embodiments, the sample is a bodily fluid selected from blood, serum, plasma, a blood-derived fraction, stool, urine, and a colonic effluent. In other embodiments, the bodily fluid is obtained from a subject suspected of having or is known to have colon neoplasia.

In any of the foregoing aspects, the assay can be methylation-specific PCR. The method may comprise treating DNA from the sample with a compound that converts non-methylated cytosine bases in the DNA to a different base; amplifying a region of the compound converted C6Orf150 nucleotide sequence with a forward primer and a reverse primer; and analyzing the methylation patterns of said C6Orf150 nucleotide sequences. In some embodiments, the method may comprise treating DNA from the sample with a compound that converts non-methylated cytosine bases in the DNA to a different base; amplifying a region of the compound converted C6Orf150 nucleotide sequence with a forward primer and a reverse primer; and detecting the presence and/or amount of the amplified product. In one embodiment, the compound used to treat DNA is a bisulfite compound.

In a related embodiment, the method comprises forward primers selected from SEQ ID NOs: 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137. In other embodiments, the method comprises reverse primers selected from SEQ ID NOs: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, and 138. In certain embodiments, the method comprises PCR primer pairs selected from MSPS, MSP10, and MSP23.

In any of the foregoing methods, the method comprises assaying using a methylation-specific restriction enzyme. In some embodiments, the methylation-specific restriction enzyme is selected from HpaII, SmaI, SacII, EagI, MspI, BstUI, and BssHII. In certain embodiments, the method comprises a pair of primers selected from SEQ ID NOs: 139, 140, 141, 142, 143, 144, 145, and 146.

In another aspect, the present invention provides a method for detecting the likelihood that a human subject has colon neoplasia, comprising detecting C6Orf150 protein or nucleic acid expression level in a sample from the human subject, wherein reduced expression level of C6Orf150 protein or nucleic acid relative to a control sample from a healthy subject is indicative of the likelihood that the human subject has colon neoplasia. In certain embodiments, the sample is a bodily fluid selected from blood, serum, plasma, a blood-derived fraction, stool, urine, and a colonic effluent. In one embodiment, the bodily fluid is from a subject suspected of having or known to have colon neoplasia. In some embodiments, the C6Orf150 protein is detected by an immunoassay.

In other aspects, the present invention provides a method for identifying an agent which enhances C6Orf150 protein or nucleic acid expression in a diseased cell associated with C6orf150 gene silencing, comprising contacting the cell with a sufficient amount of the agent under suitable conditions; quantitatively determining the amount of C6Orf150 protein or nucleic acid; and comparing the amount of C6Orf150 protein or nucleic acid with the amount of C6Orf150 protein or nucleic acid in the absence of the agent, wherein a greater amount of C6Orf150 protein or nucleic acid in the presence of the agent than in the absence of the agent indicates that the agent enhances C6Orf150 protein or nucleic acid expression. In one embodiment said C6Orf150 gene silencing is due to differential methylation of a C6Orf150 nucleotide sequence.

In a related embodiment, differential methylation occurs within a C6Orf150 nucleotide sequence set forth in SEQ ID NO: 7, or fragments thereof. In certain embodiments, the fragment contains at least one site of methylation, and is of a length amenable to MS-PCR and/or digestion by methylation-sensitive restriction enzyme. In some embodiments, the diseased cell is from a subject having colon neoplasia.

In another aspect, the present invention also provides a method for monitoring over time colon neoplasia in a human subject, comprising (a) detecting the methylation status of a C6Orf150 nucleotide sequence selected from SEQ ID NOs: 1, 4, 7, 10, 13, and 16 in a sample from the human subject for a first time; and (b) detecting the methylation status of any one of said C6Orf150 nucleotide sequence of step (a) in a sample from the same human subject at a later time; wherein absence of methylation in the C6Orf150 nucleotide sequence taken at a later time and presence of methylation in the C6Orf150 nucleotide sequence taken at the first time is indicative of regression of colon neoplasia; wherein presence of methylation in the C6Orf150 nucleotide sequence taken at a later time and absence of methylation in the C6Orf150 nucleotide sequence taken at the first time is indicative of progression of colon neoplasia. In a related embodiment, the sample is a bodily fluid selected from the group consisting of blood, serum, plasma, a blood-derived fraction, stool, urine, and a colonic effluent.

In other aspects, the present invention also provides oligonucleotide primer for detecting methylation of a C6Orf150 nucleotide sequence, selected from SEQ ID NOs: 19-138. In certain aspects, the present invention also provides oligonucleotide primer for detecting methylation of a C6Orf150 nucleotide sequence, selected from SEQ ID NOs: 139-146.

In other aspects, the present invention provides a method for detecting colon cancer, comprising obtaining a sample from a patient; and assaying said sample for the presence of methylation of nucleotide sequences within at least two genes selected from: C6Orf150, vimentin, SLC5A8, HLTF, p16, and hMLH1; wherein methylation of nucleotide sequences within any of the genes is indicative of colon cancer. In a related embodiment, the sample is a bodily fluid selected from blood, serum, plasma, a blood-derived fraction, stool, urine, and a colonic effluent. In some embodiments, the bodily fluid is obtained from a subject suspected of having or is known to have colon cancer.

In certain aspects, the present invention provides a method for detecting the likelihood that a patient has colon neoplasia, comprising obtaining a sample from a patient; and assaying said sample for the presence or absence of methylation within a nucleotide sequence set forth in SEQ ID NO: 13 or its reverse complement sequence set forth in SEQ ID NO: 16, wherein the presence of methylation within said nucleotide sequence is indicative of the likelihood that the patient has colon neoplasia. In a related embodiment, the sample is a bodily fluid selected from blood, serum, plasma, a blood-derived fraction, stool, urine, and a colonic effluent. In some embodiments, said colon neoplasia is colon cancer. In other embodiments, the assay is methylation-specific PCR.

In one embodiment, the foregoing method comprises treating DNA from the sample with a compound that converts non-methylated cytosine bases in the DNA to a different base; amplifying a region of the compound converted C6Orf150 nucleotide sequence with a forward primer and a reverse primer; and analyzing the methylation patterns of said C6Orf150 nucleotide sequences. In other embodiments, the method comprises treating DNA from the sample with a compound that converts non-methylated cytosine bases in the DNA to a different base; amplifying a region of the compound converted C6Orf150 nucleotide sequence with a forward primer and a reverse primer; and detecting the presence and/or amount of the amplified product.

In any of the foregoing methods, the compound used to treat DNA is a bisulfite compound.

In certain aspects, the present invention provides isolated or recombinant C6Orf150 nucleotide sequences that are at least 80%, 85%, 90%, 95%, 98%, 99% or identical to the nucleotide sequence of any one of SEQ ID NOs: 1-18, and fragments of said sequences that are 10, 15, 20, 25, 50, 100, or 150 base pairs in length wherein the C6Orf150 nucleotide sequences are differentially methylated in a C6Orf150-associated disease cell.

In another aspect, the present invention provides a kit for detecting a C6Orf150-associated neoplasia in a subject, comprising at least two primers, wherein each of the primers has a sequence selected from the group consisting of SEQ ID NOs: 19-138, for assessing methylation of the human C6Orf150 gene. In some embodiments, the kit further comprises a compound, e.g., bisulfite, to convert a template DNA. In other embodiments, each primer comprises at least a CpG dinucleotide.

In a related embodiment, the kit comprises a forward primer selected from SEQ ID NOs: 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137; and a reverse primer selected from SEQ ID NOs: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, and 138.

In one embodiment, kit comprises a forward primer selected from SEQ ID NOs: 31, 35, and 61, and a reverse primer selected from SEQ ID NOs: 32, 36, and 62.

In one aspect of the invention, provided herein is an oligonucleotide primer for assessing methylation in the human C6Orf150 gene, wherein said primer specifically hybridizes under high stringent conditions to a bisulfite-converted template sequence selected from SEQ ID NOs: 2, 3, 5, 6, and complements thereof.

In another aspect, the present invention provides an oligonucleotide primer for assessing methylation in the human C6Orf150 gene, wherein said primer specifically hybridizes under high stringent conditions to a bisulfite-converted template sequence selected from SEQ ID NOs: 8, 9, 11, 12, 14, 15, 17, 18, and complements thereof.

In any of the foregoing aspects, the primer has a sequence selected from SEQ ID NOs: 19-138. In certain embodiments, said primer is a forward primer selected from SEQ ID NOs: 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137. In other embodiments, said primer is a reverse primer selected from SEQ ID NOs: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, and 138.

In a related embodiment, said primer is further labeled with a detectable marker, e.g., a fluorescent dye.

The present invention also provides a method of inhibiting or reducing growth of cancer cells (e.g., colon cancer). The method comprises increasing the levels of the C6Orf150 protein in cancer cells. In one embodiment, the cells are contacted with the C6Orf150 protein or a biologically active equivalent or fragment thereof under conditions permitting uptake of the protein or fragment. In another embodiment, the cells are contacted with a nucleic acid encoding the C6Orf150 protein and comprising a promoter active in the cancer cell, wherein the promoter is operably linked to the region encoding the C6Orf150 protein, under conditions permitting the uptake of the nucleic acid by the cancer cell. In another embodiment, the method comprises demethylating the methylated C6Orf150 DNA, or otherwise reactivating the silenced C6Orf150 promoter.

The invention contemplates combinations of any of the foregoing or following aspects and embodiments of the invention.

BRIEF DESCRIPTION OF THE DRAWINGS

The patent or application file contains at least one drawing executed in color. Copies of this patent or patent application publication with color drawing(s) will be provided by the Patent Office upon request and payment of the necessary fee.

FIG. 6. A representative MSP amplification condition for MSP8. FIG. 6 discloses the "primer set" sequences as SEQ ID NOS 31-32, respectively, in order of appearance.

FIG. 11. Summary of results for C6Orf150 MSP8 testing of a panel of colon cancer cell lines used in the initial array study, and a panel of normal mucosa from 13 individuals without cancer (non-cancer normals), plus a validation set of 154 colon cancer tumor tissues of known Dukes clinical stage and colon cancer xenografts, and normal colon mucosa from 16 individuals with colon cancer.

FIGS. 14A and 14B. Schematic of SEQ ID NO: 1. The yellow highlighted region corresponds to the C6Orf150 Differentially Methylated Region (DMR). The black, bolded and underlined bases correspond to the locations of outer flanking primers used to amplify the differentially methylated domain following bisulfite conversion of unmethylated cytosine bases to uracil. The red, bolded and underlined bases correspond to the locations of primers that amplify up the MSP-8 target region domain following bisulfite conversion.

FIGS. 15A and 15B. Schematic of SEQ ID NO: 4, the antisense strand of SEQ ID NO: 1. The yellow highlighted region corresponds to the C6Orf150 Differentially Methylated Region (DMR). The black, bolded and underlined bases correspond to the locations of outer flanking primers used to amplify the differentially methylated region following bisulfite conversion of unmethylated cytosine bases to uracil. The red, bolded and underlined bases correspond to the locations of primers that amplify up the MSP-8 target region domain following bisulfite conversion.

DETAILED DESCRIPTION OF THE INVENTION

I. Definitions

Figure 1:
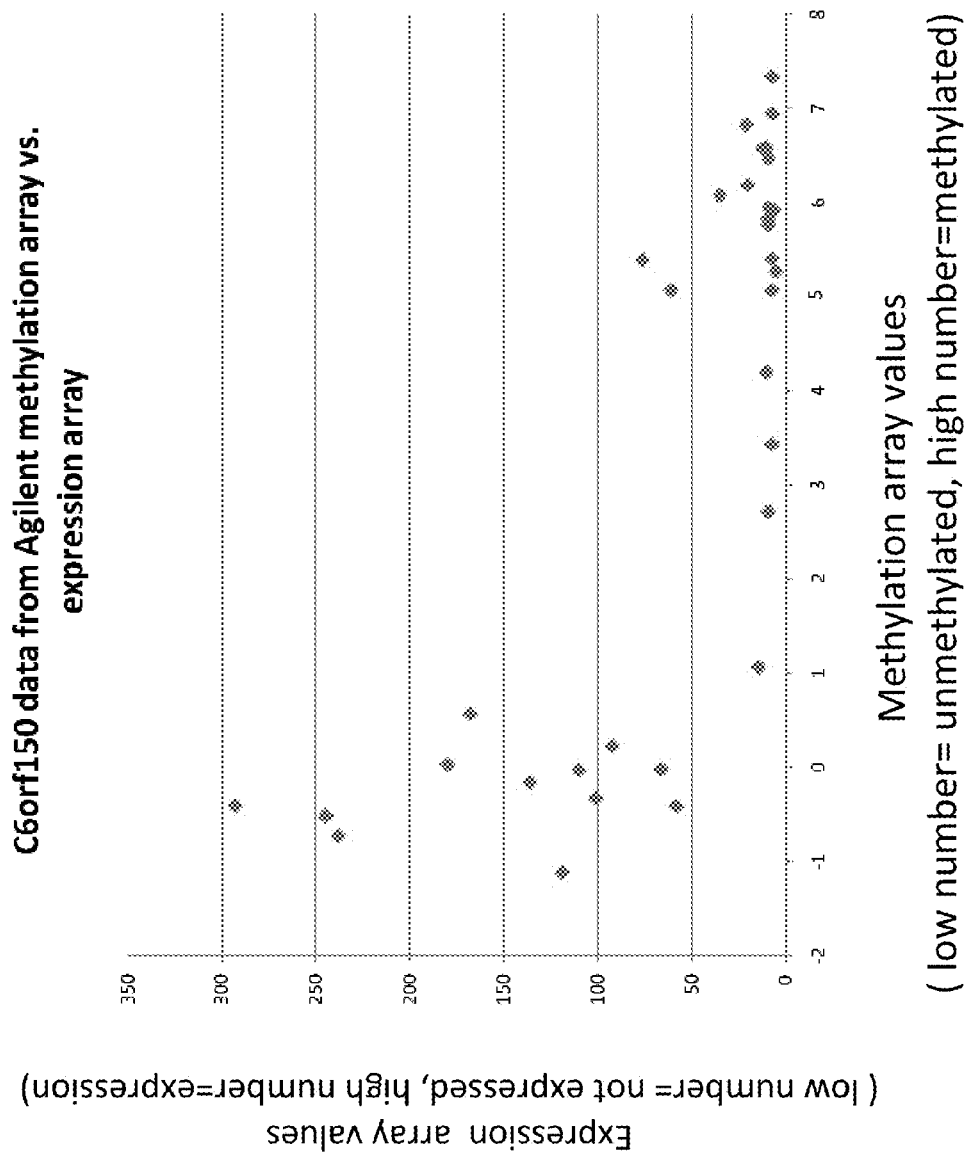
FIG. 1. Data on expression of C6Orf150 transcript as measured on Affymetrix Human Exon 1.0 ST Arrays (Y-axis) for colon cancer cell line samples plotted against log 2 of the MCA methylation values for these samples measured on the Agilent CpG island microarrays (X-axis). Samples with increased levels of C6Orf150 methylation show markedly reduced levels of C6Orf150 transcript expression.
Figure 2:
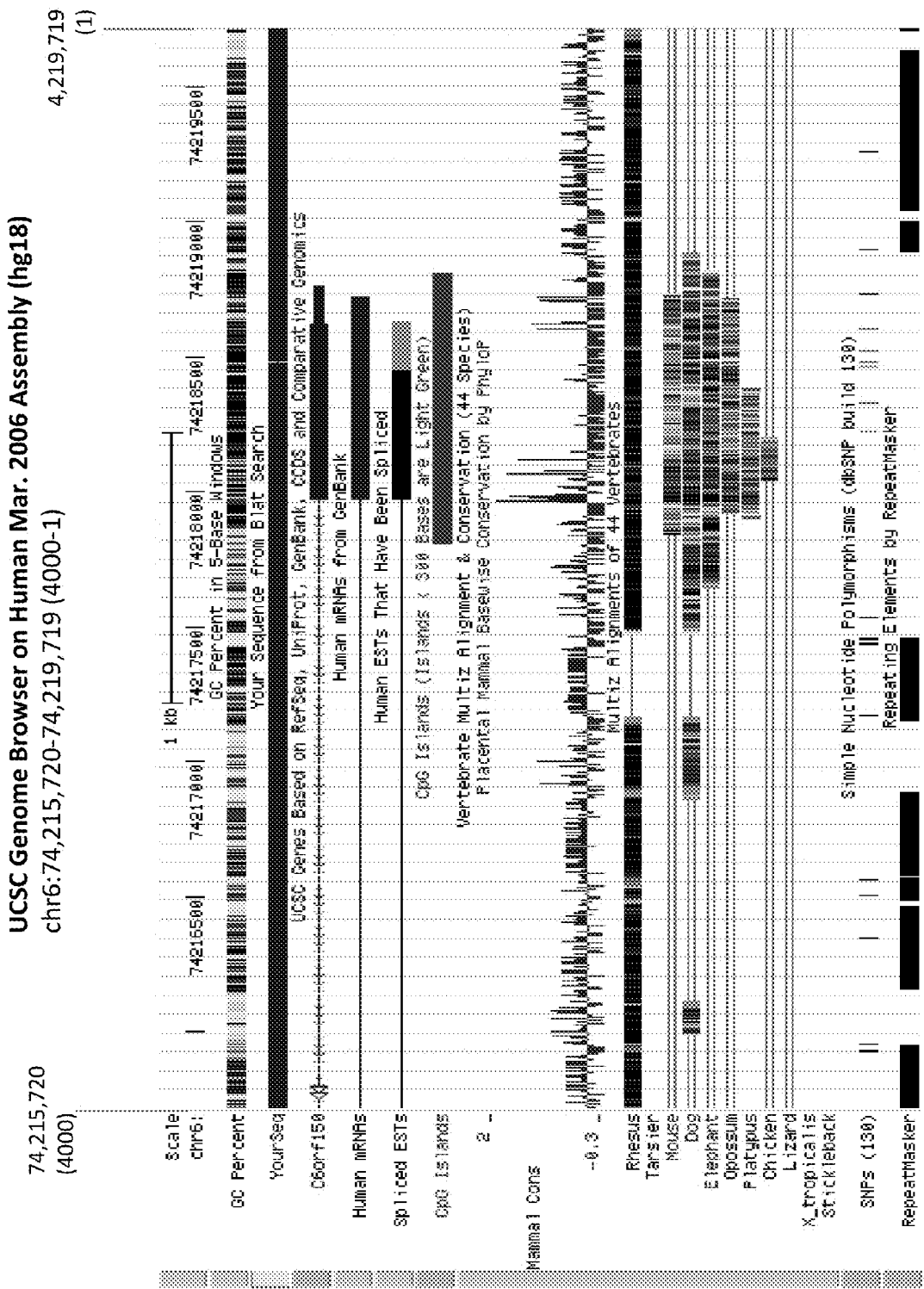
FIG. 2. Screen shot of the UCSC gene browser (hg18 assembly) identifying a CpG island in the C6Orf160 locus region. The sense strand of C6Orf150 lies on the (−) genomic strand of chromosome 6. A 4 kb region aligned to the C6Orf150 sense strand is defined, with coordinates 1-4000 corresponding to (hg18) coordinates 74,219,719-74,215,720.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "adenoma", "colon adenoma," and "polyp" are used herein to describe any precancerous neoplasia of the colon.

The term "colon" as used herein is intended to encompass the right colon (including the cecum), the transverse colon, the left colon, and the rectum.

The terms "colorectal cancer" and "colon cancer" are used interchangeably herein to refer to any cancerous neoplasia of the colon (including the rectum, as defined above).

The term "blood-derived fraction" herein refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "compound", "test compound," "agent", and "molecule" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term "compound-converted DNA" herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term "de-methylating agent" as used herein refers to agents that restore activity and/or gene expression of target genes silenced by methylation upon treatment with the agent. Examples of such agents include, without limitation, 5-azacytidine and 5-aza-2'-deoxycytidine.

As used herein, the phrase "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The term "detection" is used herein to refer to any process of observing a marker, or a change in a marker (such as for example the change in the methylation state of the marker), in a biological sample, whether or not the marker or the change in the marker is actually detected. In other words, the act of probing a sample for a marker or a change in the marker, is a "detection" even if the marker is determined to be not present or below the level of sensitivity. Detection may be a quantitative, semi-quantitative or non-quantitative observation.

The term "differentially methylated region" refers to a region of the C6Orf150 nucleotide sequence that is found to be methylated in a C6Orf150-associated neoplasia such as a region of the C6Orf150 nucleotide sequence that is found to be methylated in colon cancer tissues or cell lines, but not methylated in the normal tissues or cell lines. For example, SEQ ID NO: 7 provides a C6Orf150 region spanning 1060 base pairs that is differentially methylated, referred to herein as the Differentially Methylated Region (DMR). This region corresponds to the minus strand of chromosome 6 base pairs 74,217,783-74,218,842 (UCSC Genome Browser on Human March 2006 Assembly hg18). In certain embodiments, a subset of the DMR, depicted as SEQ ID NO: 13 also represents a differentially methylated region ("MSP8" region). This 130 base pair region corresponds to the minus strand of chromosome 6 base pair 74,218,391-74,218,520 (UCSC Genome Browser on Human March 2006 Assembly hg18).

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a C6Orf150 protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

The terms "healthy", "normal," and "non-neoplastic" are used interchangeably herein to refer to a subject or particular cell or tissue that is devoid (at least to the limit of detection) of a disease condition, such as a neoplasia, that is associated with C6Orf150 such as for example neoplasia associated with silencing of C6Orf150 gene expression due to methylation. These terms are often used herein in reference to tissues and cells of the colon. Thus, for the purposes of this application, a patient with severe heart disease, but lacking a C6Orf150 silencing-associated disease would be termed "healthy."

"C6Orf150-associated neoplasia" refers to neoplasia associated with reduced expression or no expression of the C6Orf150 gene, or reduced levels or undetectable levels of the C6Orf150 transcript. Examples of C6Orf150-associated neoplasia include gastro-intestinal neoplasia and colon neoplasia, etc. Further examples of C6Orf150-associated conditions include non-colonic neoplasias, particularly for early detection of other non-colonic gastrointestinal neoplasias, e.g., neoplasias of the stomach, esophagus and pancreas.

"C6Orf150-associated proliferative disorder" refers to a disease that is associated with either reduced expression or over-expression of the C6Orf150 gene.

Figure 3:
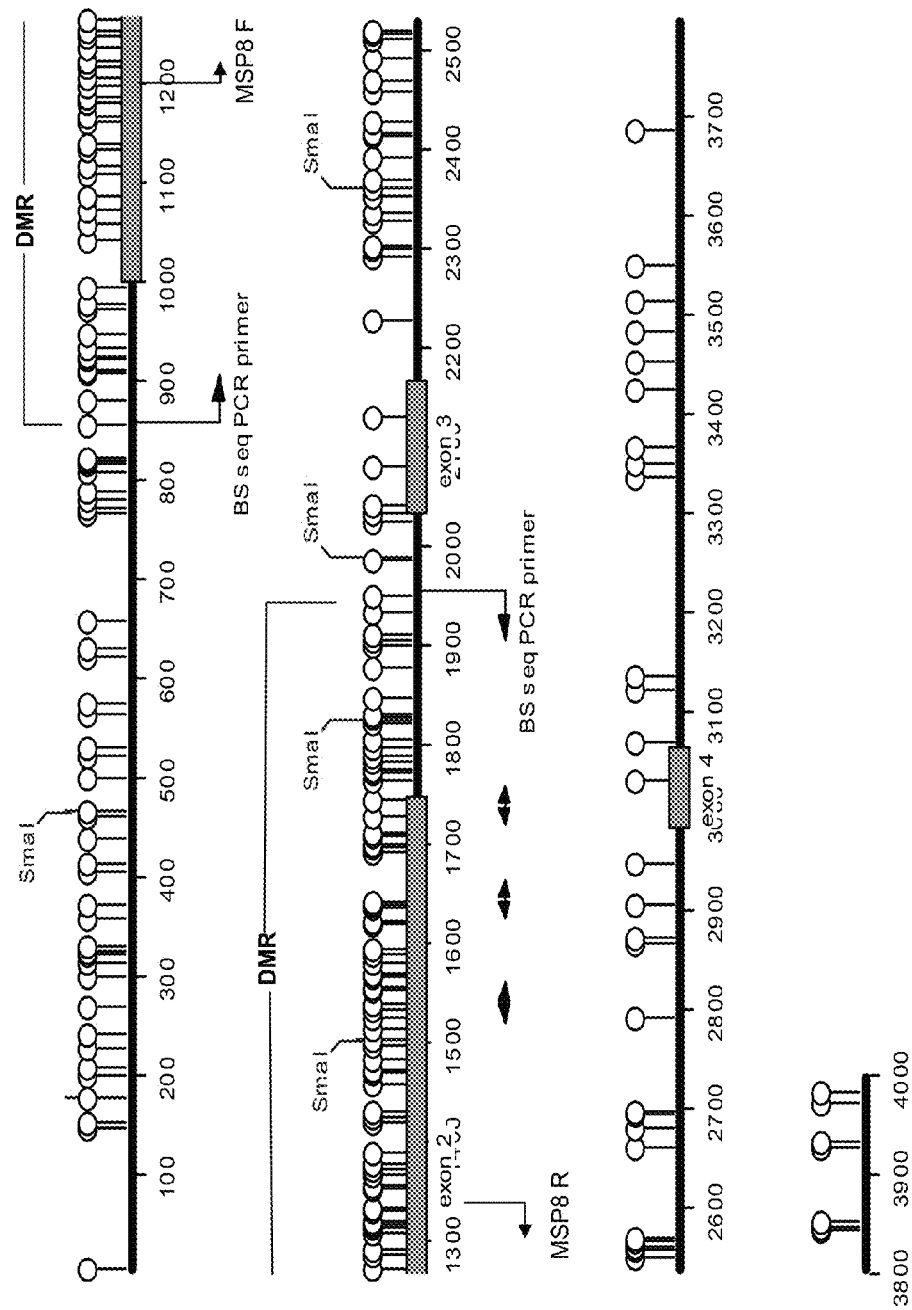
FIG. 3. Schematic of the 1-4000 bp C6Orf150 genomic locus above as defined in the Ensembl Genome Browser. The first coding exon is denoted as exon 2 (in UCSC Genome browser the exon 2 is annotated as exon 1). Balloons denote the positions of CpG dinucleotides. Double headed arrows denote the positions of oligonucleotide probes present on the Agilent human CpG island microarray. Also shown is the position of outer PCR primers used for amplification of a C6Orf150 differentially methylated region ("BS seq PCR primer"), as well as the position of PCR primers that define MSP-8 target region domain ("MSP8 F" and "MSP8 R").
Figure 4:
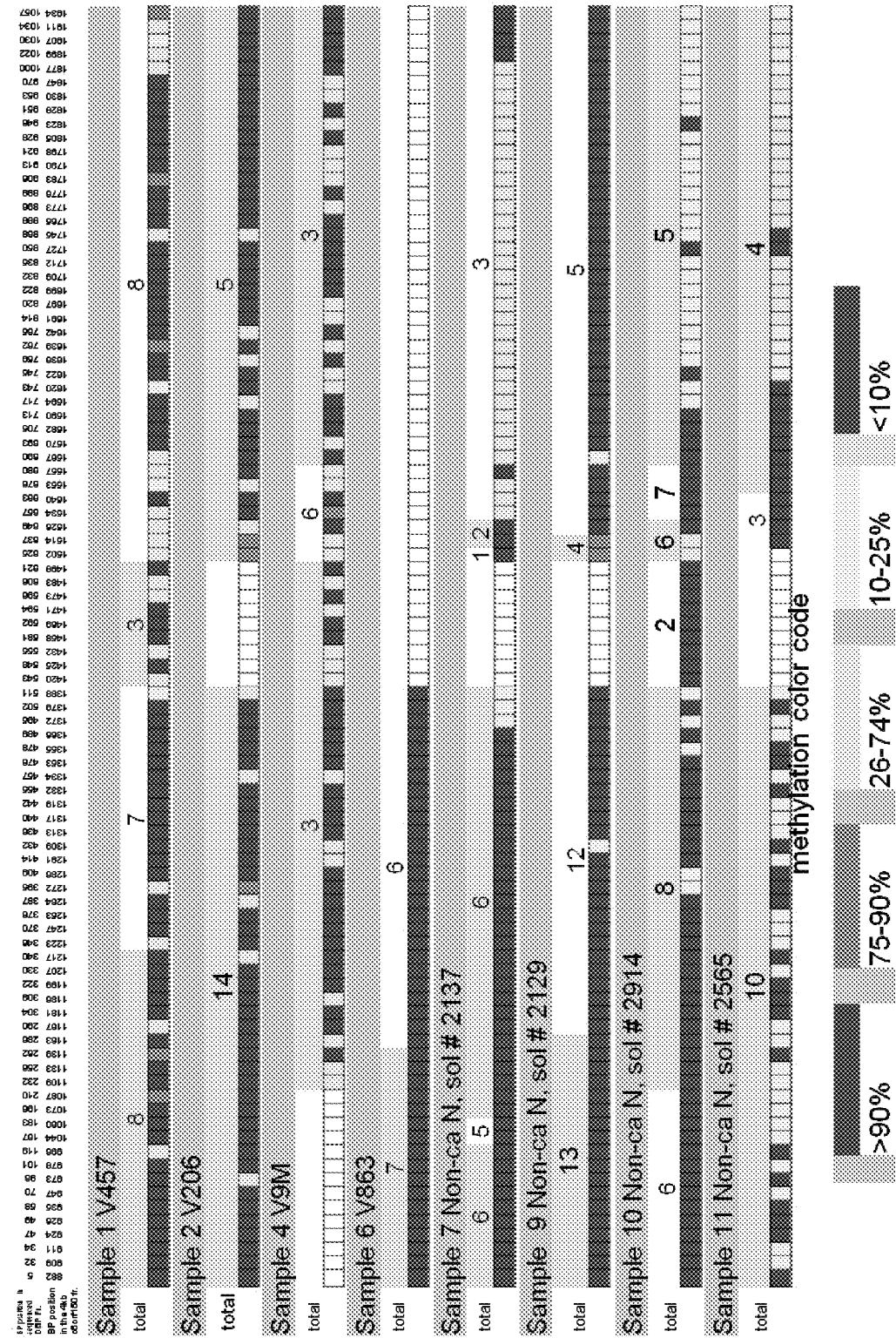
FIG. 4. Heat map showing sequencing results of bisulfite converted DNAs across the differentially methylated region (DMR), corresponding to template SEQ ID NO: 7 in 4 samples of normal colon mucosa from individuals who did not have colon cancer (Non-CA N, for Non-Cancer Normal), versus 4 colon cancer cell lines (V457, V9m, V206, V863). Each CpG within the region is denoted along the X-axis. CpG cytosines are designated sequentially (CpG number in DMR) in the top row, then designated by actual basepair position in the differentially methylated domain (SEQ ID NO: 7) (BP Position in Sequenced DMR Fr), then designated by actual basepair position in the 4 kb C6Orf150 genomic domain (SEQ ID NO: 1). Red regions denote CpG positions for which 90% or more of sequenced clones denoted methylation. It is apparent that there is more methylation in the cancer samples than in the normal colon samples.

"Differentially Methylated Region" (DMR) and "MSP8" region as used herein refer to those regions of C6Orf150 that are found to be differentially methylated. For example, FIG. 3 discloses a C6Orf150 region wherein certain sequences of this gene are differentially methylated (e.g., SEQ ID NOs: 7 and 13).

"C6Orf150-nucleotide sequence" or "C6Orf150-nucleic acid sequence" as used herein refers to the C6Orf150-genomic sequences as set forth in SEQ ID NOs: 1-18, and fragments thereof.

"C6Orf150-silencing associated diseases" as used herein includes C6Orf150-associated neoplasia.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated or "non-homologous" shares less than 40% identity, preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (*Computational Molecular Biology*, Lesk, A. M., ed., Oxford University Press, New York, 1988; *Biocomputing*: Informatics and Genome Projects, Smith, D. W., ed., Academic Press, New York, 1993; *Computer Analysis of Sequence Data*, Part I, Griffin, A. M., and Griffin, H. G., eds., Humana Press, New Jersey, 1994; Sequence Analysis in Molecular Biology, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990)). The well known Smith Waterman algorithm may also be used to determine identity.

The term "including" is used herein to mean, and is used interchangeably with, the phrase "including but not limited to."

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The term "methylation-sensitive PCR" (i.e., MSP) herein refers to a polymerase chain reaction in which amplification of the compound-converted template sequence is performed. Two sets of primers are designed for use in MSP. Each set of primers comprises a forward primer and a reverse primer. One set of primers, called methylation-specific primers (see below), will amplify the compound-converted template sequence if C bases in CpG dinucleotides within the C6Orf150 DNA are methylated.

The term "methylation-indifferent PCR" or "methylation-insensitive PCR" herein refers to a polymerase chain reaction in which amplification of the compound-converted template sequence is performed. Sets of primers are designed for use. Each set of primers comprises a forward primer and a reverse primer and will amplify the compound-converted template sequence irrespective of whether C bases in CpG dinucleotides within the C6Orf150 DNA are methylated or not methylated.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "proteins" and "polypeptides" are used interchangeably herein.

A "sample" includes any material that is obtained or prepared for detection of a molecular marker or a change in a molecular marker such as for example the methylation state, or any material that is contacted with a detection reagent or detection device for the purpose of detecting a molecular marker or a change in the molecular marker.

A "subject" is any organism of interest, generally a mammalian subject, such as a mouse, and preferably a human subject.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As applied to polypeptides, the term "substantial sequence identity" means that two peptide sequences, when optimally aligned such as by the programs GAP or BESTFIT using default gap, share at least 90 percent sequence identity, preferably at least 95 percent sequence identity, more preferably at least 99 percent sequence identity or more. Preferably, residue positions which are not identical differ by conservative amino acid substitutions. For example, the substitution of amino acids having similar chemical properties such as charge or polarity is not likely to effect the properties of a protein. Examples include glutamine for asparagine or glutamic acid for aspartic acid.

As used herein, the term "transgene" means a nucleic acid sequence (encoding, e.g., a C6Orf150 polypeptide), which is partly or entirely heterologous (i.e., foreign) to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A C6Orf150 transgene can include one or more transcriptional regulatory sequences and any other nucleic acid, such as introns, that may be necessary for optimal expression of a selected nucleic acid. A C6Orf150 transgene can include a C6Orf150 nucleotide sequence (e.g., SEQ ID NO: 1) or fragments thereof.

II. Overview

In certain aspects, the invention relates to methods for determining whether a patient is likely or unlikely to have a colon neoplasia. A colon neoplasia is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. Moving outward from the lumen, the layers are termed the mucosa, the submucosa, the muscularis propria and the subserosa. The mucosa includes the epithelial layer (cells adjacent to the lumen), the basement membrane, the lamina propria and the muscularis mucosae. In general, the "wall" of the colon is intended to refer to the submucosa and the layers outside of the submucosa. The "lining" is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers.

When a colon neoplasia invades into the basement membrane of the colon, it is considered a colon cancer, as the term "colon cancer" is used herein. In describing colon cancers, this specification will generally follow the so-called "Dukes" colon cancer staging system. The characteristics that describe a cancer are generally of greater significance than the particular term used to describe a recognizable stage. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

"Dukes A" and "Dukes B" colon cancers are neoplasias that have invaded into the wall of the colon but have not spread into other tissues. Dukes A colon cancers are cancers that have not invaded beyond the submucosa. Dukes B colon cancers are subdivided into two groups: Dukes B1 and Dukes B2. "Dukes B1" colon cancers are neoplasias that have invaded up to but not through the muscularis propria. Dukes B2 colon cancers are cancers that have breached completely through the muscularis propria. Over a five year period, patients with Dukes A cancer who receive surgical treatment (i.e. removal of the affected tissue) have a greater than 90% survival rate. Over the same period, patients with Dukes B1 and Dukes B2 cancer receiving surgical treatment have a survival rate of about 85% and 75%, respectively. Dukes A, B1 and B2 cancers are also referred to as T1, T2 and T3-T4 cancers, respectively.

"Dukes C" colon cancers are cancers that have spread to the regional lymph nodes, such as the lymph nodes of the gut. Patients with Dukes C cancer who receive surgical treatment alone have a 35% survival rate over a five year period, but this survival rate is increased to 60% in patients that receive chemotherapy.

"Dukes D" colon cancers are cancers that have metastasized to other organs. The liver is the most common organ in which metastatic colon cancer is found. Patients with Dukes D colon cancer have a survival rate of less than 5% over a five year period, regardless of the treatment regimen.

In general, colon neoplasia develops through one of at least three different pathways, termed chromosomal instability, microsatellite instability, and the CpG island methylator phenotype (CIMP). Although there is some overlap, these pathways tend to present somewhat different biological behavior. By understanding the pathway of tumor development, the target genes involved, and the mechanisms underlying the genetic instability, it is possible to implement strategies to detect and treat the different types of colon neoplasias.

This application is based, at least in part, on the recognition that certain target genes may be silenced or inactivated by the differential methylation of CpG islands in the 5' flanking or promoter regions of the target gene. CpG islands are clusters of cytosine-guanosine residues in a DNA sequence, which are prominently represented in the 5-flanking region or promoter region of about half the genes in our genome. In particular, this application is based, at least in part, on the recognition that differential methylation of the C6Orf150 nucleotide sequence may be indicative of colon neoplasia. In one aspect, this application discloses that the C6Orf150 gene can be a common target for methylation and epigenetic gene silencing in cancer cells (e.g., a colon neoplasia), and may function as a candidate tumor suppressor gene.

In certain aspects, the present invention describes CpG methylation in the region covering the first coding exon of the C6Orf150 gene as a diagnostic biomarker of human colorectal cancer. In related embodiments, disclosed herein is the use of assays for detecting aberrant methylation of the C6Orf150 gene. Also disclosed herein is the bisulfite converted sequence of the methylated form, as well as the unmethylated form of the C6Orf150 gene. In another embodiment disclosed herein are sets of primers for methylation specific PCR assays to detect the methylated status of this gene. In a preferred embodiment, this invention describes a subregion (the C6Orf150 differentially methylated region; "DMR") that is highly methylated in a subset of colon cancers, and is much less methylated in normal colon tissues. In a related embodiment, this invention describes a further subregion (the "MSP8" target region) that is highly methylated in a subset of colon cancers, and is not detectably or rarely methylated in normal colon tissues.

The present invention also describes PCR primers and a methylation specific PCR assay for detecting aberrant methylation of the C6Orf150 gene. Aberrant methylation of the C6Orf150 differentially methylated region (DMR), and/or of the MSP8 target region, may be used as a biomarker to detect the presence of colon neoplasias, including colon cancers. The method of detection includes testing for the presence of DNA demonstrating methylation of the C6Orf150 DMR and/or the MSP8 target region that may be detectable in human tissues, or that may be shed from the tumor and be detectable in human body fluids. As described herein, human body fluids include but are not limited to blood, blood fractions, stool, and urine.

Detection of DNA with methylation in the C6Orf150 DMR and/or the MSP-8 target region may be used for detecting the presence of colon neoplasia, including colon cancers. Detection of any increase or decrease in DNA methylation within the C6Orf150 DMR and/or the MSP-8 target region may be used for monitoring of individuals with colon cancers. Decreases in levels of methylation in the C6Orf150 DMR and/or the MSP-8 target region would indicate a response to a therapeutic intervention, whereas increases in levels of methylation in the C6Orf150 DMR and/or the MSP-8 target region would indicate progression or recurrence of disease.

Further, tests for aberrant methylation of C6Orf150 may be combined in a panel with tests for other colon cancer biomarkers (e.g., vimentin, SLC5A8, HLTF, p16, and hMLH1), particularly with tests for aberrant vimentin gene methylation, so as to provide increased sensitivity for detection of colon neoplasia. The utility of vimentin as a colon cancer biomarker is disclosed in U.S. Pat. No. 7,485,420.

Aberrant methylation of C6Orf150 is associated with decreased expression of C6Orf150 mRNA. Accordingly, decreased expression of C6Orf150 mRNA or protein may also be employed as a diagnostic biomarker of colon cancers. Colon cancer cells that demonstrate methylation of C6Orf150 and/or reduced expression of C6Orf150 may be used to assay for substances or compounds that can reactivate expression of C6Orf150 in colon cancer cells.

As noted above, early detection of colon neoplasia, coupled with appropriate intervention, is important for increasing patient survival rates. Present systems for screening for colon neoplasia are deficient for a variety of reasons, including a lack of specificity and/or sensitivity (e.g., Fecal Occult Blood Test, flexible sigmoidoscopy), or a high cost and intensive use of medical resources (e.g., colonoscopy). Alternative systems for detection of colon neoplasia would be useful in a wide range of other clinical circumstances as well. For example, patients who receive surgical and/or pharmaceutical therapy for colon cancer may experience a relapse. It would be advantageous to have an alternative system for determining whether such patients have a recurrent or relapsed colon neoplasia. As a further example, an alternative diagnostic system would facilitate monitoring an increase, decrease or persistence of colon neoplasia in a patient known to have a colon neoplasia. A patient undergoing chemotherapy may be monitored to assess the effectiveness of the therapy.

III. C6Orf150 Nucleic Acids, Polypeptides, and Antibodies.

The present invention is based, at least in part, on the observation that C6Orf150 nucleotide sequences are differentially methylated in certain C6Orf150-associated neoplasia, such as colon neoplasia. In one aspect, the application discloses C6Orf150 nucleotide sequences having certain regions that are differentially methylated in C6Orf150-associated neoplasia, for example, SEQ ID NOs: 1-18 and fragments thereof. Accordingly, in one embodiment, the application provides isolated or recombinant nucleotide sequences that are at least 80%, 85%, 90%, 95%, 97%, 98%, 99% or 100% identical to the differentially methylated nucleic acid sequences, wherein detection of methylation in any one of said differentially methylated nucleic acid sequences would be indicative of a C6Orf150-associated neoplasia such as colon neoplasia. One of ordinary skill in the art will appreciate that C6Orf150 nucleic acid sequences complementary to SEQ ID NOs: 1-18, and variants thereof, are also within the scope of this invention. Such variant nucleotide sequences include sequences that differ by one or more nucleotide substitutions, additions or deletions, such as allelic variants.

In yet other embodiments, C6Orf150 nucleotide sequences also include nucleotide sequences that will hybridize under highly stringent conditions to the nucleotide sequences designated in SEQ ID NO: 1-18, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

In yet another aspect, the application provides the methylated forms of nucleotide sequence of SEQ ID NO: 1, 7, 13 or fragments thereof, wherein the cytosine bases of the CpG islands present in said sequences are methylated. In other words, the C6Orf150 nucleotide sequences may be either in the methylated status (e.g., as seen in C6Orf150-associated neoplasias) or in the unmethylated status (e.g., as seen in normal cells). In further embodiments, the C6Orf150 nucleotide sequences of the invention can be isolated, recombinant, and/or fused with a heterologous nucleotide sequence, or in a DNA library.

In addition to the differentially methylated C6Orf150 nucleotide sequences, constitutively methylated nucleotide sequences are also present in the C6Orf150 sequence. Since constitutively methylated C6Orf150 nucleotide sequences are methylated in both normal cells and cancer cells, a person skilled in the art would appreciate the significance of detecting the differentially methylated C6Orf150 nucleotide sequences as provided herein.

In certain embodiments, the present invention provides bisulfite-converted C6Orf150 template DNA sequences, for example, SEQ ID NOs: 2-3, 5-6, 8-9, 11-12, 14-15, 17-18, and fragments thereof. Such bisulfite-converted C6Orf150 template DNA can be used for detecting the methylation status, for example, by an MSP reaction or by direct sequencing. These bisulfite-converted C6Orf150 sequences are also of use for designing primers for MS-PCR reactions that specifically detect methylated or unmethylated C6Orf150 templates following bisulfite conversion. In yet other embodiments, the bisulfite-converted C6Orf150 nucleotide sequences of the invention also include nucleotide sequences that will hybridize under highly stringent conditions to any nucleotide sequence selected from SEQ ID NOs: 2-3, 5-6, 8-9, 11-12, 14-15, 17-18, or complements thereof.

In further aspects, the application provides methods for producing such bisulfite-converted nucleotide sequences, for example, the application provides methods for treating a nucleotide sequence with a bisulfite agent such that the unmethylated cytosine bases are converted to a different nucleotide base such as a uracil.

In yet other aspects, the application provides oligonucleotide primers for amplifying a region within the C6Orf150 nucleic acid sequence of any one of SEQ ID NOs: 19-138, as shown in Table 2. In certain aspects, a pair of the oligonucleotide primers can be used in a detection assay, such as the HpaII assay. In certain aspects, primers used in an MSP reaction can specifically distinguish between methylated and non-methylated C6Orf150 DNA, for example, SEQ ID NOs: 19-138.

The primers of the invention have sufficient length and appropriate sequence so as to provide specific initiation of amplification of C6Orf150 nucleic acids. Primers of the invention are designed to be "substantially" complementary to each strand of the C6Orf150 nucleic acid sequence to be amplified. While exemplary primers are provided in SEQ ID NOs: 19-138, it is understood that any primer that hybridizes with the bisulfite-converted C6Orf150 sequence of SEQ ID NO: 1, 7, or 13 are included within the scope of this invention and is useful in the method of the invention for detecting methylated nucleic acid, as described. Similarly, it is understood that any primers that would serve to amplify a methylation sensitive restriction site or sites within the differentially methylated region of SEQ ID NO: 1, 7, or 13 are included within the scope of this invention and is useful in the method of the invention for detecting nucleic methylated nucleic acid, as described.

The oligonucleotide primers of the invention may be prepared by using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859-1862, 1981). One method for synthesizing oligonucleotides on a modified solid support is described in U.S. Pat. No. 4,458,066.

The various Sequence Identification Numbers that have been used in this application are summarized below in Table 1.

TABLE 1

Sequence Identification Numbers of C6Orf150 template seqences disclosed in this application.

| SEQ ID NO: | Description |
|---|---|
| 1 | minus strand of chr6:74,215,720-74,219,719, UCSC Genome Browser on Human March 2006 Assembly (hg18), listed 5' to 3'; corresponds to the sense strand relative to C6orf150 mRNA sequence |
| 2 | minus strand of chr6:74,215,720-74,219,719, UCSC Genome Browser on Human March 2006 Assembly (hg18), fully CpG methylated minus strand after bisulfate conversion, listed 5' to 3', of SEQ ID NO: 1 |
| 3 | minus strand of chr6:74,215,720-74,219,719, UCSC Genome Browser on Human March 2006 Assembly (hg18), completely unmethylated minus strand after bisulfate conversion, listed 5' to 3', of SEQ ID NO: 1 |
| 4 | plus strand of chr6:74,215,720-74,219,719, UCSC Genome Browser on Human March 2006 Assembly (hg18), listed 5' to 3'; corresponds to the ANTIsense strand relative to c6orf150 mRNA sequence (antisense relatvie to SEQ ID NO: 1) |
| 5 | plus strand of chr6:74,215,720-74,219,719, UCSC Genome Browser on Human March 2006 Assembly (hg18); fully CpG methylated plus strand after bisulfate conversion, listed 5' to 3', of SEQ ID NO: 4 |
| 6 | plus strand of chr6:74,215,720-74,219,719, UCSC Genome Browser on Human March 2006 Assembly (hg18); completely UNmethylated plus strand after bisulfate conversion, listed 5' to 3' of SEQ ID NO: 4 |
| 7 | minus strand of chr6: 74,217,783-74,218,842, UCSC Genome Browser on Human March 2006 Assembly (hg18) listed 5' to 3'; corresponds to the sense strand relative to c6orf150 mRNA sequence; denoted herein as subregion of c6orf150 that is a "differentially methylated region" (DMR) |
| 8 | minus strand of chr6: 74,217,783-74,218,842, UCSC Genome Browser on Human March 2006 Assembly (hg18); fully CpG methylated minus strand after bisulfate conversion, listed 5' to 3', of SEQ ID NO: 7 |
| 9 | minus strand of chr6: 74,217,783-74,218,842, UCSC Genome Browser on Human March 2006 Assembly (hg18); completely unmethylated minus strand after bisulfate conversion, listed 5' to 3', of SEQ ID NO: 7 |
| 10 | plus strand of chr6: 74,217,783-74,218,842, UCSC Genome Browser on Human March 2006 Assembly (hg18), listed 5' to 3'; corresponds to the ANTIsense strand relative to c6orf150 mRNA sequence (antisense relative to SEQ ID NO: 7); denoted herein as subregion of c6orf150 that is a "differentially methylated region" (DMR) |
| 11 | plus strand of chr6: 74,217,783-74,218,842, UCSC Genome Browser on Human March 2006 Assembly (hg18); fully CpG methylated plus strand after bisulfate conversion, listed 5' to 3', of SEQ ID NO: 10 |
| 12 | plus strand of chr6: 74,217,783-74,218,842, UCSC Genome Browser on Human March 2006 Assembly (hg18); completely UNmethylated plus strand after bisulfate conversion, listed 5' to 3', of SEQ ID NO: 10 |
| 13 | minus strand of chr6: 74,218,391-74,218,520, UCSC Genome Browser on Human March 2006 Assembly (hg18), listed 5' to 3'; corresponds to the sense strand relative to c6orf150 mRNA sequence; denoted herein as subregion of c6orf150 that is a differentially methylated region (MSP8) |
| 14 | minus strand of chr6: 74,218,391-74,218,520, UCSC Genome Browser on Human March 2006 Assembly (hg18); fully CpG methylated minus strand after bisulfate conversion, listed 5' to 3', of SEQ ID NO: 13 |
| 15 | minus strand of chr6: 74,218,391-74,218,520, UCSC Genome Browser on Human March 2006 Assembly (hg18); completely unmethylated minus strand after bisulfate conversion, listed 5' to 3', of SEQ ID NO: 13 |
| 16 | plus strand of chr6: 74,218,391-74,218,520, UCSC Genome Browser on Human March 2006 Assembly (hg18) listed 5' to 3'; corresponds to the ANTIsense strand relative to c6orf150 mRNA sequence (antisense relative to SEQ ID NO: 13); denoted herein as subregion of c6orf150 that is a differentially methylated region (MSP8) |
| 17 | plus strand of chr6: 74,218,391-74,218,520, UCSC Genome Browser on Human March 2006 Assembly (hg18); fully CpG methylated plus strand after bisulfate conversion, listed 5' to 3', of SEQ ID NO: 16 |
| 18 | plus strand of chr6: 74,218,391-74,218,520, UCSC Genome Browser on Human March 2006 Assembly (hg18); completely UNmethylated plus strand after bisulfate conversion, listed 5' to 3', of SEQ ID NO: 16 |

In certain other aspects, the invention relates to C6Orf150 nucleic acids that encode the C6Orf150 polypeptide and variants thereof. Variant include sequences that differ by one or more nucleotide substitutions, additions or deletions, such as allelic variants; and will, therefore, include coding sequences that differ from the nucleotide sequence of the coding sequence e.g., due to the degeneracy of the genetic code. In certain embodiments, variant nucleic acids will also include sequences that will hybridize under highly stringent conditions to a nucleotide sequence encoding the C6Orf150 polypeptide.

Isolated C6Orf150 nucleic acids which differ from the nucleic acids encoding SEQ ID NO: 1 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant C6Orf150 nucleic acid may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the invention relates to C6Orf150 polypeptide described herein, and variant polypeptides thereof. In certain embodiments, variant polypeptides have an amino acid sequence that is at least 75% identical to the predicted amino acid sequence (hypothetical protein LOC115004, NCBI Reference Sequence: NP_612450.2). In other embodiments, the variant polypeptide has an amino acid sequence at least 80%, 85%, 90%, 95%, 97%, 98%, 99% or 100% identical to the predicted amino acid sequence.

In certain aspects, variant C6Orf150 polypeptides are agonists or antagonists of the C6Orf150 polypeptide. Variants of these polypeptides may have a hyperactive or constitutive activity, or, alternatively, act to prevent the tumor suppressor activity of C6Orf150. For example, a truncated form lacking one or more domain may have a dominant negative effect.

In certain aspects, isolated peptidyl portions of the C6Orf150 polypeptide can be obtained by screening polypeptides recombinantly produced from the corresponding fragment of the nucleic acid encoding the polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments which can function as either agonists or antagonists of the tumor suppressor function of C6Orf150.

In certain aspects, variant C60rf150 polypeptides comprise one or more fusion domains. Well known examples of such fusion domains include, for example, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion polypeptide by affinity chromatography. For the purpose of affinity purification, relevant matrices for affinity chromatography, such as glutathione-, amylase-, and nickel- or cobalt- conjugated resins are used. Many of such matrices are available in "kit" form, such as the Pharmacia GST purification system and the QIAexpress™ system (Qiagen) useful with (HIS$_6$) (SEQ ID NO: 147) fusion partners. Another fusion domain well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion C6Orf150 polypeptide. The GFP tag is also useful for isolating cells which express the fusion C6Orf150 polypeptide by flow cytometric methods such as a fluorescence activated cell sorting (FACS). Fusion domains also include "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allow the relevant protease to partially digest the fusion C6Orf150 polypeptide and thereby liberate the recombinant polypeptide therefrom. The liberated polypeptide can then be isolated from the fusion partner by subsequent chromatographic separation.

Another aspect of the invention pertains to an isolated antibody specifically immunoreactive with an epitope of a C6Orf150 polypeptide. For example, by using immunogens derived from a C6Orf150 polypeptide (e.g., based on its cDNA sequences), anti-protein/anti-peptide antisera or monoclonal antibodies can be made by standard protocols (see, for example, *Antibodies: A Laboratory Manual ed. by Harlow and Lane (Cold Spring Harbor Press:* 1988)). A mammal, such as a mouse, a hamster or rabbit can be immunized with an immunogenic form of the C6Orf150 peptide. Techniques for conferring immunogenicity on a protein or peptide include conjugation to carriers or other techniques well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In certain embodiment, antibodies of the invention may be useful as diagnostic or therapeutic agents for detecting or treating C6Orf150-associated diseases.

The term "antibody" as used herein is intended to include fragments thereof which are also specifically reactive with one of the C6Orf150 polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragments can be treated to reduce disulfide bridges to produce Fab fragments. The antibody of the invention is further intended to include bispecific, single-chain, and chimeric and humanized molecules having affinity for the C6Orf150 protein. In preferred embodiments, the antibody further comprises a label attached thereto and able to be detected, (e.g., the label can be a radioisotope, fluorescent compound, enzyme or enzyme co-factor).

IV. Assays and Drug Screening Methodologies

In certain aspects, the application provides assays and methods using the C6Orf150 nucleotide sequences as molecular markers that distinguish between healthy cells and C6Orf150-associated diseased cells. For example, in one embodiment, the application provides methods and assays using the C6Orf150 nucleotide sequences as markers that distinguish between healthy cells and colon neoplasia cells. In one aspect, a molecular marker of the invention is a differentially methylated C6Orf150 nucleotide sequence. In another aspect, another marker provided herein is the C6Orf150 gene expression product.

In certain embodiments, the invention provides assays for detecting differentially methylated C6Orf150 nucleotide sequences, such as the differential methylation patterns seen in the Differentially Methylated Region ("DMR"; SEQ ID NO: 7), as well as its subset region disclosed herein as MSP-8 domain (SEQ ID NO: 13 and, further, any fragment thereof. By way of example, in certain embodiments such a fragment includes at least one site of methylation (i.e., C) that can be assayed for methylation, and is of a length that is amenable to MS-PCR and/or digestion by a methylation-specific restriction enzyme to produce a detectable signal. In other embodiments, the fragment includes at least 1, 2, 3, 4, 5, 6, 7, 8, 9, or 10 sites of methylation. Thus, a differentially methylated C6Orf150 nucleotide sequence or any fragment thereof, in its methylated state, can be a C6Orf150-associated neoplasia-specific modification that serves as a target for detection using various methods described herein and the methods that are well within the purview of the skilled artisan in view of the teachings of this application.

In certain aspects, such methods for detecting methylated C6Orf150 nucleotide sequences are based on treatment of C6Orf150 genomic DNA with a chemical compound which converts non-methylated C, but not methylated C (i.e., 5 mC), to a different nucleotide base. One such compound is sodium bisulfite, which converts C, but not 5 mC, to U. Methods for bisulfite treatment of DNA are known in the art (Herman, et al., 1996, Proc Natl Acad Sci USA, 93:9821-6; Herman and Baylin, 1998, Current Protocols in Human Genetics, N. E. A. Dracopoli, ed., John Wiley & Sons, 2:10.6.1-10.6.10; U.S. Pat. No. 5,786,146). To illustrate, when a DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a preferred embodiment, the present invention provides a method of detecting U in compound-converted C6Orf150 DNA sequences by using "methylation sensitive PCR" (MSP) (see, e.g., Herman, et al., 1996, *Proc. Natl. Acad. Sci. USA,* 93:9821-9826; U.S. Pat. Nos. 6,265,171; 6,017,704; 6,200,756). In MSP, one set of primers (i.e., comprising a forward and a reverse primer) amplifies the compound-converted template sequence if C bases in CpG dinucleotides within the C6Orf150 DNA are methylated. This set of primers is called "methylation-specific primers." Another set of primers amplifies the compound-converted template sequence if C bases in CpG dinucleotides within the C6Orf150 5' flanking sequence are not methylated. This set of primers is called "unmethylation-specific". In addition, primers may be designed that will amplify the compound-converted template sequence irrespective of whether C bases in CpG dinucleotides within the C6Orf150 5' flanking sequence are or are not methylated. Such primers are termed "methylation-indifferent."

In MS-PCR, the reactions use the compound-converted DNA from a sample in a subject. In assays for C6Orf150 methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA is not methylated, the methylation-specific primers will not amplify the compound-converted template sequence in the presence of a polymerase and an MSP product will not be produced.

It is often also useful to run a control reaction for the detection of unmethylated C6Orf150 DNA. The reaction uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA is methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethylation specific signal is often of use as a control reaction, but does not in this instance imply the absence of colon neoplasia as indicated by the positive signal derived from reactions using the methylation specific primers.

Primers for an MSP reaction are typically derived from the compound-converted C6Orf150 template sequence. Herein, "derived from" means that the sequences of the primers are chosen such that the primers amplify the compound-converted template sequence in an MSP reaction. Each primer comprises a single-stranded DNA fragment which is at least 8 nucleotides in length. Preferably, each primer comprises a single-stranded DNA fragment which is at least 10, 11, 12, 13, or 14 nucleotides in length. In certain embodiments, the primers are less than 50 nucleotides in length, more preferably from 15 to 35 nucleotides in length. Because the compound-converted C6Orf150 template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted C6Orf150 template sequence, and therefore the product of the MSP reaction, can be between 20 to 3000 nucleotides in length, preferably between 50 to 500 nucleotides in length, more preferably between 80 to 150 nucleotides in length. Preferably, the methylation-specific primers result in an MSP product of a different length than the MSP product produced by the unmethylation-specific primers.

By way of example, provided below are exemplary MSP primers (primer sets MSP1-MSP61). Summarized in Table 2A are primer pairs for methylation specific PCR (MSP) reactions MSP1 through MSP61 that interrogate the C6Orf150 differentially methylated domain (SEQ ID NO: 7 and its complementary strand SEQ ID NO: 10) for methylation. All of the MSP reactions are designed to amplify the bisulfite converted sequences from fully methylated segments that span SEQ ID NO: 7 (i.e., SEQ ID NO: 8). The MSP reactions are comprised of MSP primers whose sequences are provided as SEQ ID NO: 19 through SEQ ID NO: 138. The coordinate of the 5' end of each primer relative to SEQ ID NO: 1, and its methylated form SEQ ID NO: 2 is also shown (numbers corresponding to 4000 by fragment). SEQ ID NO: 31 and 32, respectively, provide the sequences of the forward and reverse primers for reaction MSP-8. Below, odd sequence numbers correspond to the forward primers for each MSP pair, and the even sequence numbers correspond to the reverse primers for each MSP pair. In general, new MSP reactions may be created by pairing of a forward primer from the list of forward primers with a reverse primer from the list of reverse primers.

TABLE 2A

C6Orf150 MSP primer sets.

| SEQ ID NO: | Primer Set | Primer Name | Primer Sequence | Position of 5' end relative to SEQ ID NOs: 1 & 2 |
|---|---|---|---|---|
| 19 | MSP1 | 1c6-958FM | TTTGGGGTTTTTTTCGGGTCGT | 958 |
| 20 | | 39c6-1186RM | GAAACGCCCCTAACATTCCGTACGA | 1186 |
| 21 | MSP2 | 2c6-1120FM | TGTAGAGAGTTTTCGAGGTCGG | 1120 |
| 22 | | 39c6-1186RM | GAAACGCCCCTAACATTCCGTACGA | 1186 |
| 23 | MSP3 | 2c6-1120FM | TGTAGAGAGTTTTCGAGGTCGG | 1120 |
| 24 | | 38c6-1230RM | ACAAAACGACCTCGAAAACAACCGA | 1230 |
| 25 | MSP5 | 3c6-1141FM | GAGTTATTGTTTTTAAGGTTTTCGTACGG | 1141 |
| 26 | | 38c6-1230RM | ACAAAACGACCTCGAAAACAACCGA | 1230 |
| 27 | MSP6 | 3c6-1141FM | GAGTTATTGTTTTTAAGGTTTTCGTACGG | 1141 |
| 28 | | 37c6-1329RM | CCCCAATTACGCGAACGAACGA | 1329 |
| 29 | MSP7 | 4c6-1166FM | ACGGAATGTTAGGGGCGTTTCG | 1166 |
| 30 | | 37c6-1329RM | CCCCAATTACGCGAACGAACGA | 1329 |
| 31 | MSP8 | 5c6-1200FM | GAGTTTTCGGTTGTTTTCGAGGTCGT | 1200 |
| 32 | | 37c6-1329RM | CCCCAATTACGCGAACGAACGA | 1329 |
| 33 | MSP9 | 6c6-1267FM | GATTTCGGTAGAAAAAGAGCGTTTCGG | 1267 |
| 34 | | 37c6-1329RM | CCCCAATTACGCGAACGAACGA | 1329 |
| 35 | MSP10 | 4c6-1166FM | ACGGAATGTTAGGGGCGTTTCG | 1166 |
| 36 | | 36c6-1377RM | CAAACGACTACGTATCCTAAACGCGCT | 1377 |
| 37 | MSP11 | 5c6-1200FM | GAGTTTTCGGTTGTTTTCGAGGTCGT | 1200 |
| 38 | | 36c6-1377RM | CAAACGACTACGTATCCTAAACGCGCT | 1377 |
| 39 | MSP12 | 6c6-1267FM | GATTTCGGTAGAAAAAGAGCGTTTCGG | 1267 |
| 40 | | 36c6-1377RM | CAAACGACTACGTATCCTAAACGCGCT | 1377 |
| 41 | MSP13 | 7c6-1300FM | AGGAGAGGTCGTTCGTTCGCGT | 1300 |
| 42 | | 36c6-1377RM | CAAACGACTACGTATCCTAAACGCGCT | 1377 |
| 49 | MSP17 | 5c6-1200FM | GAGTTTTCGGTTGTTTTCGAGGTCGT | 1200 |
| 50 | | 35c6-1392RM | AAACGCTAATAACGTCAAACGACTACGT | 1392 |
| 51 | MSP18 | 6c6-1267FM | GATTTCGGTAGAAAAAGAGCGTTTCGG | 1267 |
| 52 | | 35c6-1392RM | AAACGCTAATAACGTCAAACGACTACGT | 1392 |
| 53 | MSP19 | 7c6-1300FM | AGGAGAGGTCGTTCGTTCGCGT | 1300 |
| 54 | | 35c6-1392RM | AAACGCTAATAACGTCAAACGACTACGT | 1392 |
| 55 | MSP20 | 7c6-1300FM | AGGAGAGGTCGTTCGTTCGCGT | 1300 |
| 56 | | 34c6-1516RM | ACGTCCCAAAACCCGAACGAGA | 1516 |
| 57 | MSP21 | 10c6-1350FM | TAGCGCGTTTAGGATACGTAGTCGT | 1350 |
| 58 | | 34c6-1516RM | ACGTCCCAAAACCCGAACGAGA | 1516 |
| 59 | MSP22 | 11c6-1414FM | TTTTTGCGGTTCGGGAGTCGG | 1414 |
| 60 | | 34c6-1516RM | ACGTCCCAAAACCCGAACGAGA | 1516 |

TABLE 2A-continued

C6Orf150 MSP primer sets.

| SEQ ID NO: | Primer Set | Primer Name | Primer Sequence | Position of 5' end relative to SEQ ID NOs: 1 & 2 |
|---|---|---|---|---|
| 61 | MSP23 | 10c6-1350FM | TAGCGCGTTTAGGATACGTAGTCGT | 1350 |
| 62 | | 33c6-1548RM | TAAAAACCGAAACCGACAAACCGA | 1548 |
| 63 | MSP24 | 11c6-1414FM | TTTTTGCGGTTCGGGAGTCGG | 1414 |
| 64 | | 33c6-1548RM | TAAAAACCGAAACCGACAAACCGA | 1548 |
| 65 | MSP25 | 12c6-1456FM | GTCGTTAGAGGGGCGCGCGT | 1456 |
| 66 | | 33c6-1548RM | TAAAAACCGAAACCGACAAACCGA | 1548 |
| 67 | MSP26 | 10c6-1350FM | TAGCGCGTTTAGGATACGTAGTCGT | 1350 |
| 68 | | 32c6-1572RM | ACGCCGCATCCCTCCGTACGA | 1572 |
| 69 | MSP27 | 11c6-1414FM | TTTTTGCGGTTCGGGAGTCGG | 1414 |
| 70 | | 32c6-1572RM | ACGCCGCATCCCTCCGTACGA | 1572 |
| 71 | MSP28 | 12c6-1456FM | GTCGTTAGAGGGGCGCGCGT | 1456 |
| 72 | | 32c6-1572RM | ACGCCGCATCCCTCCGTACGA | 1572 |
| 73 | MSP29 | 13c6-1480FM | TTACGAAGTTAAGATTCTCGTTCGG | 1480 |
| 74 | | 32c6-1572RM | ACGCCGCATCCCTCCGTACGA | 1572 |
| 75 | MSP30 | 11c6-1414FM | TTTTTGCGGTTCGGGAGTCGG | 1414 |
| 76 | | 31c6-1602RM | CCAAAACCGCCCGAAACTTCGA | 1602 |
| 77 | MSP31 | 12c6-1456FM | GTCGTTAGAGGGGCGCGCGT | 1456 |
| 78 | | 31c6-1602RM | CCAAAACCGCCCGAAACTTCGA | 1602 |
| 79 | MSP32 | 13c6-1480FM | TTACGAAGTTAAGATTCTCGTTCGG | 1480 |
| 80 | | 31c6-1602RM | CCAAAACCGCCCGAAACTTCGA | 1602 |
| 81 | MSP33 | 14c6-1511FM | GGACGTGTTTAGTTTCGGTTTGTCGG | 1511 |
| 82 | | 31c6-1602RM | CCAAAACCGCCCGAAACTTCGA | 1602 |
| 83 | MSP34 | 12c6-1456FM | GTCGTTAGAGGGGCGCGCGT | 1456 |
| 84 | | 30c6-1641RM | CCGCCGTAAAAATATCATCGCGA | 1641 |
| 85 | MSP35 | 13c6-1480FM | TTACGAAGTTAAGATTCTCGTTCGG | 1480 |
| 86 | | 30c6-1641RM | CCGCCGTAAAAATATCATCGCGA | 1641 |
| 87 | MSP36 | 14c6-1511FM | GGACGTGTTTAGTTTCGGTTTGTCGG | 1511 |
| 88 | | 30c6-1641RM | CCGCCGTAAAAATATCATCGCGA | 1641 |
| 89 | MSP37 | 15c6-1532FM | GTCGGTTTCGGTTTTTATTTTCGTACGG | 1532 |
| 90 | | 30c6-1641RM | CCGCCGTAAAAATATCATCGCGA | 1641 |
| 91 | MSP38 | 16c6-1551FM | TTCGTACGGAGGGATGCGGCGT | 1551 |
| 92 | | 30c6-1641RM | CCGCCGTAAAAATATCATCGCGA | 1641 |
| 93 | MSP39 | 12c6-1456FM | GTCGTTAGAGGGGCGCGCGT | 1456 |
| 94 | | 29c6-1652RM | CACCATCCCCGCCGCCGT | 1652 |
| 95 | MSP40 | 13c6-1480FM | TTACGAAGTTAAGATTCTCGTTCGG | 1480 |
| 96 | | 29c6-1652RM | CACCATCCCCGCCGCCGT | 1652 |

TABLE 2A-continued

C6Orf150 MSP primer sets.

| SEQ ID NO: | Primer Set | Primer Name | Primer Sequence | Position of 5' end relative to SEQ ID NOs: 1 & 2 |
|---|---|---|---|---|
| 97 | MSP41 | 14c6-1511FM | GGACGTGTTTAGTTTCGGTTTGTCGG | 1511 |
| 98 | | 29c6-1652RM | CACCATCCCCGCCGCCGT | 1652 |
| 99 | MSP42 | 15c6-1532FM | GTCGGTTTCGGTTTTTATTTTCGTACGG | 1532 |
| 100 | | 29c6-1652RM | CACCATCCCCGCCGCCGT | 1652 |
| 101 | MSP43 | 16c6-1551FM | TTCGTACGGAGGGATGCGGCGT | 1551 |
| 102 | | 29c6-1652RM | CACCATCCCCGCCGCCGT | 1652 |
| 103 | MSP44 | 17c6-1576FM | GGGTTTCGAAGTTTCGGGCGG | 1576 |
| 104 | | 29c6-1652RM | CACCATCCCCGCCGCCGT | 1652 |
| 105 | MSP45 | 14c6-1511FM | GGACGTGTTTAGTTTCGGTTTGTCGG | 1511 |
| 106 | | 28c6-1716RM | ACCCGACGCCTCTAAACGCGA | 1716 |
| 107 | MSP46 | 15c6-1532FM | GTCGGTTTCGGTTTTTATTTTCGTACGG | 1532 |
| 108 | | 28c6-1716RM | ACCCGACGCCTCTAAACGCGA | 1716 |
| 109 | MSP47 | 16c6-1551FM | TTCGTACGGAGGGATGCGGCGT | 1551 |
| 110 | | 28c6-1716RM | ACCCGACGCCTCTAAACGCGA | 1716 |
| 111 | MSP48 | 17c6-1576FM | GGGTTTCGAAGTTTCGGGCGG | 1576 |
| 112 | | 28c6-1716RM | ACCCGACGCCTCTAAACGCGA | 1716 |
| 113 | MSP49 | 17c6-1576FM | GGGTTTCGAAGTTTCGGGCGG | 1576 |
| 114 | | 27c6-1799RM | CGAAAAACCGAACAACGAAACTCGA | 1799 |
| 115 | MSP50 | 18c6-1676FM | GTTTAGATTGAAGTGCGATTTCGCGT | 1676 |
| 116 | | 27c6-1799RM | CGAAAAACCGAACAACGAAACTCGA | 1799 |
| 117 | MSP51 | 19c6-1693FM | ATTTCGCGTTTAGAGGCGTCGG | 1693 |
| 118 | | 27c6-1799RM | CGAAAAACCGAACAACGAAACTCGA | 1799 |
| 119 | MSP52 | 18c6-1676FM | GTTTAGATTGAAGTGCGATTTCGCGT | 1676 |
| 120 | | 26c6-1806RM | CGAATTACGAAAAACCGAACAACGA | 1806 |
| 121 | MSP53 | 19c6-1693FM | ATTTCGCGTTTAGAGGCGTCGG | 1693 |
| 122 | | 26c6-1806RM | CGAATTACGAAAAACCGAACAACGA | 1806 |
| 123 | MSP54 | 18c6-1676FM | GTTTAGATTGAAGTGCGATTTCGCGT | 1676 |
| 124 | | 25c6-1852RM | CTTCCGAAAAAAAATAAAAAACGCGACCCGA | 1852 |
| 125 | MSP55 | 19c6-1693FM | ATTTCGCGTTTAGAGGCGTCGG | 1693 |
| 126 | | 25c6-1852RM | CTTCCGAAAAAAAATAAAAAACGCGACCCGA | 1852 |
| 127 | MSP56 | 20c6-1754FM | GAGTTGTTTGGCGTTTTTTCGTCGA | 1754 |
| 128 | | 25c6-1852RM | CTTCCGAAAAAAAATAAAAAACGCGACCCGA | 1852 |
| 129 | MSP57 | 19c6-1693FM | ATTTCGCGTTTAGAGGCGTCGG | 1693 |
| 130 | | 24c6-1929RM | ATATATAAATAAATAAACGAACGATTTATCGT | 1929 |
| 131 | MSP58 | 20c6-1754FM | GAGTTGTTTGGCGTTTTTTCGTCGA | 1754 |
| 132 | | 24c6-1929RM | ATATATAAATAAATAAACGAACGATTTATCGT | 1929 |

TABLE 2A-continued

C6Orf150 MSP primer sets.

| SEQ ID NO: | Primer Set | Primer Name | Primer Sequence | Position of 5' end relative to SEQ ID NOs: 1 & 2 |
|---|---|---|---|---|
| 133 | MSP59 | 21c6-1768FM | TTTTTCGTCGAGTTTCGTTGTTCGG | 1768 |
| 134 | | 24c6-1929RM | ATATATAAATAAATAAACGAACGATTTATCGT | 1929 |
| 135 | MSP60 | 22c6-1780FM | TTTCGTTGTTCGGTTTTTCGTAATTCGT | 1780 |
| 136 | | 24c6-1929RM | ATATATAAATAAATAAACGAACGATTTATCGT | 1929 |
| 137 | MSP61 | 23c6-1805FM | CGTAGTTTTTATTTTTTCGGGTCGCGT | 1805 |
| 138 | | 24c6-1929RM | ATATATAAATAAATAAACGAACGATTTATCGT | 1929 |

For MSP-8 (primer SEQ ID NOs: 31 and 32), Table 2B provides the coordinates of the 3' end of each primer relative to SEQ ID NO: 7 (and the bisulfite converted product of its methylated form, SEQ ID NO: 8), and also provides the genomic coordinates of the 5' and 3' end of each primer relative to the hg18 build of chromosome 6.

TABLE 2B

| | 5' end of the primer | | 3' end of the primer | |
|---|---|---|---|---|
| SEQ ID NO: | numbers corresponding to 4000 bp fragment | numbers corresponding to UCSC genomic sequence Human March 2006 Assembly (hg18) | numbers corresponding to 4000 bp fragment | numbers corresponding to UCSC genomic sequence Human March 2006 Assembly (hg18) |
| 31 | 1200 | 74,218,520 | 1225 | 74,218,495 |
| 32 | 1329 | 74,218,391 | 1308 | 74,218,412 |

Additionally, provided herein (Table 3, below) are primer pairs that will amplify fragments from the bisulfite converted differentially methylated region templates derived from both methylated and unmethylated forms of the domain. That is, reactions C6 (primers corresponding to SEQ ID NO: 139 and 140) and C10 (primers corresponding to SEQ ID NO: 141 and 142) will amplify corresponding fragments from the bisulfite converted form of SEQ ID NO: 7 (the sense strand) that derives from both the methylated (SEQ ID NO: 8) and unmethylated form (SEQ ID NO: 9) of SEQ ID NO: 7. Similarly, reactions C18 (primers corresponding to SEQ ID NO: 143 and 144) and C22 (primers corresponding to SEQ ID NO: 145 and 146) will amplify corresponding fragments from the bisulfite converted form of SEQ ID NO: 10 (the anti-sense strand) that derives from both methylated (SEQ ID NO: 11) and unmethylated (SEQ ID NO: 12) forms of SEQ ID NO: 10. In some instances, as indicated by the nucleotide code, the primers are degenerate to enable the primers to hybridize to either a potential methylated or a potential unmethylated cytosine residue. Primers with these properties may be used to amplify fragments whose origin from methylated versus unmethylated templates may be interrogated by sequencing ("bisulfite sequencing"), by restriction enzyme methods such as COBRA, and by digital PCR techniques such as BEAMing, as well as by other assays.

TABLE 3

Methylation insensitive primers.

| SEQ ID NO: | PCR fragment | Strand | Primer name | Primer seq | Primer 5' end location (in 4 kb SS strand seq) |
|---|---|---|---|---|---|
| 139 | c6 | SS | F3 (old) | GGATTGTTTGGAGAGTTAGAAAT | 857 |
| 140 | | | R3 (new) | ACTCCAACCCCTCTACCCCAAA | 1413 |
| 141 | c10 | SS | F4 (new) | TTGGGGYAGAGGGGTTGGAGTT | 1394 |
| 142 | | | r1 old | TCAATACCRATTAATTATCTA | 1958 |
| 143 | c18 | AS | AS F4 (new) | CRAACCCTAAAACRTACCCAA | 1501 |
| 144 | | | AS R2 (old) | AAATTYGATATATGTYGGTTTGT | 1958 |
| 145 | c22 | AS | AS F2 (old) | TCCRAAACCRAAACCACTA | 1090 |
| 146 | | | AS R5 (new) | TTTTYGTAYGAGAATGGGGGT | 1561 |

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agaro se gel. After electrophoresis, the agaro se gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TaqMan probes and molecular beacons. Quantitation may be on an absolute basis, or may be relative to a constitutively methylated DNA standard, or may be relative to an unmethylated DNA standard. In one instance the ratio of methylated C6Orf150 derived product to unmethylated derived C6Orf150 product may be constructed.

Methods for detecting methylation of the C6Orf150 DNA in this invention are not limited to MSP, and may cover any assay for detecting DNA methylation. Another example method for detecting methylation of the C6Orf150 DNA is by using "methylation-sensitive" restriction endonucleases, the methods and examples of which are disclosed in U.S. Pat. No. 7,485,420, incorporated herein in its entirety. Such methods comprise treating the genomic DNA isolated from a subject with a methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, MspI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57:808-11). No sodium bisulfite is used in this technique.

Yet another exemplary method for detecting methylation of the C6Orf150 DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the C6Orf150 DNA include the MS-SnuPE methods. This method uses compound-converted C6Orf150 DNA as a template in a primer extension reaction wherein the primers used produce a product, dependent upon whether the compound-converted template contains CpG dinucleotides or UpG dinucleotides (see e.g., Gonzalgo, et al., 1997, *Nucleic Acids Res.*, 25:2529-31).

Another exemplary method for detecting methylation of the C6Orf150 DNA is called COBRA (i.e., combined bisulfite restriction analysis). This method has been routinely used for DNA methylation detection and is well known in the art (see, e.g., Xiong, et al., 1997, *Nucleic Acids Res*, 25:2532-4).

In certain embodiments, the invention provides methods that involve directly sequencing the product resulting from an MSP reaction to determine if the compound-converted C6Orf150 template sequence contains CpG dinucleotides or UpG dinucleotides. Molecular biology techniques such as directly sequencing a PCR product are well known in the art.

In alternative embodiments, the skilled artisan will appreciate that the present invention is based in part, on the recognition that C6Orf150 may function as a tumor suppressor gene. Accordingly, in certain aspects, the invention provides assays for detecting molecular markers that distinguish between healthy cells and C6Orf150-associated diseases cells, such as colon neoplasia cells. As described above, one of the molecular markers of the present application includes methylated C6Orf150 nucleotide sequences. Thus, in one embodiment, assaying for the methylation status of the C6Orf150 nucleotide sequence can be monitored for detecting a C6Orf150-silencing associated disease.

This application further provides another molecular marker: the C6Orf150 gene expression transcript or the gene product. Thus, in another embodiment, expression of the C6Orf150 nucleic acid or protein can be monitored for detecting a C6Orf150-silencing associated disease such as a colon neoplasia.

In certain embodiments, the invention provides detection methods by assaying the above-mentioned C6Orf150 molecular markers so as to determine whether a patient has or does not have a disease condition. Further, such a disease condition may be characterized by decreased expression of C6Orf150 nucleic acid or protein described herein. In certain embodiments, the invention provides methods for determining whether a patient is or is not likely to have a C6Orf150-associated disease by detecting the expression of the C6Orf150 nucleotide sequences. In further embodiments, the invention provides methods for determining whether the patient is having a relapse or determining whether a patient's cancer is responding to treatment.

In other embodiments, the application provides method for detecting colon neoplasia. In certain embodiments, the present invention provides methods for detecting a colon neoplasia that is associated with silencing of C6Orf150 gene. Such methods comprise assaying for the presence or absence of a methylated C6Orf150 nucleotide sequence in a sample obtained from a subject. In other aspects, the invention relates to methods for determining whether a patient is likely or unlikely to have a colon cancer. In further aspects, the invention relates to methods for monitoring colon neoplasia in a subject.

In certain embodiments, the invention provides assays for detecting C6Orf150 protein or nucleic acid transcript described herein. In certain embodiments, a method of the invention comprises providing a biological sample and probing the biological sample for the C6Orf150 expression which include protein or nucleic acid transcript of the C6Orf150. Information regarding the C6Orf150 expression status, and optionally the quantitative level of the C6Orf150 expression, may then be used to draw inferences about the nature of the biological sample and, if the biological sample was obtained from a subject, the health state of the subject.

In certain embodiments, a method of the invention comprises detecting the presence of C6Orf150 protein in a sample. Optionally, the method involves obtaining a quantitative measure of the C6Orf150 protein in the sample. In view of this specification, one of skill in the art will recognize a wide range of techniques that may be employed to detect and optionally quantitate the presence of a protein. In preferred embodiments, C6Orf150 protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

In certain embodiments, a method of the invention comprises detecting the presence of a C6Orf150-expressed nucleic acid, such as an mRNA, in a sample. Optionally, the method involves obtaining a quantitative measure of the C6Orf150-expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances, detection involves an amplification as well. Northern blots, dot blots, microarrays, quantitative PCR, and quantitative RT-PCR are all well known methods for detecting a nucleic acid in a sample.

In certain embodiments, the invention provides nucleic acid probes that bind specifically to a C6Orf150 nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

Immunoscintigraphy using monoclonal antibodies directed at the C6Orf150 marker may be used to detect and/or diagnose a cancer. For example, monoclonal antibodies against the C6Orf150 marker labeled with $^{99}$Technetium, $^{111}$Indium, $^{125}$Iodine-may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In certain embodiments, the present invention provides drug screening assays for identifying test compounds which potentiate the tumor suppressor function of the C6Orf150 gene. In one aspect, the assays detect test compounds which potentiate the expression level of the C6Orf150. In another aspect, the assays detect test compounds which inhibit the methylation of the C6Orf150 nucleotide sequences. In certain embodiments, drug screening assays can be generated which detect test compounds on the basis of their ability to interfere with stability or function of the C6Orf150 polypeptide. Alternatively, simple binding assays can be used to detect compounds that inhibit or potentiate the interaction between the C6Orf150 polypeptide and its interacting protein or the binding of the C6Orf150 polypeptide to a target DNA.

A variety of assay formats may be used and, in light of the present disclosure, those not expressly described herein will nevertheless be considered to be within the purview of ordinary skill in the art. Assay formats can approximate such conditions as C6Orf150 expression level, methylation status of C6Orf150 sequence, tumor suppressing activity, intermediate filament formation activity, and may be generated in many different forms. In many embodiments, the invention provides assays including both cell-free systems and cell-based assays which utilize intact cells.

Compounds to be tested can be produced, for example, by bacteria, yeast or other organisms (e.g., natural products), produced chemically (e.g., small molecules, including peptidomimetics), or produced recombinantly. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In certain embodiments, test compounds identified from these assays may be used in a therapeutic method for treating a C6Orf150-associated proliferative disease.

Still another aspect of the application provides transgenic non-human animals which express a heterologous C6Orf150 gene, or which have had one or more genomic C6Orf150 gene(s) disrupted in at least one of the tissue or cell-types of the animal. For instance, transgenic mice that are disrupted at their C6Orf150 gene locus can be generated.

In another aspect, the application provides an animal model for a C6Orf150-associated proliferative disease, which has a mis-expressed C6Orf150 allele. For example, a mouse can be bred that has a C6Orf150 allele deleted, or in which all or part of one or more C6Orf150 exons are deleted. Such a mouse model can then be used to study disorders arising from mis-expression of the C6Orf150 gene.

Accordingly, the present application discloses transgenic animals which are comprised of cells (of that animal) containing a C6Orf150 transgene and which preferably (though optionally) express an exogenous C6Orf150 protein in one or more cells in the animal. The C6Orf150 transgene can encode the wild-type form of the protein, or can encode homologs thereof, including both agonists and antagonists, as well as antisense constructs. The C6Orf150 transgene can include a C6Orf150 nucleotide sequence (e.g., SEQ ID NO: 1) or fragments thereof. In preferred embodiments, the expression of the transgene is restricted to specific subsets of cells, tissues or developmental stages utilizing, for example, cis-acting sequences that control expression in the desired pattern.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the C6Orf150 polypeptides. For example, excision of a target sequence which interferes with the expression of a recombinant C6Orf150 gene can be designed to activate expression of that gene. This interference with expression of the protein can result from a variety of mechanisms, such as spatial separation of the C6Orf150 gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *Proc. Natl. Acad. Sci. USA* 89:6232-6236; Orban et al., (1992) *Proc. Natl. Acad. Sci. USA* 89:6861-6865) or the FLP recombinase system of *Saccharomyces cerevisiae* (O'Gorman et al., (1991) *Science* 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509-1514); catalyzing the excision of the target sequence when the loxP sequences are oriented as direct repeats and catalyzes inversion of the target sequence when loxP sequences are oriented as inverted repeats.

V. Subjects and Samples

In certain aspects, the invention relates to a subject suspected of having or has a C6Orf150-associated disease such as colon neoplasia. Alternatively, a subject may be undergoing routine screening and may not necessarily be suspected of having such a C6Orf150-associated disease or condition. In a preferred embodiment, the subject is a human subject, and the C6Orf150 associated disease is colon neoplasia.

Assaying for C6Orf150 markers discussed above in a sample from subjects not known to have a colon neoplasia can aid in diagnosis of such a colon neoplasia in the subject. To illustrate, detecting the methylation status of the C6Orf150 nucleotide sequence by MSP can be used by itself, or in combination with other various assays, to improve the sensitivity and/or specificity for detecting a colon neoplasia. Preferably, such detection is made at an early stage in the development of cancer, so that treatment is more likely to be effective.

In addition to diagnosis, assaying of a C6Orf150 marker in a sample from a subject not known to have colon neoplasia, can be prognostic for the subject (i.e., indicating the probable course of the disease). To illustrate, subjects having a predisposition to develop colon neoplasia may possess methylated C6Orf150 nucleotide sequences. Assaying of C6Orf150 markers in a sample from subjects can also be used to select a particular therapy or therapies which are particularly effective against the colon neoplasia in the subject, or to exclude therapies that are not likely to be effective.

Assaying of C6Orf150 markers in samples from subjects that are known to have, or to have had, a cancer associated with silencing of the C6Orf150 gene is also useful. For example, the present methods can be used to identify whether therapy is effective or not for certain subjects. One or more samples are taken from the same subject prior to and following therapy, and assayed for the C6Orf150 markers. A finding that the C6Orf150 marker is present in the sample taken prior to therapy and absent (or at a lower level) after therapy would indicate that the therapy is effective and need not be altered. In those cases where the C6Orf150 marker is present in the sample taken before therapy and in the sample taken after therapy, it may be desirable to alter the therapy to increase the likelihood that the cancer will be eradicated in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of a cancer associated with silencing of the C6Orf150 gene. For subjects in which a cancer is progressing, a C6Orf150 marker may be absent from some or all samples when the first sample is taken and then appear in one or more samples when the second sample is taken. For subjects in which cancer is regressing, a C6Orf150 marker may be present in one or a number of samples when the first sample is taken and then be absent in some or all of these samples when the second sample is taken.

Samples for use with the methods described herein may be essentially any biological material of interest. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immuno-compromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In certain embodiments, a bodily fluid sample is a urine sample or a colonic effluent sample. In certain embodiments, a bodily fluid sample is a stool sample.

A subject is preferably a human subject, but it is expected that the molecular markers disclosed herein, and particularly their homologs from other animals, are of similar utility in other animals. In certain embodiments, it may be possible to detect a C6Orf150 marker directly in an organism without obtaining a separate portion of biological material. In such instances, the term "sample" is intended to encompass that portion of biological material that is contacted with a reagent or device involved in the detection process.

In certain embodiments, DNA which is used as the template in an MSP reaction is obtained from a bodily fluid sample. Examples of preferred bodily fluids are blood, serum, plasma, a blood-derived fraction, stool, colonic effluent or urine. Other body fluids can also be used. Because they can be easily obtained from a subject and can be used to screen for multiple diseases, blood or blood-derived fractions are especially useful. For example, it has been shown that DNA alterations in colorectal cancer patients can be detected in the blood of subjects (Hibi, et al., 1998, Cancer Res, 58:1405-7). Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

DNA is then isolated from samples from the bodily fluids. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

VI. Therapeutic Methods for C6Orf150-Associated Diseases

Yet another aspect of this application pertains to methods of treating a C6Orf150-associated proliferative disease which arises from reduced expression or over-expression of the C6Orf150 gene in cells. Such C6Orf150-associated proliferative diseases (for example, a colon neoplasia) can result from a wide variety of pathological cell proliferative conditions. In certain embodiments, treatment of a C6Orf150-associated proliferative disorder includes modulation of the C6Orf150 gene expression or C6Orf150 activity. The term "modulate" envisions the suppression of expression of C6Orf150 when it is over-expressed, or augmentation of C6Orf150 expression when it is under-expressed.

In an embodiment, the present invention provides a therapeutic method by using a C6Orf150 gene construct as a part of a gene therapy protocol, such as to reconstitute the function of a C6Orf150 protein in a cell in which the C6Orf150 protein is mis-expressed or non-expressed. To illustrate, cell types which exhibit pathological or abnormal growth presumably depend at least in part on a function of a C6Orf150 protein. For example, gene therapy constructs encoding the C6Orf150 protein can be utilized in a colon neoplasia that is associated with silencing of the C6Orf150 gene.

In certain embodiments, the invention provides therapeutic methods using agents which induce re-expression of C6Orf150. Loss of C6Orf150 gene expression in a C6Orf150-associated diseased cell may be due at least in part to methylation of the C6Orf150 nucleotide sequence, methylation suppressive agents such as 5-deoxyazacytidine or 5-azacytidine can be introduced into the diseased cells. Other similar agents will be known to those of skill in the art. In a preferred embodiment, the C6Orf150-associated disease is colon neoplasia associated with increased methylation of C6Orf150 nucleotide sequences.

In certain embodiments, the invention provides therapeutic methods using a nucleic acid approach, for example, anti-sense nucleic acid, ribozymes or triplex agents, to block transcription or translation of a specific C6Orf150 mRNA, either by masking that mRNA with an antisense nucleic acid or triplex agent or by cleaving it with a ribozyme. Such disorders include neurodegenerative diseases, for example. Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into a target C6Orf150 over-producing cell. Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991). Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988).

The present invention also provides gene therapy for the treatment of proliferative or immunologic disorders which are mediated by C6Orf150 protein. Such therapy would achieve its therapeutic effect by introduction of the C6Orf150 antisense polynucleotide into cells having the proliferative disorder. Alternatively, it may be desirable to introduce polynucleotides encoding full-length C6Orf150 into diseased cells.

Delivery of antisense C6Orf150 polynucleotide or the C6Orf150 gene can be achieved using a recombinant expression vector such as a chimeric virus or a colloidal dispersion system. Especially preferred for therapeutic delivery of antisense sequences is the use of targeted liposomes. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a C6Orf150 sequence of interest into the viral vector, along with another gene which encodes the ligand for a receptor on a specific target cell, for example, the vector is target-specific. Retroviral vectors can be made target-specific by attaching, for example, a sugar, a glycolipid or a protein. Preferred targeting is accomplished by using an antibody to target the retroviral vector. Those skilled in the art will know of, or can readily ascertain without undue experimentation, specific polynucleotide sequences which can be inserted into the retroviral genome or attached to a viral envelope to allow target-specific delivery of the retroviral vector containing antisense C6Orf150 polynucleotide or the C6Orf150 gene.

The invention also relates to a medicament or pharmaceutical composition comprising a C6Orf150 5' flanking polynucleotide or a C6Orf150 5' flanking polynucleotide operably linked to the C6Orf150 structural gene, respectively, in a pharmaceutically acceptable excipient or medium wherein the medicament is used for therapy of C6Orf150-associated cell proliferative disorders, such as a colon neoplasia.

EXEMPLIFICATION

The invention now being generally described, it will be more readily understood by reference to the following examples, which are included merely for purposes of illustration of certain aspects and embodiments of the present invention, and are not intended to limit the invention.

Example 1

C6Orf150 is Methylated and Silenced in Colon Cancer Cell Lines

The methylation status of the C6Orf150 locus was interrogated using the technique of MCA (Methylation CpG Island Amplification) coupled to CpG island microarray (Estecio MR, et al., High-throughput methylation profiling by MCA coupled to CpG island microarray. *Genome Res* 2007, 17(10): 1529-36; Shen L, et al., Genome-wide profiling of DNA methylation reveals a class of normally methylated CpG island promoters. *PLoS Genet* 2007, 3(10):2023-36.). In this technique, methylated genomic regions are recognized by resistance to digestion with the methylation sensitive restriction enzyme SmaI. SmaI digestion resistant fragments from tumors and SmaI resistant fragments from normal control are differentially labeled with different fluorescent dyes, and are then compared by co-hybridization to microarrays.

Table 5 below shows the results of this analysis for the C6Orf150 locus. Numbers in Table 5 represent log 2 of the ratio of (methylated signal from colon cancer cell line samples) versus (normal control DNA) in hybridizing to each of the probes (shown below in Table 4, and depicted in FIG. 3 by double-headed arrows) of the C6Orf150 locus on the Agilent CpG island microarray. Data is shown from 4 C6Orf150 probes tiled on the array, 3 of which are distinct, and one of which is in duplicate. (One additional duplicated probe from this region gave no hybridzation signal). The conditions 1-4 listed in Table 5 are as follows:

TABLE 4

Probe sequence used in assay of Table 5

| Condition | Probe sequence | SEQ ID NO: |
|---|---|---|
| 1 | CAAGCAGCTCACCTTCACGTGCTCATAGTAGCTCCCGGTGTTCAG | 148 |
| 2 | CAAGCAGCTCACCTTCACGTGCTCATAGTAGCTCCCGGTGTTCAG | 148 |

TABLE 4-continued

Probe sequence used in assay of Table 5

| Condition | Probe sequence | SEQ ID NO: |
|---|---|---|
| 3 | GGTCCACAACCCCTTTCACCATCCCCGCCGCCGTGGAGATATCAT | 149 |
| 4 | ATCCCTCCGTACGAGAATGGGGGCCGAGACCGGCAGGCCGGGGCT | 150 |

The data clearly define a group of colon cancer cell line samples that in this assay show enriched methylation at the C6Orf150 locus compared to normal control, by virtue of strong positive hybridization signals. The first 27 cells lines in Table 5 (V235 through V847) all represent colon cancer cell lines known to be methylated for a reference marker (designated M samples); whereas, the last 6 cell lines in Table 5 (V863 through V9M) represent colon cancer cell lines that were known to not be methylated for a reference marker (designated U cell lines). As shown in Table 5, the average C6Orf150 region methylation signal for the cell lines that did not show methylation for a reference marker (Average of U) well exceeds that of the cell lines that did show methylation in other reference biomarkers (Average of M) for each of the probes.

Further, as illustrated in FIG. 1, samples with increased levels of C6Orf150 methylation (>1 on the log 2 scale) show markedly reduced levels of C6Orf150 transcript expression. FIG. 1 shows data on expression of C6Orf150 transcript as measured on Affymetrix Human Exon 1.0 ST Arrays (Y-axis) for colon cancer cell line samples plotted against log 2 of the MCA methylation values for these samples measured on the Agilent CpG island microarrays (X-axis).

Example 2

Methylation Across the C6Orf150 DMR Domain as Assayed by MSP

The DMR across C6Orf150 was assayed for the presence of methylation by methylation specific PCR (MSP) for a

TABLE 5

MCA Analysis for the C6Orf150 locus

| | V235 | V411 | V429 | V432 | V6 | V5 |
|---|---|---|---|---|---|---|
| Condition 1 | 5.766295 | 5.937654 | 5.066688 | 5.263061 | −0.51745 | −0.72898 |
| Condition 2 | 5.478463 | 5.631196 | 4.770736 | 4.957526 | −0.81302 | −0.13029 |
| Condition 3 | 2.474973 | 2.544094 | 2.341551 | 2.184434 | −0.32751 | 0.538152 |
| Condition 4 | 2.58766 | 3.034341 | 2.189449 | 2.259841 | −1.01713 | −1.54631 |

| | V8 | V389 | V425 | V451 | V410 | V576 |
|---|---|---|---|---|---|---|
| Condition 1 | 0.026643 | −0.15852 | −1.12158 | 3.429936 | 6.827376 | −0.02293 |
| Condition 2 | −0.30533 | −0.68344 | −0.7317 | 3.479221 | 6.353291 | −0.30606 |
| Condition 3 | −0.48588 | 0.077664 | −0.27649 | 1.793429 | 4.388959 | −0.38912 |
| Condition 4 | −0.96481 | −1.21589 | −1.39714 | 0.80971 | 3.530222 | −1.18912 |

| | V10M | V456 | V784 | V503 | V478 | V400 |
|---|---|---|---|---|---|---|
| Condition 1 | −0.41009 | 6.076171 | 4.195319 | 5.917341 | 5.388252 | 0.563192 |
| Condition 2 | −0.18417 | 5.531691 | 3.631191 | 5.724736 | 5.421879 | 0.559425 |
| Condition 3 | −0.45653 | 2.960035 | 1.51722 | 3.011266 | 3.121367 | −0.11412 |
| Condition 4 | −1.19828 | 2.330251 | 0.880579 | 2.879468 | 2.26257 | −0.97252 |

| | V241 | V481 | V531 | V441 | V670 | V855 |
|---|---|---|---|---|---|---|
| Condition 1 | 5.398955 | 6.189827 | 2.713127 | −0.33179 | 5.828247 | −0.03739 |
| Condition 2 | 5.399818 | 5.988393 | 2.564101 | −0.11476 | 5.379701 | −0.02754 |
| Condition 3 | 3.137583 | 3.604857 | 0.760726 | −0.13463 | 3.476779 | −0.02809 |
| Condition 4 | 2.586142 | 3.06056 | 0.20981 | −1.27902 | 3.518182 | −1.14534 |

| | V866 | V838 | V847 | Avg. of M | V863 | V489 |
|---|---|---|---|---|---|---|
| Condition 1 | −0.41603 | 1.062859 | 0.224465 | 2.67 | 6.575967 | 7.33746 |
| Condition 2 | −0.15461 | 0.888079 | 0.090925 | 2.53 | 6.247086 | 6.958165 |
| Condition 3 | −0.15046 | 0.372386 | −0.25331 | 1.32 | 4.2557 | 3.876392 |
| Condition 4 | −1.14175 | −0.89709 | −0.95453 | 0.64 | 4.18082 | 3.911198 |

Figure 5:
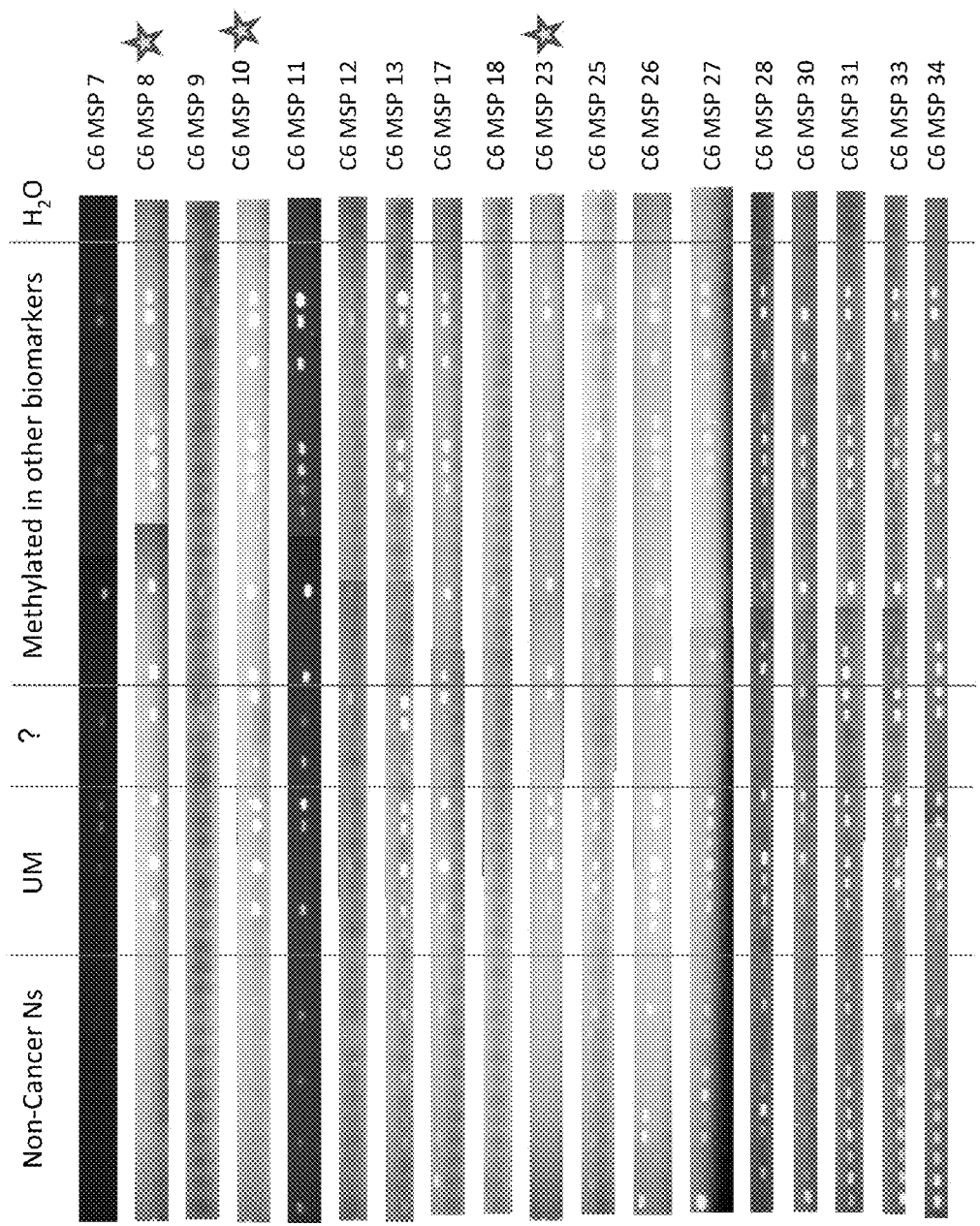
FIG. 5. Illustrates an assay for presence of methylation across the C6Orf150 differentially methylated region (DMR) by methylation specific PCR (MSP) for a representative subset of methylation specific PCR assays.
Figure 7:
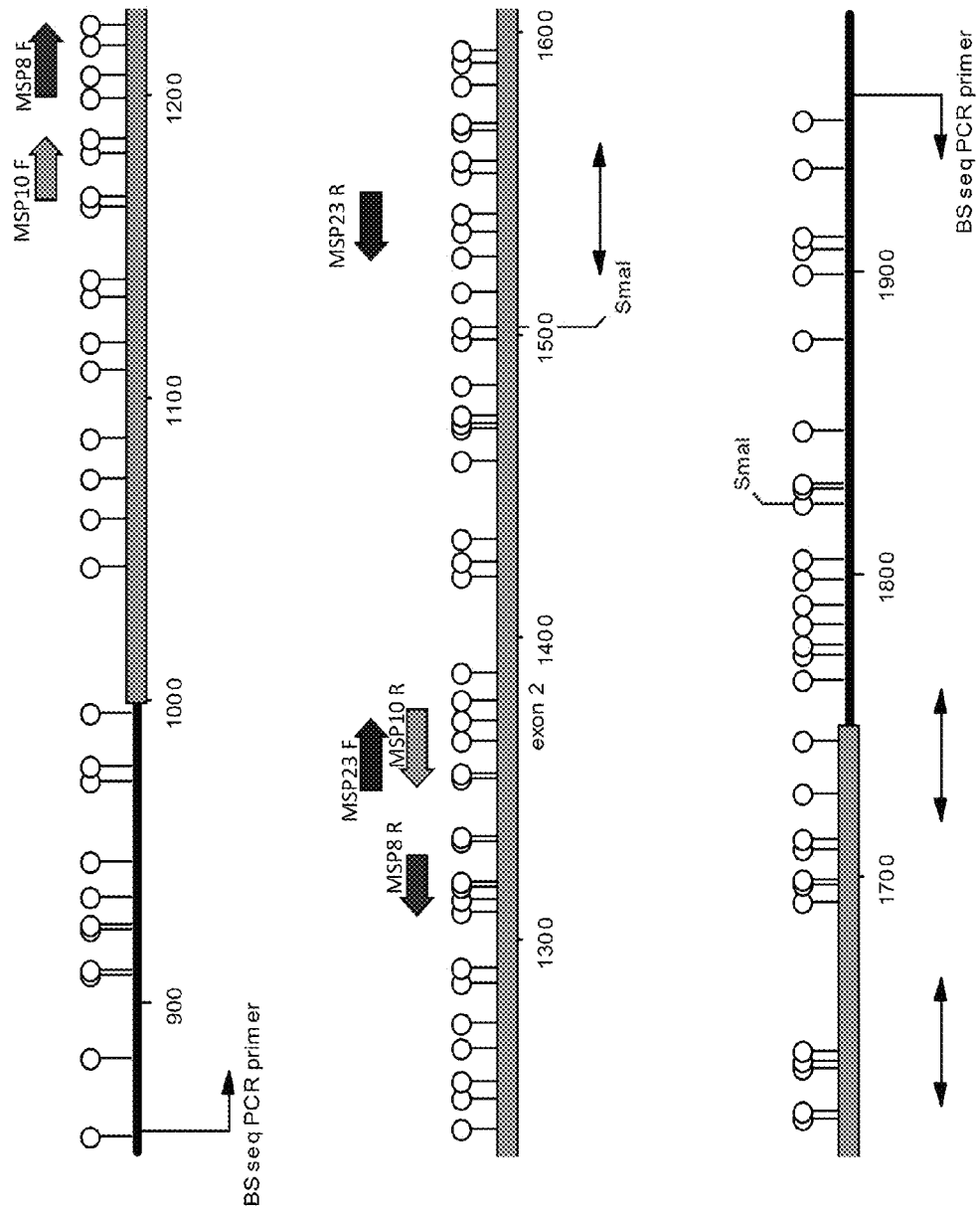
FIG. 7. Illustrates positions of primers MSP-8, MSP-10, and MSP-23 against DMR of C6Orf150. See FIG. 3 for designations.
Figure 8:
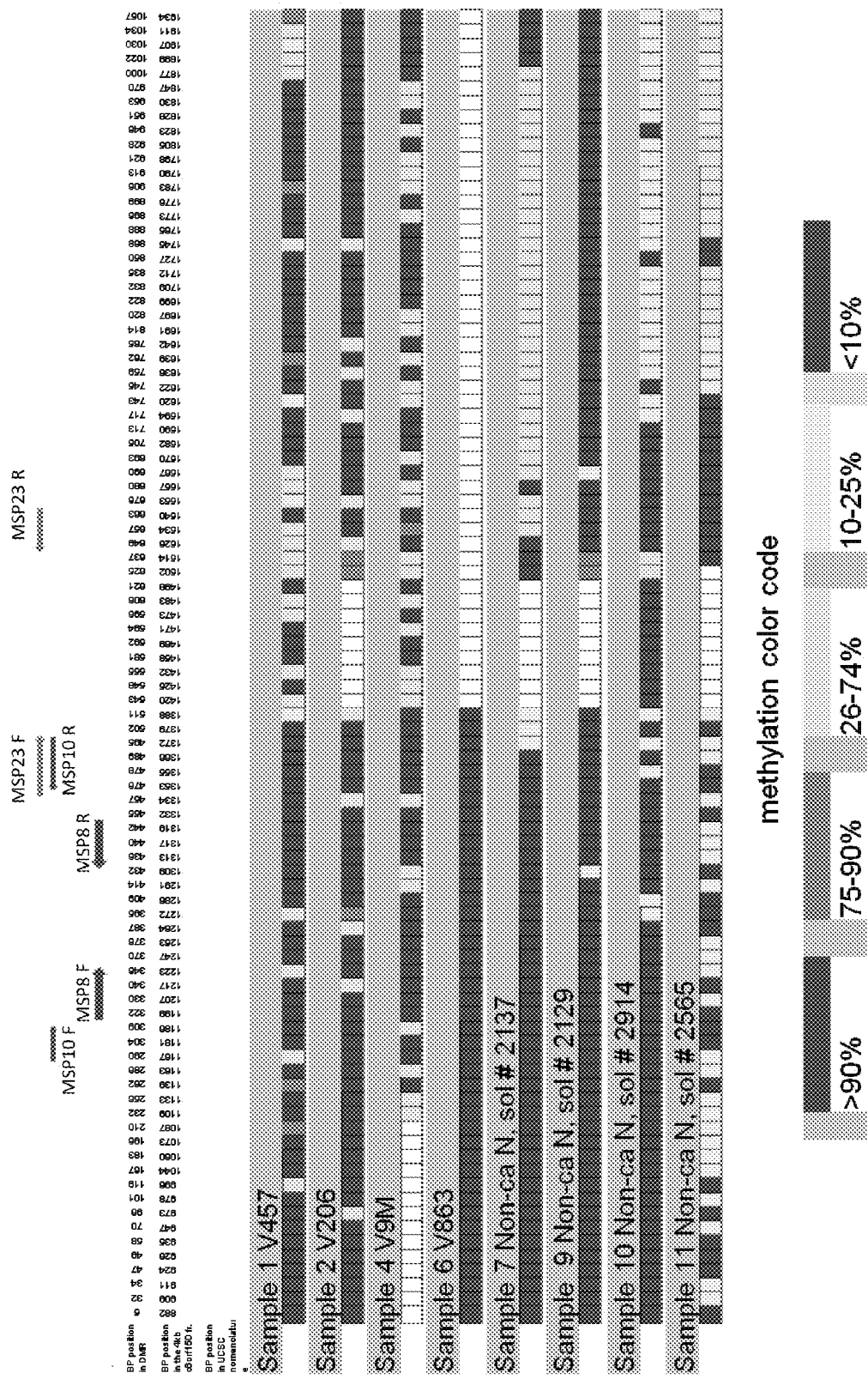
FIG. 8. Illustrates positions of primers for C6Orf150 reactions MSP8, MSP10 and MSP23 referenced to the results of bisulfite sequencing of the C6Orf150 differentially methylated region (DMR) as shown on FIG. 5.

| | V9p | V206 | V457 | V9M | Avg. of U | |
|---|---|---|---|---|---|---|
| Condition 1 | 6.946206 | 6.473107 | 6.581563 | 5.066088 | 6.5 | |
| Condition 2 | 6.655866 | 6.257684 | 6.357064 | 4.943032 | 6.24 | |
| Condition 3 | 3.651807 | 3.880467 | 4.052071 | 2.325461 | 3.67 | |
| Condition 4 | 3.761348 | 3.427567 | 3.74945 | 2.438404 | 3.58 | | representative subset of methylation specific PCR assays. Samples interrogated include normal colon tissues from patients who do not have colon cancer (Non-Cancer Ns), colon cancer tumors that are unmethyated in other reference colon cancer biomarkers ("UM"), colon cancer tumors that are ambiguous for methylation in other reference colon cancer biomarkers ("?"), and colon cancers that have been shown to be methylated in other biomarkers ("Methylated in other biomarkers"). As shown on FIG. 5, it is obvious that these MSP assays detect much more methylation within the C6Orf150 differentially methylated domain in cancers than in normal tissues. Of particular interest are MSP reactions MSP8, MSP10, and MSP23. These reactions do not detect any methylation within normal colon tissues, but do detect methylation in a subset of colon cancers, including colon cancers that do not show methylation for other colon cancer biomarkers. A representative MSP reaction condition is illustrated in FIG. 6 for MSP8. FIG. 7 shows the positions of primers for MSP-8, MSP-10, and MSP-23 referenced to the schematic of the C6Orf150 locus (the designations are the same as figure legend for FIG. 3). Additionally, FIG. 8 shows the positions of primers for C6Orf150 reactions MSP8, MSP10 and MSP23 referenced to the results of bisulfite sequencing of the C6Orf150 differentially methylated domain (as shown on FIG. 3).

Example 3

Methylation at the MSP8 Target Region is Sensitive and Specific to Colon Cancer

Figure 9:
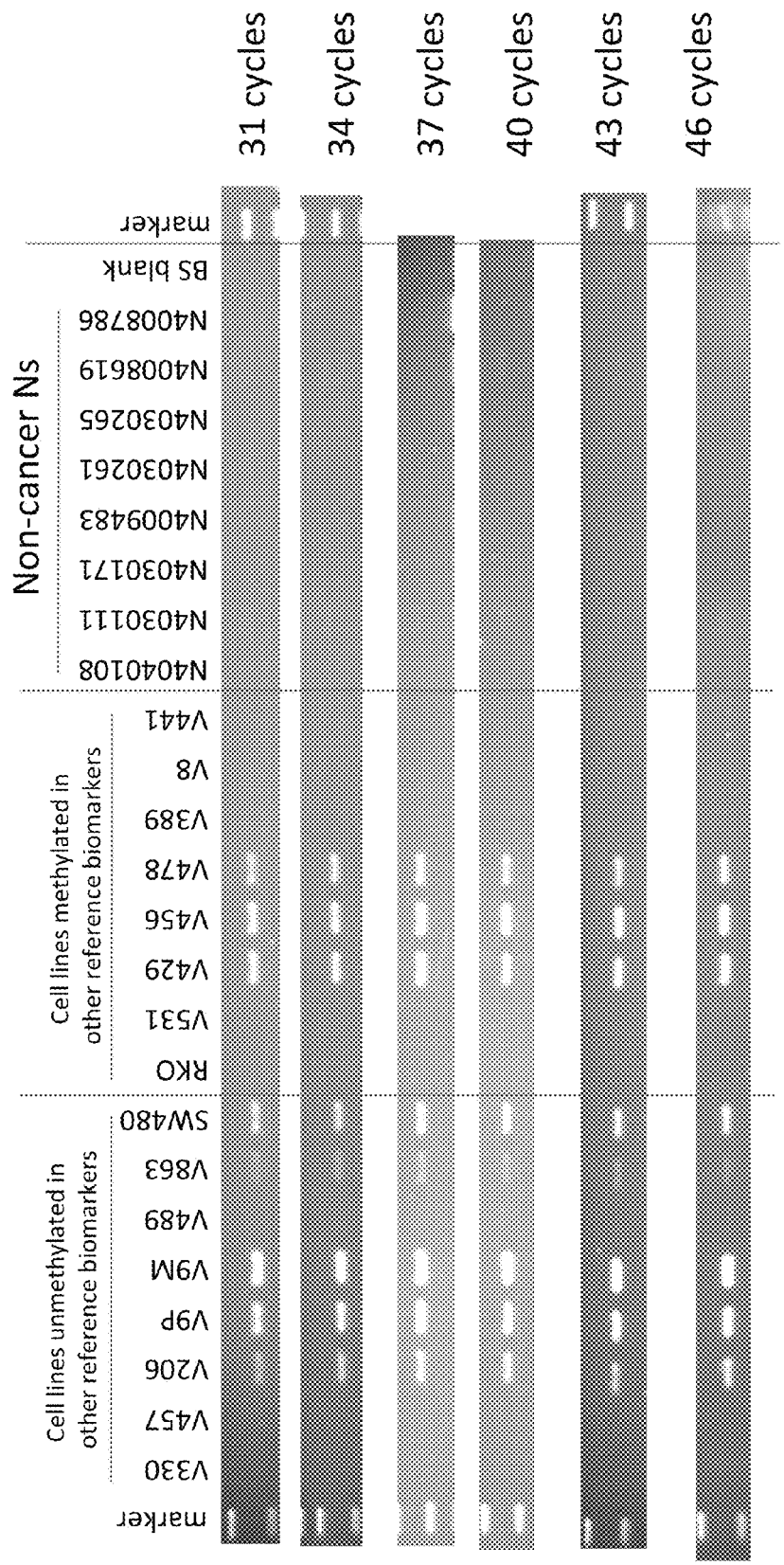
FIG. 9. C6orf150 MSP8 specificity testing demonstrating that colon cancer samples with positive MSP8 assays for C6Orf150 methylation turn positive by at least as early as PCR cycle 31. In contrast, normal colon samples remain negative in the assay for as late as at least PCR cycle number 46.
Figure 10:
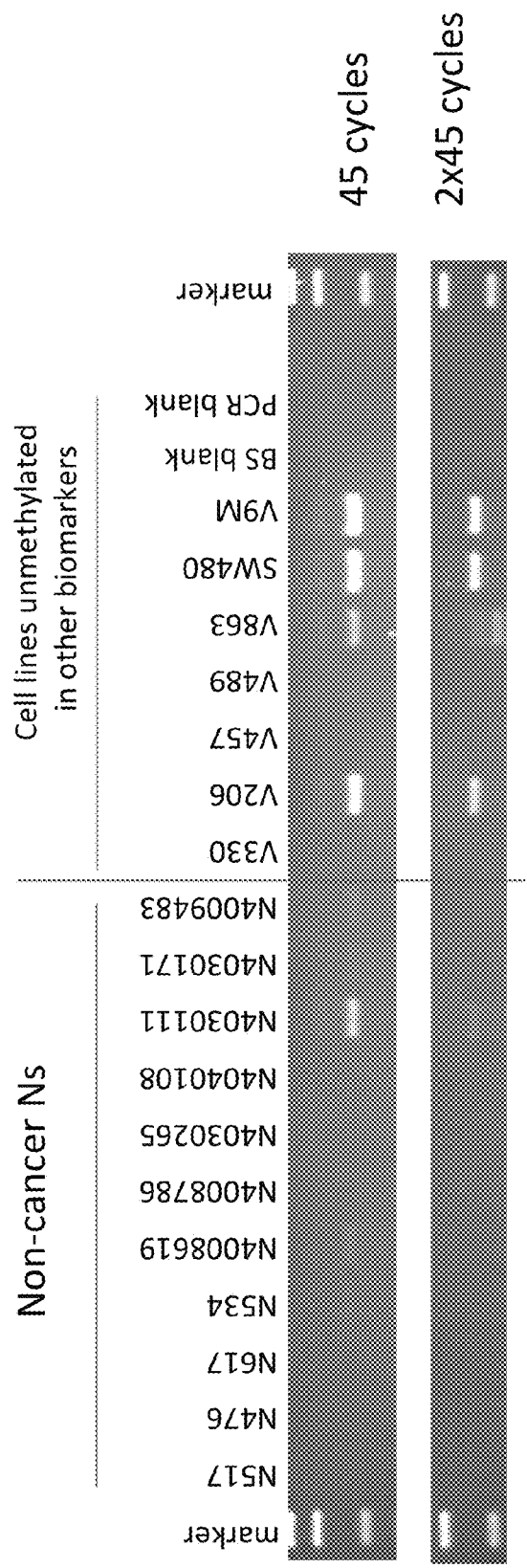
FIG. 10. C6orf150 MSP8 specificity testing demonstrating that methylation at the MSP8 target region is essentially undetectable in the great majority of normal colon tissues.

As shown in FIG. 9, colon cancer samples with positive MSP8 assays for C6Orf150 methylation turn positive by at least as early as PCR cycle 31. In contrast, normal colon samples remain negative in the assay for as late as at least PCR cycle number 46. FIG. 10 shows assay of 90 cycles of nested PCR for MSP8 (done by repeat PCR for 45 cycles of an aliquot taken from an initial 45 cycle PCR reaction). 90 cycles of nested PCR for MSP8 turns only 1 normal colon sample positive. Therefore, methylation at the MSP8 target region is essentially undetectable in the great majority of normal colon tissues.

FIG. 11 summarizes the results of C6Orf150 MSP8 testing of a panel of colon cancer cell lines used in the initial array study, and a panel of normal mucosa from 13 individuals without cancer (non-cancer normals), plus a validation set of 154 colon cancer tumor tissues of known Dukes clinical stage and colon cancer xenografts, plus normal colon mucosa from 16 individuals with colon cancer. 27% of cancer samples in the validation set tested positive for the MSP8 reaction, including 26% of the early stage Dukes B samples. None of the 16 normal colon tissues tested positive. Additionally, 41% of the cell lines initially used for C6Orf150 discovery by MCA also tested positive by MSP8.

Figure 12:
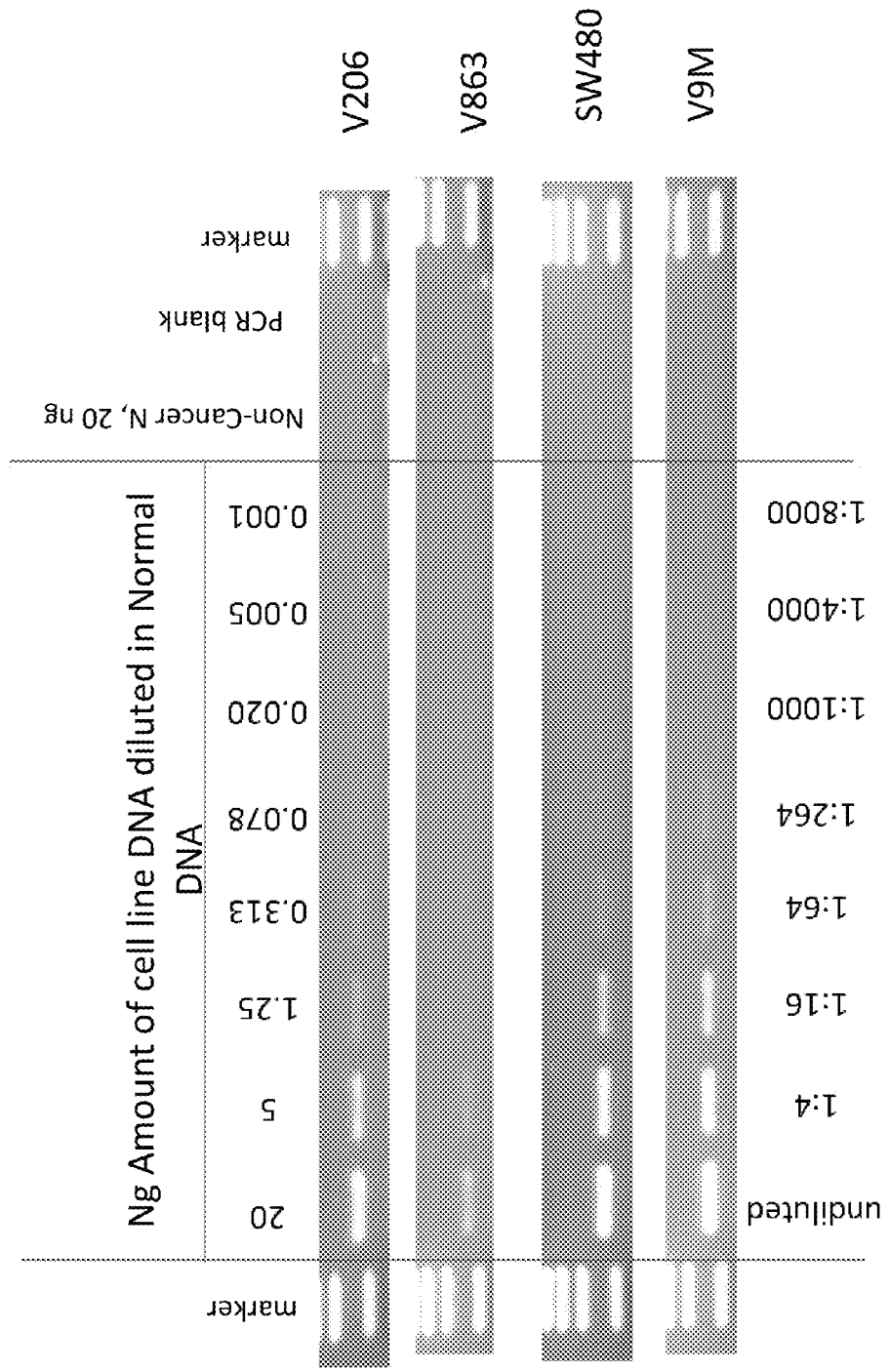
FIG. 12. MSP8 assay of serial dilutions of colon cancer sample DNAs into control normal DNA. MSP8 is able to detect between 78-313 picogram of total colon cancer genomic DNA diluted in up to 264 fold excess of normal DNA.

FIG. 12 shows MSP8 assay of serial dilutions of colon cancer sample DNAs into control normal DNA. Dilutions were done in a tube with 20 ng of total DNA. MSP8 is able to detect between 78-313 picogram of total colon cancer genomic DNA diluted in up to 264 fold excess of normal DNA.

Figure 13A:
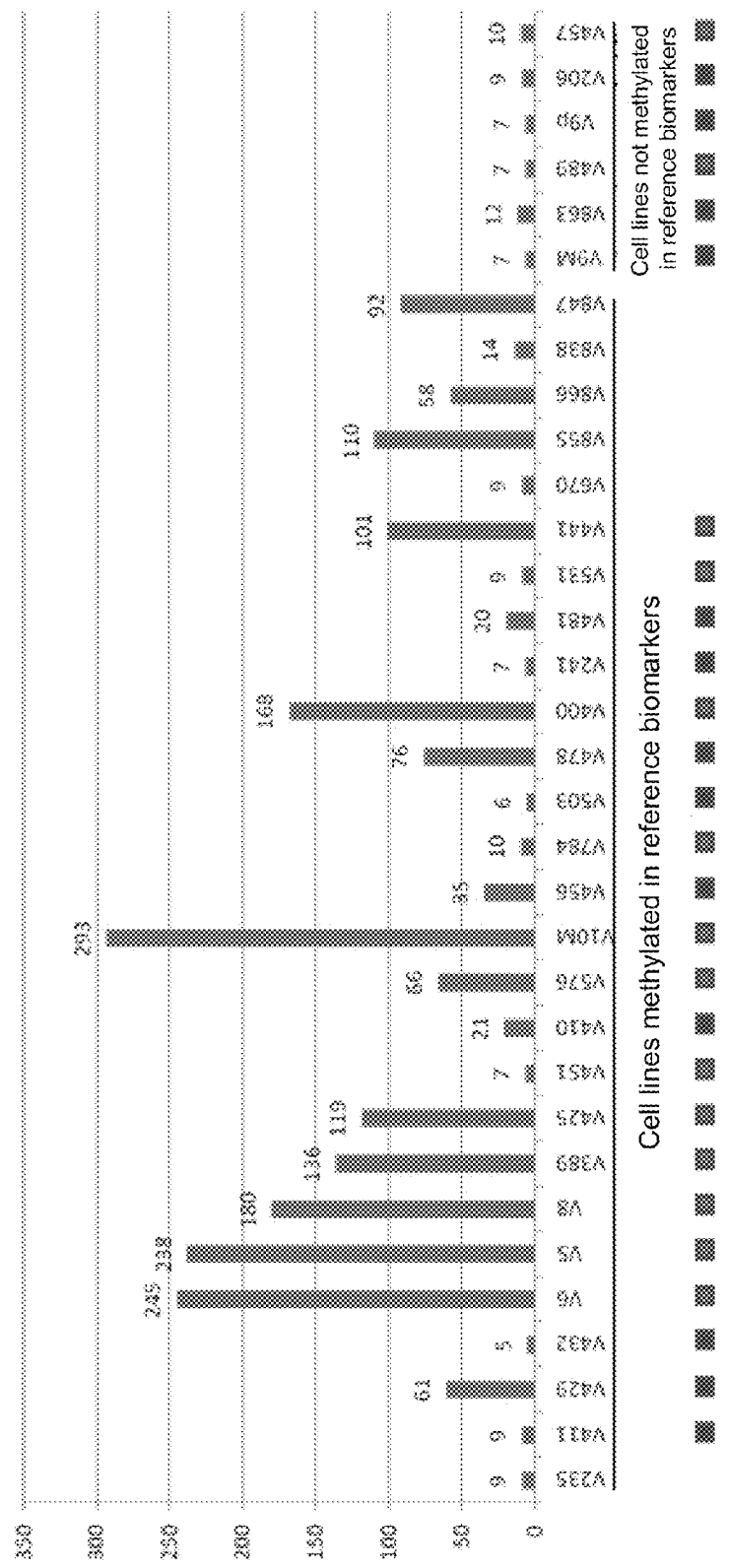
FIGS. 13A and 13B. Illustrates samples that are methylated in the MSP8 assay. Methylated samples in general demonstrate lower levels of C6Orf150 expression than unmethylated samples.
Figure 13B:
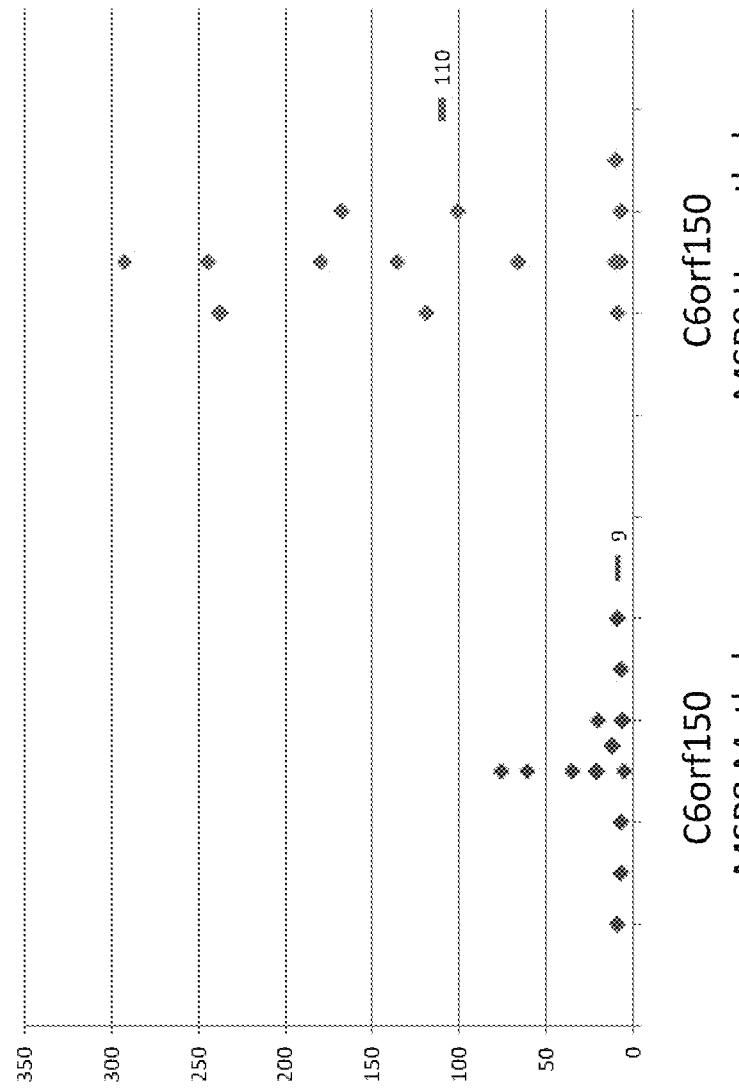

FIG. 13A shows expression of C6Orf150 in colon cancer cell line samples as assayed on the Affymetrix human all exon microarray. Color coded boxes indicate samples that are methylated in the C6Orf150 MSP8 assay (red) versus those that are not (green) by MSP8 assay. It is evident that methylated samples in general demonstrate lower levels of C6Orf150 expression than unmethylated samples. FIG. 13B displays on a scatter plot the data on C6Orf150 expression in samples methylated at C6Orf150 (as assayed by MSP8) versus those that are not methylated.

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

Sequence Information

In the following sequences, where applicable, DNA bases are denoted as follows according to IUPAC nomenclature for incompletely specified bases in nucleic acid sequences (see also http://www.chem.qmul.ac.uk/iubmb/misc/naseq.html). All sequences are indicated 5' to 3', unless noted otherwise.

| Bases | Symbol |
|---|---|
| Guanine, adenine, thymine, cytosine | G, A, T, C |
| Purine (adenine or guanine) | R |
| Pyrimidine (thymine or cytosine) | Y |
| Adenine or thymine | W |
| Guanine or cytosine | S |
| Adenine or cytosine | M |
| Guanine or thymine | K |
| Adenine or thymine or cytosine | H |
| Guanine or cytosine or thymine | B |
| Guanine or adenine or cytosine | V |
| Guanine or adenine or thymine | D |
| Guanine or adenine or thymine or cytosine | N |

SEQ ID NO: 1

The genomic sequence of the genomic minus (−) strand, depicted 5' to 3', which corresponds to the C6Orf150 sense strand relative to the C6Orf150 mRNA sequence. This 1-4000 bp of the sequence correspond to (hg18) coordinates 74,219,719-74,215,720. The yellow highlighted region in FIGS. 14A and 14B corresponds to the C6Orf150 Differentially Methylated Region (DMR; italicized below). The bolded and double-underlined bases (GGATTGCCTGGAGAGTTAGAAAC (SEQ ID NO: 151) and CAGACAACCAACCGGTACTGA (SEQ ID NO: 152)) correspond to the locations of outer flanking primers used to amplify the differentially methylated region following bisulfite conversion of unmethylated cytosine bases to uracil. The italicized, unbolded, and double-underlined bases ( *GAGTCTCCGGCTGCCCCCGAGGCCGC* (SEQ ID NO: 153) and *CCGCCCGTCCGCGCAACTGGGG* (SEQ ID NO: 154)) correspond to the locations of primers that amplify up the MSP-8 target region domain following bisulfite conversion.

(SEQ ID NO: 1)
AGATTGCGCCCCCCTAACTCAAACCAAAATTAAATTTAAAAAAACTTTCA

CTTGAAAGAGAAAAGTTTCTCTGTCAATGTTTTTGTTTTGTTTTGTTTTG

-continued

TTTTGTGATGGACTCTTTTTCTGTTGCCCAGGCTGGAGTGCAGTGGCGCG

ATCTCGGCTCACTGCAACCTCTGCCTCCCGGGTTCAAGCAGTTCTCTGTC

TCGGCCTCCCGAGTAGATGGGACTACAGGCGCCACCAAGCCCGGCTAATT

TTTTGTATTTTTAGTAGAGACGGGGTTTCACCATGTTGGCCAGGAAGGTC

TCGATGTCTTGGCCTCGTGATCCGCCCGCCTCGGCCTCCCAAACTGCTGA

GATTACAGGCGTGAGCCACCACGCCTGGCCTCTTTTTCTTTTTTGAGACA

GAGTCTCGCTCTGTCGCCCAGGCTGGAGTGAAGTGGCACGTCTCAGCTCA

CTGCAACCTCCRCCTCCCGGGTTCAAGTGATTCTCCAGCCTCAGCCTCCC

GAGTAGCTGGGATTACAGGTGCCCGCCACCACGCCTAGCTAATATTTGTA

TTTTTTAGTAGAGACGGGGTTTCTTTCGCCTTGTTGGCCAGGCTGGTCTT

GAACTCCTGACCTCAGGTGATCCGCCCACCTCGGTCTCCCAGATTGCTGG

GATTACAGGCGTGAGTCAGTGTGCCCAGGCAACACACACACACACATATA

TTTAATTATAAGAAAGACCAGGTCTTGCTGGGTTGCCCAGGCTGGTCTCA

AACTCCTGAGCTCAAGCGACCCGCCTGCCTCGGCCTCTCGGATGCTGAGG

TTACAGGCGTGAGCCACCGCGCCCGGCCCTACCTCATCTTCTTAAGACAG

GGGCACGGATTGCCTGGAGAGTTAGAAAC*TTCGAGACTTTTGTAGCCTCA*

*GGAAAGGCCGCGGCCAGCCTCTTCGCGGCATGGGCGTGGCTCCCAGCGAC*

*TTCCCAGCCTGGGGTTCCCCTTCGGGTCGCAGACTCTTGTGTGCCCGCCA*

*GTAGTGCTTGGTTTCCAACAGCTGCTGCTGGCTCTTCCTCTTGCGGCCTT*

*TTCCTGAAACGGATTCTTCTTTCGGGGAACAGAAAGCGCCAGCCATGCAG*

*CCTTGGCACGGAAAGGCCRTGCAGAGAGCTTCCGAGGCCGGAGCCACTGC*

*CCCCAAGGCTTCCGCACGGAATGCCAGGGGCGCCCCGATGGATCCCAMC*

GAGTCTCCGGCTGCCCCCGAGGCCGCCCTGCCTAAGGMGGGAAAGTTCGG

*CCCCGCCAGRAAGTCGGGATCCCGGCAGAAAAAGAGCGCCCCGGACACCC*

*AGGAGAGG*CCGCCCGTCCGCGCAACTGGGG*CCCGCGCCAAAAAGGCCCCT*

*CAGCGCGCCCAGGACACGCAGCCGTCTGACGCCACCAGCGCCCCTGGGGC*

*AGAGGGGCTGGAGCCTCCTGCGGCTCGGGAGCCGGCTCTTTCCAGGGCTG*

*GTTCTTGCCGCCAGAGGGGCGCGCGCTGCTCCACGAAGCCAAGACCYCCG*

*CCCCGGGCCCTGGGACGTGCCCAGCCCCGGCCTGCCGGTCTCGGCCCCCAT*

*TCTCGTACGGAGGGATGCGGCGCCTGGGGCCTCGAAGCTCCGGGCGGTTT*

*TGGAGAAGTTGAAGCTCAGCCGCGATGATATCTCCACGGCGGCGGGGATG*

*GTGAAAGGGGTTGTGGACCACCTGCTGCTCAGACTGAAGTGCGACTCCGC*

*GTTCAGAGGCGTCGGGCTGCTGAACACCGGGAGCTACTATGAGCACGTGA*

*AGGTGAGCTGCTTGGCGCCCTCCCGCCGAGCCCCGCTGCTCGGCCTTCCG*

*CAATCCGCAGTCCCTACCTTCCCCGGGTCGCGCCCCTCACTTCCCTTCGG*

*AAGTAACTTAGACTTTTGCATGTTTTCGGTAGCCTAGTCTAAGTAAAAC*

*GACAAACCGTTCGTTTATTCATCTACACATCCAACGAT*CAGACAACCAAC

CGGTACTGA*TTGCTGGCTAATTTCAAGACACTGCTCCCGGGGGAATTCAA*

*ATGTATGGGTTCATTCATGCAAGCCGACATGTATCGAGTTTCCGTAACAG*

*GGCAGTGTTTGATGGTGTGGACCTGAGGTCCCGAGTCAGATATTGACTTG*

-continued

GATAATTTGAAGTGGTCTGTTAAAAATTCCACGTAGACTTTTTCCTATGA

GGAAGACCTCTTACTCCATAGAAAAAAAGATCTTCAGTTTCTCTCCCCCT

CTTCCTCCCTGCCCCCTCTCCTGCTATCCCGTCTGACCCCAATTTCTTTT

TTTTCTTTTTTCTTTTCTTTTCTTTTTTTTTTTTTGAGGCGGAGTCTC

GCTGCGTCCCCCAGGCTGGAGTGCAGTGGCGCTATCTCGGCTCACTGCAA

GCTCCGCCTCCCGGGTTCACGCCATTCTCCTGCCTCAGCTTCCCGAGTAG

CTGGGACTACAGGCGCCCGCCACCATGCCCGGCTAATTTTTTTGTATTT

TTAGTAGAGACGGTGTTTCACCGTGTTAGCCAGGATGGTCTCGATCTCCT

GACCTCTTGATTCGCTCGTCTCGGCCTCTCAAAGTGCTGGGATTACAGGC

GTSAGCTACCGCGCCCGGCCGTCTGTCCCCAGTTTCTTACACAGAAATCA

TGGGAAGCTTACAGTATAATGTTAAACAAACAAATAAGAATATCTCCTAC

AGATACTAAAACGCTTTCTAGATACACATTCCGTATAATTGCTTCGACGT

GTGTATTACACAGCTCCATTTGCTTGTGGGTGATTGAGTCATTAATCATT

CCTGTGTAAATTGAAAGTTTAGAAGCAGGTTCCTGACTGGAGCGTGTTTC

TTGCCCAGCAAGAGATTTGTTTCTTTTTCTTTTTCTTTCTTTCTTTCTTT

TTTTTTTTTTTGAGACGGAGTTTCGCTCTTGTTACCCAGGCTGGAGTGCA

ATGGCGCGATCTCAGCTCACCTCAACCTCCACCTCCCAGGTTCAAGCGAT

TCTCCTGTCTCAGCCTCCTGAGTAGATGGGATTACAAGCATGAGCCTCCA

CCCTGGCTAATTTTGTATTTTTAGTAGAGACGGGCTTTCTCCATGTTGGT

CAGGCTGGTCTAGAACTCCCGACCTCAGGTGATCTGCCAGCCTCAGCCTC

CCAAAGTGCTGGGATTACAGGCGTGAGCCACCACACCCGGCTTCTTTTCT

CTTCTTTTTTCTCTTCTCTTCTCTTCTCTATCTCTCTGTCTCTCTCTT

TTCCTCCCTCCCTCTCTTCCTCTCTCTCTCTCTCTCTTTATTTTGTTCTT

TCTTTCTTTTCTTTCTTTCTTTCTTTTTTTGATGGAGTTTCACTCTTG

TTGCCCAGGCTGTAGTGCAGTGGTGCCATCTAGGTTTCGCTGCAACCTCC

GGCTTCCAGGTTCAAGCGATTCTCCWGCTTCAGCCTTCCAAATAGCAGGG

ATTACAGGTGCCTGCCCCACTCCCGGCTAATTTATGTATTTTTAGTAGA

GACGGGGTTTCACCATGTTGGCCAGGCTGGTCTCGAACTCTGACCTCAGA

TGATCCACCTGCCTCGGCCTCCCTAAGTGCTGGGATTACAGGCTTGAGCC

ACGGCACCCAGCCCAGACTGTGTCTTGAGCATGATTCTTTTTAATTAACT

AATTTACTTTTCAGCATCAGATATGTCTCTGATTGAGCATGATTCTTATT

ATGTAAGTATCAATTCAGTTCAATTACTGTATATGGCGGGTCCAAAGGAA

AAAGAAAGTTACTAGTTAGAATTAGAGAACAAGACATTCAGAAGACAGTC

TCCATTCAGAACCACTTTGTGTGTGTGTGTGTGTGTGTGTGTGTGTGT

TTGAGACAGAGTCTCACTCTGTCACCCAGGCTGGAGTGCAGTGGCGCGAT

CTCGGCTCACTGCAAGCCCTGCCTACTGGGTTCACACCATTCTCCTGCCT

CAGCCTCCCAAGTAGCTGGGACTACAGGCGCCCGCCACCATGCCCAGCTA

ATTTTTGTATTTTTAGTAGAGACGGGGTTTCACCGTGTTAGCCAGGCTGG

T

SEQ ID NO: 2

Corresponds to a fully methylated version of SEQ ID NO: 1 (i.e. in which each cytosine at a CpG dinucleotide is methylated) following sodium bisulfite conversion of all unmethylated cytosines to uracil. (Polymorphic bases are denoted with the symbol of their unconverted polymorphism). Conventions with respect to bolded, italicized, and underlined bases are maintained from SEQ ID NO: 1 as set forth above and throughout.

(SEQ ID NO: 2)
AGATTGCGTTTTTTAATTTAAATTAAAATTAAATTTAAAAAAATTTTTA

TTTGAAAGAGAAAAGTTTTTTTGTTAATGTTTTTGTTTTGTTTTGTTTTG

TTTTGTGATGGATTTTTTTTTGTTGTTTAGGTTGGAGTGTAGTGGCGCG

ATTTCGGTTTATTGTAATTTTTGTTTTTCGGGTTTAAGTAGTTTTTTGTT

TCGGTTTTTCGAGTAGATGGGATTATAGGCGTTATTAAGTTCGGTTAATT

TTTTGTATTTTTAGTAGAGACGGGGTTTTATTATGTTGGTTAGGAAGGTT

TCGATGTTTTGGTTTCGTGATTCGTTCGTTTCGGTTTTTAAATTGTTGA

GATTATAGGCGTGAGTTATTACGTTTGGTTTTTTTTTTTTTTGAGATA

GAGTTTCGTTTTGTCGTTTAGGTTGGAGTGAAGTGGTACGTTTTAGTTTA

TTGTAATTTTTRTTTTTCGGGTTTAAGTGATTTTTTAGTTTTAGTTTTTC

GAGTAGTTGGGATTATAGGTGTTCGTTATTACGTTTAGTTAATATTTGTA

TTTTTTAGTAGAGACGGGGTTTTTTTCGTTTTGTTGGTTAGGTTGGTTTT

GAATTTTTGATTTAGGTGATTCGTTTATTTCGGTTTTTTAGATTGTTGG

GATTATAGGCGTGAGTTAGTGTGTTTAGGTAATATATATATATATATATA

TTTAATTATAAGAAAGATTAGGTTTTGTTGGGTTGTTTAGGTTGGTTTTA

AATTTTTGAGTTTAAGCGATTCGTTTGTTTCGGTTTTTCGGATGTTGAGG

TTATAGGCGTGAGTTATCGCGTTCGGTTTTATTTTATTTTTTAAGATAG

GGGTACGGATTGTTTGGA<u>GAGTTAGAAAT</u>_TTCGAGATTTTTGTAGTTTTA_

_GGAAAGGTCGCGGTTAGTTTTTTCGCGGTATGGGCGTGGTTTTTAGCGAT_

_TTTTTAGTTTGGGGTTTTTTTTCGGGTCGTAGATTTTTGTGTGTTCGTTA_

_GTAGTGTTTGGTTTTAATAGTTGTTGTTGGTTTTTTTTTTGCGGTTTT_

_TTTTTGAAACGGATTTTTTTTCGGGGAATAGAAAGCGTTAGTTATGTAG_

_TTTTGGTACGGAAAGGTTRTGTAGAGAGTTTTCGAGGTCGGAGTTATTGT_

_TTTTAAGGTTTTCGTACGGAATGTTAGGGGCGTTTCGATGGATTTTAMC_

<u>_GAGTTTTCGGTTGTTTCGAGGTCGT_</u>_TTTGTTTAAGGMGGGAAAGTTCGG_

_TTTCGTTAGRAAGTCGGGATTTCGGTAGAAAAAGAGCGTTTCGGATATTT_

_AGGAGAGG_<u>_TCGTTCGTTCGCGTAATTGGGG_</u>_TTCGCGTTAAAAAGGTTTTT_

_TAGCGCGTTTAGGATACGTAGTCGTTTGACGTTATTAGCGTTTTTGGGGT_

_AGAGGGGTTGGAGTTTTTTGCGGTTCGGGAGTCGGTTTTTTTAGGGTTG_

_GTTTTTGTCGTTAGAGGGGCGCGCGTTGTTTTACGAAGTTAAGATTCTCG_

_TTCGGGTTTTGGGACGTGTTTAGTTTCGGTTTGTCGGTTTCGGTTTTTAT_

_TTTCGTACGGAGGGATGCGGCGTTTGGGGTTTCGAAGTTTCGGGCGGTTT_

_TGGAGAAGTTGAAGTTTAGTCGCGATGATATTTTACGGCGGCGGGGATG_

_GTGAAAGGGGTTGTGGATTATTTGTTGTTTAGATTGAAGTGCGATTTCGC_

_GTTTAGAGGCGTCGGGTTGTTGAATATCGGGAGTTATTATGAGTACGTGA_

_AGGTGAGTTGTTTGGCGTTTTTTCGTCGAGTTTCGTTGTTCGGTTTTTCG_

_TAATTCGTAGTTTTTATTTTTTCGGGTCGCGTTTTTTATTTTTTTCGG_

_AAGTAATTTAGATTTTTGTATGTTTTTCGGTAGTTTAGTTTAAGTAAAAC_

_GATAAATCGTTCGTTTATTTATTTATATATTTAACGAT_<u>TAGATAATTAAT</u>

<u>CGGTATTGA</u>TTGTTGGTTAATTTTAAGATATTGTTTTCGGGGGAATTTAA

ATGTATGGGTTTATTTATGTAAGTCGATATGTATCGAGTTTTCGTAATAG

GGTAGTGTTTGATGGTGTGGATTTGAGGTTTCGAGTTAGATATTGATTTG

GATAATTTGAAGTGGTTTGTTAAAAATTTTACGTAGATTTTTTTTATGA

GGAAGATTTTTATTTTATAGAAAAAAAGATTTTTAGTTTTTTTTTTTTT

TTTTTTTTTTGTTTTTTTTTTGTTATTTCGTTTGATTTTAATTTTTTTT

TTTTTTTTTTTTTTTTTTTTTTTTTTTTTTTTGAGGCGGAGTTTC

GTTGCGTTTTTAGGTTGGAGTGTAGTGGCGTTATTTCGGTTTATTGTAA

GTTTCGTTTTCGGGTTTACGTTATTTTTTGTTTTAGTTTTTCGAGTAG

TTGGGATTATAGGCGTTCGTTATTATGTTCGGTTAATTTTTTTTGTATTT

TTAGTAGAGACGGTGTTTTATCGTGTTAGTTAGGATGGTTTCGATTTTTT

GATTTTTTGATTCGTTCGTTTCGGTTTTTAAAGTGTTGGGATTATAGGC

GTSAGTTATCGCGTTCGGTCGTTTGTTTTAGTTTTTTATATAGAAATTA

TGGGAAGTTTATAGTATAATGTTAAATAAATAAATAAGAATATTTTTAT

AGATATTAAAACGTTTTTTAGATATATATTTCGTATAATTGTTTCGACGT

GTGTATTATAGTTTTATTTGTTTGTGGGTGATTGAGTTATTAATTATT

TTTGTGTAAATTGAAAGTTTAGAAGTAGGTTTTTGATTGGAGCGTGTTTT

TTGTTTAGTAAGAGATTTGTTTTTTTTTTTTTTTTTTTTTTTTTT

TTTTTTTTTTGAGACGGAGTTTCGTTTTTGTTATTTAGGTTGGAGTGTA

ATGGCGCGATTTTAGTTTATTTTAATTTTTATTTTTAGGTTTAAGCGAT

TTTTTTGTTTTAGTTTTTTGAGTAGATGGGATTATAAGTATGAGTTTTTA

TTTTGGTTAATTTTGTATTTTTAGTAGAGACGGGTTTTTTTTATGTTGGT

TAGGTTGGTTTAGAATTTTCGATTTTAGGTGATTTGTTAGTTTTAGTTTT

TTAAAGTGTTGGGATTATAGGCGTGAGTTATTATATTCGGTTTTTTTTTT

TTTTTTTTTTTTTTTTTTTTTTTTTTTTATTTTTTGTTTTTTTTT

TTTTTTTTTTTTTTTTTTTTTTTTTTTTTTTTTATTTGTTTTT

TTTTTTTTTTTTTTTTTTTTTTTTTTTGATGGAGTTTTATTTTTG

TTGTTTAGGTTGTAGTGTAGTGGTGTTATTTAGGTTTCGTTGTAATTTTC

GGTTTTTAGGTTTAAGCGATTTTTTWGTTTTAGTTTTTTAAATAGTAGGG

ATTATAGGTGTTTGTTTTTATTTTCGGTTAATTTATGTATTTTTAGTAGA

GACGGGGTTTATTATGTTGGTTAGGTTGGTTTCGAATTTTGATTTTAGA

TGATTTATTTGTTTCGGTTTTTTTAAGTGTTGGGATTATAGGTTTGAGTT

ACGGTATTTAGTTTAGATTGTGTTTTGAGTATGATTTTTTTAATTAATT

AATTTATTTTTAGTATTAGATATGTTTTGATTGAGTATGATTTTTATT

ATGTAAGTATTAATTTAGTTTAATTATTGTATATGGCGGGTTTAAAGGAA

AAAGAAAGTTATTAGTTAGAATTAGAGAATAAGATATTTAGAAGATAGTT

TTTATTTAGAATTATTTTGTGTGTGTGTGTGTGTGTGTGTGTGTGTGT

-continued
TTGAGATAGAGTTTTATTTTGTTATTTAGGTTGGAGTGTAGTGGCGCGAT

TTCGGTTTATTGTAAGTTTTGTTTATTGGGTTTATATTATTTTTTGTTT

TAGTTTTTTAAGTAGTTGGGATTATAGGCGTTCGTTATTATGTTTAGTTA

ATTTTTGTATTTTTAGTAGAGACGGGGTTTTATCGTGTTAGTTAGGTTGG

T

SEQ ID NO: 3

Corresponds to a fully unmethylated version of SEQ ID NO: 1 (i.e. in which each cytosine at a CpG dinucleotide is unmethylated) following sodium bisulfite conversion of all unmethylated cytosines to uracil. (Polymorphic bases are denoted with the symbol of their unconverted polymorphism). Conventions with respect to bolded and highlighted bases are maintained from SEQ ID NO: 1 and throughout.

(SEQ ID NO: 3)
AGATTGTGTTTTTTAATTTAAATTAAAATTAAATTTAAAAAAATTTTTA

TTTGAAAGAGAAAAGTTTTTTTGTTAATGTTTTTGTTTTGTTTGTTTTG

TTTTGTGATGGATTTTTTTTTGTTGTTTAGGTTGGAGTGTAGTGGTGTG

ATTTTGGTTTATTGTAATTTTTGTTTTTTGGGTTTAAGTAGTTTTTTGTT

TTGGTTTTTTGAGTAGATGGGATTATAGGTGTTATTAAGTTTGGTTAATT

TTTTGTATTTTTAGTAGAGATGGGGTTTTATTATGTTGGTTAGGAAGGTT

TTGATGTTTGGTTTTGTGATTTGTTTGTTTTGGTTTTTAAATTGTTGA

GATTATAGGTGTGAGTTATTATGTTTGGTTTTTTTTTTTTTGAGATA

GAGTTTTGTTTTGTTGTTTAGGTTGGAGTGAAGTGGTATGTTTTAGTTTA

TTGTAATTTTTRTTTTTTGGGTTTAAGTGATTTTTTAGTTTTAGTTTTTT

GAGTAGTTGGGATTATAGGTGTTTGTTATTATGTTTAGTTAATATTTGTA

TTTTTTAGTAGAGATGGGGTTTTTTTGTTTGTTGGTTAGGTTGGTTTT

GAATTTTTGATTTTAGGTGATTTGTTTATTTTGGTTTTTTAGATTGTTGG

GATTATAGGTGTGAGTTAGTGTGTTTAGGTAATATATATATATATATATA

TTTAATTATAAGAAAGATTAGGTTTTGTTGGGTTGTTTAGGTTGGTTTTA

AATTTTTGAGTTTAAGTGATTTGTTTGTTTTGGTTTTTTGGATGTTGAGG

TTATAGGTGTGAGTTATTGTGTTTGGTTTTATTTTATTTTTTAAGATAG

GGGTATGGATTGTTTGGA GAGTTAGAAATTTTGAGATTTTTGTAGTTTTA

GGAAAGGTTGTGGTTAGTTTTTTTGTGGTATGGGTGTGGTTTTTAGTGAT

TTTTTAGTTTGGGGTTTTTTTTGGGTTGTAGATTTTGTGTGTTTGTTA

GTAGTGTTTGGTTTTAATAGTTGTTGTTGGTTTTTTTTTTGTGGTTTT

TTTTTGAAATGGATTTTTTTTTGGGGAATAGAAAGTGTTAGTTATGTAG

TTTTGGTATGGAAAGGTTRTGTAGAGAGTTTTTGAGGTTGGAGTTATTGT

TTTTAAGGTTTTTGTATGGAATGTTAGGGGTGTTTTGATGGATTTTAMT

GAGTTTTTGGTTGTTTTTGAGGTTGTTTTGTTTAAGGMGGGAAAGTTTGG

TTTTGTTAGRAAGTTGGGATTTTGGTAGAAAAAGAGTGTTTTGGATATTT

AGGAGAGGTTGTTTGTTTGTGTAATTGGGGTTTGTGTTAAAAAGGTTTTT

TAGTGTGTTTAGGATATGTAGTTGTTTGATGTTATTAGTGTTTTTGGGGT

AGAGGGGTTGGAGTTTTTTGTGGTTTGGGAGTTGGTTTTTTTTAGGGTTG

GTTTTTGTTGTTAGAGGGGTGTGTGTTGTTTTATGAAGTTAAGATTTTTG

TTTGGGTTTTGGGATGTGTTTAGTTTTGGTTTGTTGGTTTTGGTTTTTAT

TTTTGTATGGAGGGATGTGGTGTTTGGGGTTTTGAAGTTTGGGTGGTTT

TGGAGAAGTTGAAGTTTAGTTGTGATGATATTTTTATGGTGGTGGGGATG

GTGAAAGGGGTTGTGGATTATTTGTTGTTTAGATTGAAGTGTGATTTTGT

GTTTAGAGGTGTTGGGTTGTTGAATATTGGGAGTTATTATGAGTATGTGA

AGGTGAGTTGTTTGGTGTTTTTTGTTGAGTTTTGTTGTTTGGTTTTTTG

TAATTTGTAGTTTTTATTTTTTTGGGTTGTGTTTTTATTTTTTTTGG

AAGTAATTTAGATTTTTGTATGTTTTTTGGTAGTTTAGTTTAAGTAAAAT

GATAAATTGTTTGTTTATTTATTTATATATTTAATGATTAGATAATTAAT

TGGTATTGATTGTTGGTTAATTTTAAGATATTGTTTTTGGGGGAATTTAA

ATGTATGGGTTTATTTATGTAAGTTGATATGTATTGAGTTTTTGTAATAG

GGTAGTGTTTGATGGTGTGGATTTGAGGTTTTGAGTTAGATATTGATTTG

GATAATTTGAAGTGGTTTGTTAAAAATTTTATGTAGATTTTTTTTATGA

GGAAGATTTTTATTTTATAGAAAAAAAGATTTTTAGTTTTTTTTTTTTT

TTTTTTTTTGTTTTTTTTTTGTTATTTTGTTTGATTTTAATTTTTTTT

TTTTTTTTTTTTTTTTTTTTTTTTTTTTTTTTTGAGGTGGAGTTTT

GTTGTGTTTTTAGGTTGGAGTGTAGTGGTGTTATTTTGGTTTATTGTAA

GTTTTGTTTTTGGGTTTATGTTATTTTTTGTTTTAGTTTTTTGAGTAG

TTGGGATTATAGGTGTTTGTTATTATGTTTGGTTAATTTTTTTTGTATTT

TTAGTAGAGATGGTGTTTTATTGTGTTAGTTAGGATGGTTTTGATTTTTT

GATTTTTTGATTTGTTTGTTTGGTTTTTAAAGTGTTGGGATTATAGGT

GTSAGTTATTGTGTTTGGTGTTTGTTTTAGTTTTTTATATAGAAATTA

TGGGAAGTTTATAGTATAATGTTAAATAAATAAATAAGAATATTTTTTAT

AGATATTAAAATGTTTTTTAGATATATATTTTGTATAATTGTTTTGATGT

GTGTATTATATAGTTTTATTTGTTTGTGGGTGATTGAGTTATTAATTATT

TTTGTGTAAATTGAAAGTTTAGAAGTAGGTTTTTGATTGGAGTGTGTTTT

TTGTTTAGTAAGAGATTTGTTTTTTTTTTTTTTTTTTTTTTTTTTT

TTTTTTTTTTGAGATGGAGTTTTGTTTTGTTATTTAGGTTGGAGTGTA

ATGGTGTGATTTTAGTTTATTTTAATTTTTATTTTTAGGTTTAAGTGAT

TTTTTTGTTTAGTTTTTTGAGTAGATGGGATTATAAGTATGAGTTTTTA

TTTTGGTTAATTTTGTATTTTTAGTAGAGATGGGTTTTTTTATGTTGGT

TAGGTTGGTTTAGAATTTTTGATTTAGGTGATTTGTTAGTTTTAGTTTT

TTAAAGTGTTGGGATTATAGGTGTGAGTTATTATATTTGGTTTTTTTTT

TTTTTTTTTTTTTTTTTTTTTTTTTTTTTATTTTTTGTTTTTTTTT

TTTTTTTTTTTTTTTTTTTTTTTTTTTTTTTTTTATTTGTTTTT

TTTTTTTTTTTTTTTTTTTTTTTTTTTGATGGAGTTTTATTTTTG

TTGTTTAGGTTGTAGTGTAGTGGTGTTATTTAGGTTTTGTTGTAATTTTT

GGTTTTAGGTTTAAGTGATTTTTWGTTTTAGTTTTTTAAATAGTAGGG

ATTATAGGTGTTTGTTTTATTTTGGTTAATTTATGTATTTTTAGTAGA

```
GATGGGGTTTTATTATGTTGGTTAGGTTGGTTTTGAATTTTGATTTTAGA

TGATTTATTTGTTTTGGTTTTTTTAAGTGTTGGGATTATAGGTTTGAGTT

ATGGTATTTAGTTTAGATTGTGTTTTGAGTATGATTTTTTTTAATTAATT

AATTTATTTTTTAGTATTAGATATGTTTTTGATTGAGTATGATTTTTATT

ATGTAAGTATTAATTTAGTTTAATTATTGTATATGGTGGGTTTAAAGGAA

AAAGAAAGTTATTAGTTAGAATTAGAGAATAAGATATTTAGAAGATAGTT

TTTATTTAGAATTATTTTGTGTGTGTGTGTGTGTGTGTGTGTGTGTGTGT

TTGAGATAGAGTTTTATTTTGTTATTTAGGTTGGAGTGTAGTGGTGTGAT

TTTGGTTTATTGTAAGTTTTGTTTATTGGGTTTATATTATTTTTTGTTT

TAGTTTTTTAAGTAGTTGGGATTATAGGTGTTTGTTATTATGTTTAGTTA

ATTTTTGTATTTTTAGTAGAGATGGGGTTTTATTGTGTTAGTTAGGTTGG

T
```

SEQ ID NO: 4

Figure 15A:
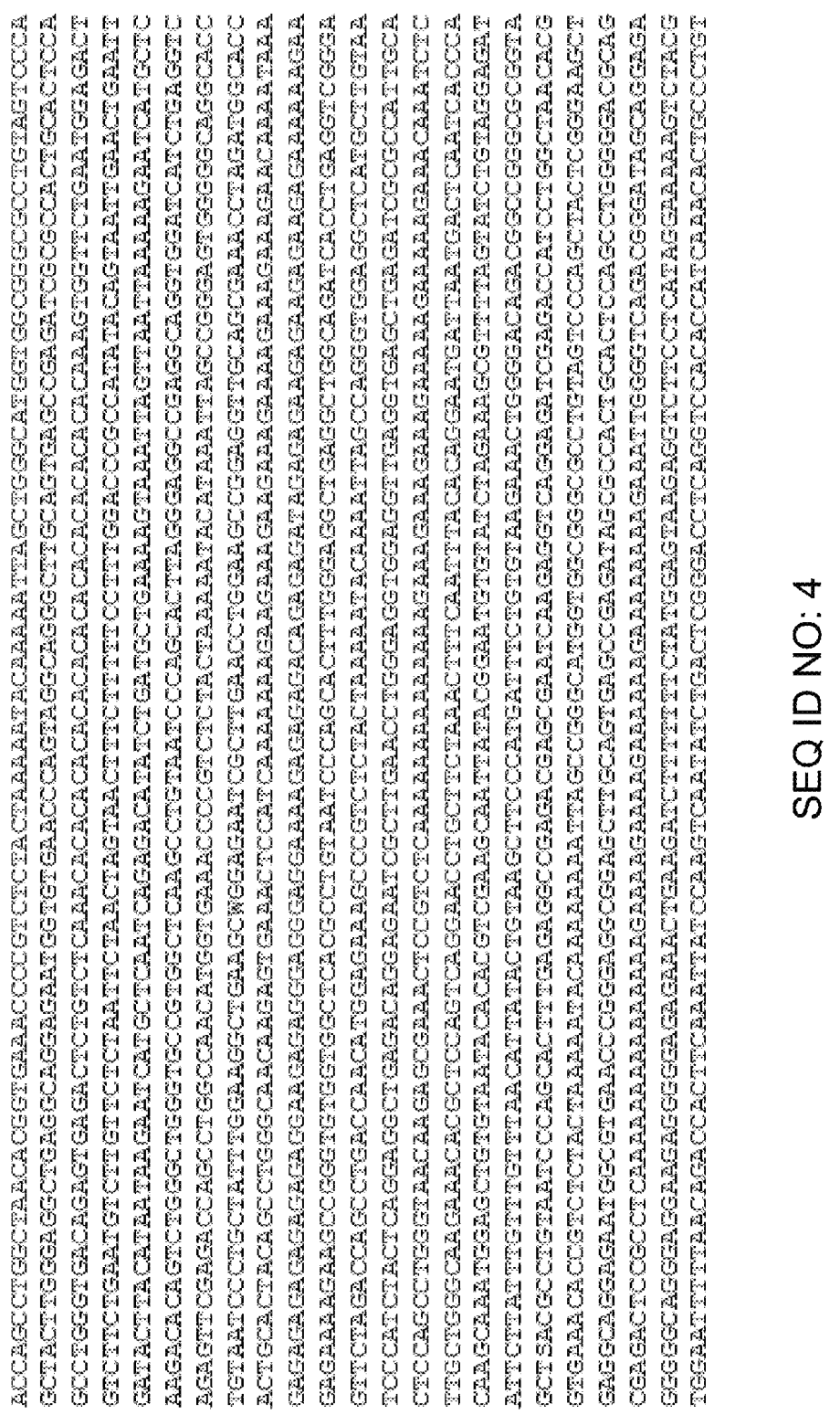

Depicts the genomic sequence of the genomic (+) strand aligned to the C6Orf150 antisense strand in which bp 1-4000 of the sequence correspond to (hg18) coordinates 74,215, 7207-4,219,719. The yellow highlighted region in FIG. 15A and B corresponds to the C6Orf150 Differentially Methylated Domain (DMR), italicized below. The bolded and double-underlined bases (black bolded and underlined in FIG. 15A and B) correspond to the locations of outer flanking primers used to amplify the differentially methylated region following bisulfite conversion of unmethylated cytosine bases to uracil. The unbolded, italicized, and double-underlined bases (red, bolded and underlined bases in FIG. 15A and B) correspond to the locations of primers that amplify up the MSP-8 target region domain following bisulfite conversion.

```
                                              (SEQ ID NO: 4)
ACCAGCCTGGCTAACACGGTGAAACCCCGTCTCTACTAAAAATACAAA

AATTAGCTGGGCATGGTGGCGGGCGCCTGTAGTCCCAGCTACTTGGGA

GGCTGAGGCAGGAGAATGGTGTGAACCCAGTAGGCAGGGCTTGCAGTG

AGCCGAGATCGCGCCACTGCACTCCAGCCTGGGTGACAGAGTGAGACT

CTGTCTCAAACACACACACACACACACACACACACACACACAAAGTGG

TTCTGAATGGAGACTGTCTTCTGAATGTCTTGTTCTCTAATTCTAACT

AGTAACTTTCTTTTTCCTTTGGACCCGCCATATACAGTAATTGAACTG

AATTGATACTTACATAATAAGAATCATGCTCAATCAGAGACATATCTG

ATGCTGAAAAGTAAATTAGTTAATTAAAAAGAATCATGCTCAAGACAC

AGTCTGGGCTGGGTGCCGTGGCTCAAGCCTGTAATCCCAGCACTTAGG

GAGGCCGAGGCAGGTGGATCATCTGAGGTCAGAGTTCGAGACCAGCCT

GGCCAACATGGTGAAACCCCGTCTCTACTAAAAATACATAAATTAGCC

GGGAGTGGGGCAGGCACCTGTAATCCCTGCTATTTGGAAGGCTGAAG

CWGGAGAATCGCTTGAACCTGGAAGCCGGAGGTTGCAGCGAAACCTAG

ATGGCACCACTGCACTACAGCCTGGGCAACAAGAGTGAAACTCCATCA

AAAAAAGAAGAAGAAGAAAGAAAAGAAAGAAGAACAAAATAAAGAG

AGAGAGAGAGAGAGGAAGAGAGGGAGGGAGGAAAAGAGAGAGACAGAG

AGATAGAGAGAAGAGAAGAGAAGAGAAAAAGAAGAGAAAAGAAGCCG

GGTGTGGTGGCTCACGCCTGTAATCCCAGCACTTTGGGAGGCTGAGGC

TGGCAGATCACCTGAGGTCGGGAGTTCTAGACCAGCCTGACCAACATG

GAGAAAGCCCGTCTCTACTAAAAATACAAAATTAGCCAGGGTGGAGGC

TCATGCTTGTAATCCCATCTACTCAGGAGGCTGAGACAGGAGAATCGC

TTGAACCTGGGAGGTGGAGGTTGAGGTGAGCTGAGATCGCGCCATTGC

ACTCCAGCCTGGGTAACAAGAGCGAAACTCCGTCTCAAAAAAAAAAAA

AAGAAAGAAAGAAAGAAAAAGAAAAAGAAACAAATCTCTTGCTGGGCA

AGAAACACGCTCCAGTCAGGAACCTGCTTCTAAACTTTCAATTTACAC

AGGAATGATTAATGACTCAATCACCCACAAGCAAATGGAGCTGTGTAA

TACACACGTCGAAGCAATTATACGGAATGTGTATCTAGAAAGCGTTTT

AGTATCTGTAGGAGATATTCTTATTTGTTTGTTTAACATTATACTGTA

AGCTTCCCATGATTTCTGTGTAAGAAACTGGGGACAGACGGCCGGGCG

CGGTAGCTSACGCCTGTAATCCCAGCACTTTGAGAGGCCGAGACGAGC

GAATCAAGAGGTCAGGAGATCGAGACCATCCTGGCTAACACGGTGAAA

CACCGTCTCTACTAAAAATACAAAAAAATTAGCCGGGCATGGTGGCG

GGCGCCTGTAGTCCCAGCTACTCGGGAAGCTGAGGCAGGAGAATGGCG

TGAACCCGGGAGGCGGAGCTTGCAGTGAGCCGAGATAGCGCCACTGCA

CTCCAGCCTGGGGGACGCAGCGAGACTCCGCCTCAAAAAAAAAAAAAA

AGAAAAGAAAAGAAAAAAGAAAAAAAAGAAATTGGGGTCAGACGGGAT

AGCAGGAGAGGGGCAGGGAGGAAGAGGGGGAGAGAAACTGAAGATCT

TTTTTTCTATGGAGTAAGAGGTCTTCCTCATAGGAAAAAGTCTACGTG

GAATTTTTAACAGACCACTTCAAATTATCCAAGTCAATATCTGACTCG

GGACCTCAGGTCCACACCATCAAACACTGCCCTGTTACGGAAACTCGA

TACATGTCGGCTTGCATGAATGAACCCATACATTTGAATTCCCCCGGG

AGCAGTGTCTTGAAATTAGCCAGCAATCAGTACCGGTTGGTTGTCTGA

TCGTTGGATGTGTAGATGAATAAACGAACGGTTTGTCGTTTTACTTAG

ACTAGGCTACCGAAAAACATGCAAAAGTCTAAGTTACTTCCGAAGGGA

AGTGAGGGGCGCGACCCGGGGAAGGTAGGGACTGCGGATTGCGGAAGG

CCGAGCAGCGGGGCTCGGCGGGAGGGCGCCAAGCAGCTCACCTTCACG

TGCTCATAGTAGCTCCCGGTGTTCAGCAGCCCGACGCCTCTGAACGCG

GAGTCGCACTTCAGTCTGAGCAGCAGGTGGTCCACAACCCCTTTCACC

ATCCCCGCCGCCGTGGAGATATCATCGCGGCTGAGCTTCAACTTCTCC

AAAACCGCCCGGAGCTTCGAGGCCCCAGGCGCCGCATCCCTCCGTACG

AGAATGGGGCCGAGACCGGCAGGCCGGGCTGGGCACGTCCCAGGGC

CCGGGCGGRGGTCTTGGCTTCGTGGAGCAGCGCGCGCCCCTCTGGCGG

CAAGAACCAGCCCTGGAAAGAGCCGGCTCCCGAGCCGCAGGAGGCTCC

AGCCCCTCTGCCCCAGGGGCGCTGGTGGCGTCAGACGGCTGCGTGTCC

TGGGCGCGCTGAGGGGCCTTTTTGGCGCGGGCCCCAGTTGCGCGGACG

GGCGGCCTCTCCTGGGTGTCCGGGGCGCTCTTTTTCTGCCGGGATCCC

GACTTYCTGGCGGGGCCGAACTTTCCCKCCTTAGGCAGGGCGGCCTCG
```

-continued

<u>*GGGGCAGCCGGAGACTC*G</u>*KTGGGATCCATCGGGGCGCCCCTGGCATTC*

*CGTGCGGAAGCCTTGGGGGCAGTGGCTCCGGCCTCGGAAGCTCTCTGC*

*AYGGCCTTTCCGTGCCAAGGCTGCATGGCTGGCGCTTTCTGTTCCCCG*

*AAAGAAGAATCCGTTTCAGGAAAAGGCCGCAAGAGGAAGAGCCAGCAG*

*CAGCTGTTGGAAACCAAGCACTACTGGCGGGCACACAAGAGTCTGCGA*

*CCCGAAGGGGAACCCCAGGCTGGGAAGTCGCTGGGAGCCACGCCCATG*

*CCGCGAAGAGGCTGGCCGCGGCCTTTCCTGAGGCTACAAAAGTCTCGA*

*A*<u>GTTTCTAACTCTCCAGGCAATCC</u>*GTGCCCCTGTCTTAAGAAGATGAG*

*GTAGGGCCGGGCGCGGTGGCTCACGCCTGTAACCTCAGCATCCGAGAG*

*GCCGAGGCAGGCGGGTCGCTTGAGCTCAGGAGTTTGAGACCAGCCTGG*

*GCAACCCAGCAAGACCTGTCTTTCTTATAATTAAATATATGTGTGTG*

*TGTGTGTTGCCTGGGCACACTGACTCACGCCTGTAATCCCAGCAATCT*

*GGGAGACCGAGGTGGGCGGATCACCTGAGGTCAGGAGTTCAAGACCAG*

*CCTGGCCAACAAGGCGAAAGAAACCCCGTCTCTACTAAAAAATACAAA*

*TATTAGCTAGGCGTGGTGGCGGGCACCTGTAATCCCAGCTACTCGGGA*

*GGCTGAGGCTGGAGAATCACTTGAACCCGGGAGGYGGAGGTTGCAGTG*

*AGCTGAGACGTGCCACTTCACTCCAGCCTGGGCGACAGAGCGAGACTC*

*TGTCTCAAAAAGAAAAGAGGCCAGGCGTGGTGGCTCACGCCTGTAA*

*TCTCAGCAGTTTGGGAGGCCGAGGCGGGCGGATCACGAGGCCAAGACA*

*TCGAGACCTTCCTGGCCAACATGGTGAAACCCCGTCTCTACTAAAAAT*

*ACAAAAAATTAGCCGGGCTTGGTGGCGCCTGTAGTCCCATCTACTCGG*

*GAGGCCGAGACAGAGAACTGCTTGAACCCGGGAGGCAGAGGTTGCAGT*

*GAGCCGAGATCGCGCCACTGCACTCCAGCCTGGGCAACAGAAAAAGAG*

*TCCATCACAAAACAAAACAAAACAAAACAAAAACATTGACAGAGAAAC*

*TTTTCTCTTTCAAGTGAAAGTTTTTTTAAATTTAATTTTGGTTTGAGT*

*TAGGGGGGCGCAATCT*

SEQ ID NO: 5
Bisulfite converted sequence arising from a fully methylated form of SEQ ID NO: 4.

(SEQ ID NO: 5)
*ATTAGTTTGGTTAATACGGTGAAATTTCGTTTTTATTAAAAATATAAA*

*AATTAGTTGGGTATGGTGGCGGCGTTTGTAGTTTTAGTTATTTGGA*

*GGTTGAGGTAGGAGAATGGTGTGAATTTAGTAGGTAGGGTTTGTAGTG*

*AGTCGAGATCGCGTTATTGTATTTTAGTTTGGGTGATAGAGTGAGATT*

*TTGTTTTAAATATATATATATATATATATATATATATATATAAAGTGG*

*TTTTGAATGGAGATTGTTTTTGAATGTTTTGTTTTTAATTTTAATT*

*AGTAATTTTTTTTTTTTTGGATTCGTTATATATAGTAATTGAATTG*

*AATTGATATTTATATAATAAGAATTATGTTTAATTAGAGATATATTTG*

*ATGTTGAAAAGTAAATTAGTTAATTAAAAAGAATTATGTTTAAGATAT*

*AGTTTGGGTTGGGTGTCGTGGTTTAAGTTTGTAATTTTAGTATTTAGG*

*GAGGTCGAGGTAGGTGGATTATTTGAGGTTAGAGTTCGAGATTAGTTT*

*GGTTAATATGGTGAAATTTCGTTTTTATTAAAAATATATAAATTAGTC*

*GGGAGTGGGGGTAGGTATTTGTAATTTTTGTTATTTGGAAGGTTGAAG*

*TWGGAGAATCGTTTGAATTTGGAAGTCGGAGGTTGTAGCGAAATTTAG*

*ATGGTATTATTGTATTATAGTTTGGGTAATAAGAGTGAAATTTTATTA*

*AAAAAGAAGAAGAAGAAAGAAAAGAAAGAAGAATAAAATAAAGAG*

*AGAGAGAGAGAGGAAGAGAGGGAGGGAGGAAAAGAGAGAGATAGAG*

*AGATAGAGAGAAGAGAAGAGAAGAGAAAAAAGAAGAGAAAAGAAGTCG*

*GGTGTGGTGGTTTACGTTTGTAATTTTAGTATTTTGGGAGGTTGAGGT*

*TGGTAGATTATTTGAGGTCGGGAGTTTTAGATTAGTTTGATTAATATG*

*GAGAAAGTTCGTTTTTATTAAAAATATAAAATTAGTTAGGGTGGAGGT*

*TTATGTTTGTAATTTTATTTATTTAGGAGGTTGAGATAGGAGAATCGT*

*TTGAATTTGGGAGGTGGAGGTTGAGGTGAGTTGAGATCGCGTTATTGT*

*ATTTTAGTTTGGGTAATAAGAGCGAAATTTCGTTTTAAAAAAAAAAAA*

*AAGAAAGAAAGAAAAGAAAAAGAAATAAATTTTTTGTTGGGTA*

*AGAAATACGTTTTAGTTAGGAATTTGTTTTTAAATTTTTAATTTATAT*

*AGGAATGATTAATGATTTAATTATTTATAAGTAAATGGAGTTGTGTAA*

*TATATACGTCGAAGTAATTATACGGAATGTGTATTTAGAAAGCGTTTT*

*AGTATTTGTAGGAGATATTTTTATTTGTTTGTTTAATATTATATTGTA*

*AGTTTTTTATGATTTTTGTGTAAGAAATTGGGGATAGACGGTCGGGCG*

*CGGTAGTTSACGTTTGTAATTTTAGTATTTTGAGAGGTCGAGACGAGC*

*GAATTAAGAGGTTAGGAGATCGAGATTATTTTGGTTAATACGGTGAAA*

*TATCGTTTTTATTAAAAATATAAAAAAATTAGTCGGGTATGGTGGCG*

*GGCGTTTGTAGTTTTAGTTATTCGGGAAGTTGAGGTAGGAGAATGGCG*

*TGAATTCGGGAGGCGGAGTTTGTAGTGAGTCGAGATAGCGTTATTGTA*

*TTTTAGTTTGGGGGACGTAGCGAGATTTCGTTTTAAAAAAAAAAAAA*

*AGAAAAGAAAGAAAAAGAAAAAAAAAGAAATTGGGGTTAGACGGGAT*

*AGTAGGAGAGGGGTAGGGAGGAAGAGGGGGAGAGAAATTGAAGATTT*

*TTTTTTTTATGGAGTAAGAGGTTTTTTTTATAGGAAAAAGTTTACGTG*

*GAATTTTTAATAGATTATTTTAAATTATTTAAGTTAATATTTGATTCG*

*GGATTTTAGGTTTATATTATTAAATATTGTTTTGTTACGGAAATTCGA*

*TATATGTCGGTTTGTATGAATGAATTTATATATTTGAATTTTTTCGGG*

*AGTAGTGTTTTGAAATTAGTTAGTAA*<u>TTAGTATCGGTTGGTTGTTTG</u>*A*

*TCGTTGGATGTGTAGATGAATAAACGAACGGTTTGTCGTTTTATTTAG*

*ATTAGGTTATCGAAAAATATGTAAAAGTTTAAGTTATTTTCGAAGGGA*

*AGTGAGGGCGCGATTCGGGGAAGGTAGGGATTGCGGATTGCGGAAGG*

*TCGAGTAGCGGGGTTCGGCGGGAGGGCGTTAAGTAGTTTATTTTTACG*

*TGTTTATAGTAGTTTTCGGTGTTTAGTAGTTCGACGTTTTTGAACGCG*

*GAGTCGTATTTTAGTTTGAGTAGTAGGTGGTTTATAATTTTTTTTATT*

*ATTTTCGTCGTCGTGGAGATATTATCGCGGTTGAGTTTTAATTTTTTT*

*AAAATCGTTCGGAGTTTCGAGGTTTTAGGCGTCGTATTTTTTCGTACG*

*AGAATGGGGGTCGAGATCGGTAGGTCGGGGTTGGGTACGTTTTAGGGT*

-continued

```
TCGGGCGGRGGTTTTGGTTTCGTGGAGTAGCGCGCGTTTTTTTGGCGG
TAAGAATTAGTTTTGGAAAGAGTCGGTTTTCGAGTCGTAGGAGGTTTT
AGTTTTTTTGTTTTAGGGGCGTTGGTGGCGTTAGACGGTTGCGTGTTT
TGGGCGCGTTGAGGGGTTTTTTGGCGCGGGTTTTAGTTGCGCGGACG
GCGGTTTTTTTGGGTGTTCGGGGCGTTTTTTTTTGTCGGGATTTC
GATTCTTGGCGGGGTCGAATTTTTTTKTTTTAGGTAGGGCGGTTTCG
GGGGTAGTCGGAGATTCGKTGGGATTTATCGGGGCGTTTTTGGTATTT
CGTGCGGAAGTTTTGGGGGTAGTGGTTTCGGTTTCGGAAGTTTTTTGT
ACGGTTTTTTCGTGTTAAGGTTGTATGGTTGGCGTTTTTTGTTTTTCG
AAAGAAGAATTCGTTTTAGGAAAAGGTCGTAAGAGGAAGAGTTAGTAG
TAGTTGTTGGAAATTAAGTATTATTGGCGGGTATATAAGAGTTTGCGA
TTCGAAGGGGAATTTTAGGTTGGGAAGTCGTTGGGAGTTACGTTTATG
TCGCGAAGAGGTTGGTCGCGGTTTTTTTTGAGGTTATAAAAGTTTCGA
AGTTTTAATTTTTTAGGTAATTCGTGTTTTTGTTTTAAGAAGATGAG
GTAGGGTCGGGCGCGGTGGTTTACGTTTGTAATTTTAGTATTCGAGAG
GTCGAGGTAGGCGGGTCGTTTGAGTTTAGGAGTTTGAGATTAGTTTGG
GTAATTTAGTAAGATTTGGTTTTTTTTATAATTAAATATATGTGTGTG
TGTGTGTTGTTTGGGTATATTGATTTACGTTTGTAATTTTAGTAATTT
GGGAGATCGAGGTGGGCGGATTATTTGAGGTTAGGAGTTTAAGATTAG
TTTGGTTAATAAGGCGAAAGAAATTTCGTTTTTATTAAAAAATATAAA
TATTAGTTAGGCGTGGTGGCGGGTATTTGTAATTTTAGTTATTCGGGA
GGTTGAGGTTGGAGAATTATTTGAATTCGGGAGGCGGAGGTTGTAGTG
AGTTGAGACGTGTTATTTTATTTTAGTTTGGGCGATAGAGCGAGATTT
TGTTTTAAAAAGAAAAGAGGTTAGGCGTGGTGGTTTACGTTTGTAA
TTTTAGTAGTTTGGGAGGTCGAGGCGGGCGGATTACGAGGTTAAGATA
TCGAGATTTTTTTGGTTAATATGGTGAAATTTCGTTTTTATTAAAAAT
ATAAAAAATTAGTCGGGTTTGGTGGCGTTTGTAGTTTTATTTATTCGG
GAGGTCGAGATAGAGAATTGTTTGAATTCGGGAGGTAGAGGTTGTAGT
GAGTCGAGATCGCGTTATTGTATTTTAGTTTGGGTAATAGAAAAAGAG
TTTATTATAAAATAAAATAAAATAAAATAAAAATATTGATAGAGAAAT
TTTTTTTTTTAAGTGAAAGTTTTTTAAATTTAATTTTGGTTTGAGT
TAGGGGGGCGTAATTT
```

SEQ ID NO: 6
Bisulfite converted sequence arising from a fully unmethylated form of SEQ ID NO: 4.

(SEQ ID NO: 6)
```
ATTAGTTTGGTTAATATGGTGAAATTTTGTTTTTATTAAAAATATAAA
AATTAGTTGGGTATGGTGGTGGGTGTTTGTAGTTTTAGTTATTTGGGA
GGTTGAGGTAGGAGAATGGTGTGAATTTAGTAGGTAGGGTTTGTAGTG
AGTTGAGATTGTGTTATTGTATTTTAGTTTGGGTGATAGAGTGAGATT
TTGTTTTAAATATATATATATATATATATATATATATATATAAAGTGG
TTTTGAATGGAGATTGTTTTTTGAATGTTTTGTTTTTTAATTTTAATT
AGTAATTTTTTTTTTTTTGGATTTGTTATATATAGTAATTGAATTG
AATTGATATTTATATAATAAGAATTATGTTTAATTAGAGATATATTTG
ATGTTGAAAAGTAAATTAGTTAATTAAAAAGAATTATGTTTAAGATAT
AGTTTGGGTTGGGTGTTGTGGTTTAAGTTTGTAATTTTAGTATTTAGG
GAGGTTGAGGTAGGTGGATTATTTGAGGTTAGAGTTTGAGATTAGTTT
GGTTAATATGGTGAAATTTTGTTTTTATTAAAAATATATAAATTAGTT
GGGAGTGGGGTAGGTATTTGTAATTTTTGTTATTTGGAAGGTTGAAG
TWGGAGAATTGTTTGAATTTGGAAGTTGGAGGTTGTAGTGAAATTTAG
ATGGTATTATTGTATTATAGTTTGGGTAATAAGAGTGAAATTTTATTA
AAAAAGAAGAAAGAAGAAAGAAAAGAAAGAAAGAATAAAATAAAGAG
AGAGAGAGAGAGGAAGAGAGGGAGGGAGGAAAAGAGAGAGATAGAG
AGATAGAGAAGAGAAGAGAAGAGAAAAAGAAGAGAAAAGAAGTTG
GGTGTGGTGGTTTATGTTTGTAATTTTAGTATTTTGGGAGGTTGAGGT
TGGTAGATTATTTGAGGTTGGGAGTTTTAGATTAGTTTGATTAATATG
GAGAAAGTTTGTTTTTATTAAAAATATAAAATTAGTTAGGGTGGAGGT
TTATGTTTGTAATTTTATTTATTTAGGAGGTTGAGATAGGAGAATTGT
TTGAATTTGGGAGGTGGAGGTTGAGGTGAGTTGAGATTGTGTTATTGT
ATTTTAGTTTGGGTAATAAGAGTGAAATTTTGTTTTAAAAAAAAAAAA
AAGAAAGAAAGAAAAGAAAAAGAAATAAATTTTTTGTTGGGTA
AGAAATATGTTTTAGTTAGGAATTTGTTTTTAAATTTTTAATTTATAT
AGGAATGATTAATGATTTAATTATTTATAAGTAAATGGAGTTGTGTAA
TATATATGTTGAAGTAATTATATGGAATGTGTATTTAGAAAGTGTTTT
AGTATTTGTAGGAGATATTTTATTTGTTTGTTTAATATTATATTGTA
AGTTTTTTATGATTTTTGTGTAAGAAATTGGGGATAGATGGTTGGGTG
TGGTAGTTSATGTTTGTAATTTTAGTATTTTGAGAGGTTGAGATGAGT
GAATTAAGAGGTTAGGAGATTGAGATTATTTGGTTAATATGGTGAAA
TATTGTTTTTATTAAAAATATAAAAAAATTAGTTGGGTATGGTGGTG
GGTGTTTGTAGTTTTAGTTATTTGGGAAGTTGAGGTAGGAGAATGGTG
TGAATTTGGGAGGTGGAGTTTGTAGTGAGTTGAGATAGTGTTATTGTA
TTTTAGTTTGGGGATGTAGTGAGATTTTGTTTTAAAAAAAAAAAAA
AGAAAAGAAAGAAAAAGAAAAAAAGAAATTGGGGTTAGATGGGAT
AGTAGGAGAGGGGTAGGGAGGAAGAGGGGGAGAGAAATTGAAGATTT
TTTTTTTATGGAGTAAGAGGTTTTTTTTATAGGAAAAAGTTTATGTG
GAATTTTAATAGATTATTTTAAATTATTTAAGTTAATATTTGATTTG
GGATTTTAGGTTTATATTATTAAATATTGTTTTGTTATGGAAATTTGA
TATATGTTGGTTTGTATGAATGAATTTATATATTTGAATTTTTTGGG
AGTAGTGTTTTGAAATTAGTTAGTAATTAGTATTGGTTGGTTGTTTGA
TTGTTGGATGTGTAGATGAATAAATGAATGGTTTGTTGTTTTATTAGA
TTAGGTTATTGAAAAATATGTAAAAGTTTAAGTTATTTTTTGAAGGGAA
```

-continued

```
GTGAGGGGTGTGATTTGGGGAAGGTAGGGATTGTGGATTGTGGAAGGT

TGAGTAGTGGGGTTTGGTGGGAGGGTGTTAAGTAGTTTATTTTTATGT

GTTTATAGTAGTTTTTGGTGTTTAGTAGTTTGATGTTTTTGAATGTGG

AGTTGTATTTTAGTTTGAGTAGTAGGTGGTTTATAATTTTTTTATTA

TTTTTGTTGTTGTGGAGATATTATTGTGGTTGAGTTTTAATTTTTTA

AAATGTTTGGAGTTTTGAGGTTTTAGGTGTTGTATTTTTTTGTATGA

GAATGGGGGTTGAGATTGGTAGGTTGGGGTTGGGTATGTTTTAGGGTT

TGGGTGGGRGGTTTTGGTTTTGTGGAGTAGTGTGTGTTTTTTTGGTGGT

AAGAATTAGTTTTGGAAAGAGTTGGTTTTTGAGTTGTAGGAGGTTTTA

GTTTTTTTGTTTTAGGGGTGTTGGTGGTGTTAGATGGTTGTGTGTTTT

GGGTGTGTTGAGGGGTTTTTTGGTGTGGGTTTTAGTTGTGTGGATGG

GTGGTTTTTTTTGGGTGTTTGGGGTGTTTTTTTTTGTTGGGATTTTG

ATTTTTTGGTGGGGTTGAATTTTTTTKTTTTAGGTAGGTGGTTTTGG

GGGTAGTTGGAGATTTGKTGGGATTTATTGGGGTGTTTTTGGTATTTT

GTGTGGAAGTTTTGGGGGTAGTGGTTTTGGTTTTGGAAGTTTTTTGTA

TGGTTTTTTTGTGTTAAGGTTGTATGGTTGGTGTTTTTTGTTTTTGA

AAGAAGAATTTGTTTTAGGAAAAGGTTGTAAGAGGAAGAGTTAGTAGT

AGTTGTTGGAAATTAAGTATTATTGGTGGGTATATAAGAGTTTGTGAT

TTGAAGGGGAATTTTAGGTTGGGAAGTTGTTGGGAGTTATGTTTATGT

TGTGAAGAGGTTGGTTGTGGTTTTTTTGAGGTTATAAAAGTTTTGAA

GTTTTTAATTTTTTAGGTAATTTGTGTTTTTGTTTTAAGAAGATGAGG

TAGGGTTGGGTGTGGTGGTTTATGTTTGTAATTTTAGTATTTGAGAGG

TTGAGGTAGGTGGGTTGTTTGAGTTTAGGAGTTTGAGATTAGTTTGGG

TAATTTAGTAAGATTTGGTTTTTTTTATAATTAAATATATGTGTGTGT

GTGTGTTGTTTGGGTATATTGATTTATGTTTGTAATTTTAGTAATTTG

GGAGATTGAGGTGGGTGGATTATTTGAGGTTAGGAGTTTAAGATTAGT

TTGGTTAATAAGGTGAAAGAAATTTTGTTTTTATTAAAAAATATAAAT

ATTAGTTAGGTGTGGTGGTGGGTATTTGTAATTTTAGTTATTTGGGAG

GTTGAGGTTGGAGAATTATTTGAATTTGGGAGGTGGAGGTTGTAGTGA

GTTGAGATGTGTTATTTTATTTTAGTTTGGGTGATAGAGTGAGATTTT

GTTTTAAAAAAGAAAAAGAGGTTAGGTGTGGTGGTTTATGTTTGTAAT

TTTAGTAGTTTGGGAGGTTGAGGTGGGTGGATTATGAGGTTAAGATAT

TGAGATTTTTTGGTTAATATGGTGAAATTTGTTTTTATTAAAAATA

TAAAAAATTAGTTGGGTTTGGTGGTGTTTGTAGTTTTATTTATTTGGG

AGGTTGAGATAGAGAATTGTTTGAATTTGGGAGGTAGAGGTTGTAGTG

AGTTGAGATTGTGTTATTGTATTTTAGTTTGGGTAATAGAAAAGAGT

TTATTATAAAATAAAATAAAATAAAATAAAAATATTGATAGAGAAATT

TTTTTTTTTAAGTGAAAGTTTTTTTAAATTTAATTTTGGTTTGAGTT

AGGGGGGTGTAATTT
```

SEQ ID NO: 7

Figure 14A:
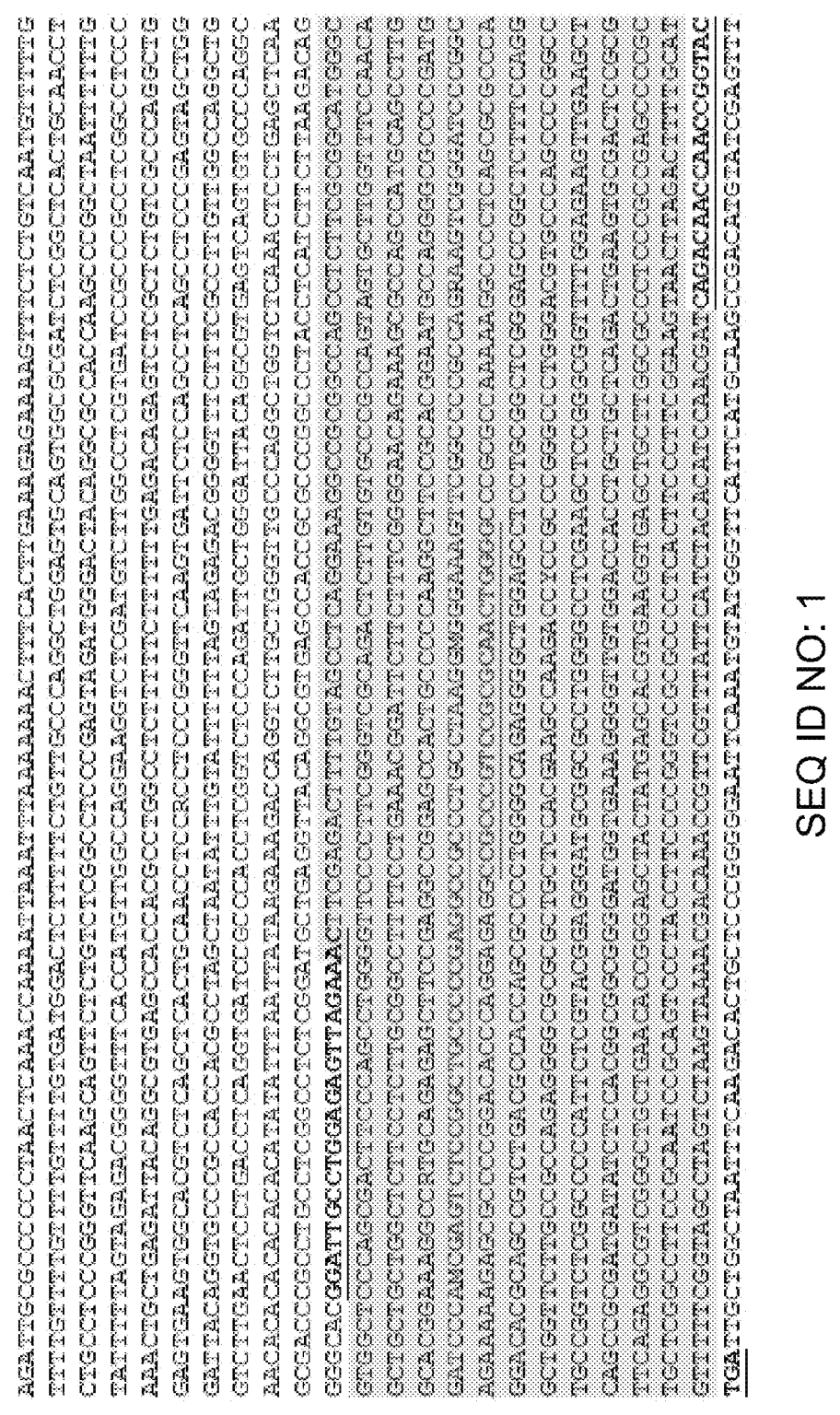

Represents the C6Orf150 differentially methylated region (DMR), as aligned to the genomic (−) strand and the C6Orf150 sense strand, and also corresponds to the entire italicized region in SEQ ID NO: 1 above (i.e., the entire highlighted region in FIGS. 14A and B depicting SEQ ID NO: 1). The sequence is 1060 bp, with bp1=genomic 74,218, 842 (hg18) and bp1060=bp 74,217,783 (hg18). The double-underlined bases correspond to the locations of primers that amplify up the MSP-8 target region domain following bisulfite conversion.

(SEQ ID NO: 7)
```
ACTTCGAGACTTTTGTAGCCTCAGGAAAGGCCGCGGCCAGCCTCTTCG

CGGCATGGGCGTGGCTCCCAGCGACTTCCCAGCCTGGGGTTCCCCTTC

GGGTCGCAGACTCTTGTGTGCCCGCCAGTAGTGCTTGGTTTCCAACAG

CTGCTGCTGGCTCTTCCTCTTGCGGCCTTTTCCTGAAACGGATTCTTC

TTTCGGGGAACAGAAAGCGCCAGCCATGCAGCCTTGGCACGGAAAGGC

CRTGCAGAGAGCTTCCGAGGCCGGAGCCACTGCCCCCAAGGCTTCCGC

ACGGAATGCCAGGGGCGCCCCGATGGATCCCAMCGAGTCTCCGGCTGC

CCCCGAGGCCGCCCTGCCTAAGGMGGGAAAGTTCGGCCCCGCCAGRAA

GTCGGGATCCCGGCAGAAAAAGAGCGCCCCGGACACCCAGGAGAGGCC

GCCCGTCCGCGCAACTGGGGCCCGCGCCAAAAAGGCCCCTCAGCGCGC

CCAGGACACGCAGCCGTCTGACGCCACCAGCGCCCCTGGGGCAGAGGG

GCTGGAGCCTCCTGCGGCTCGGGAGCCGGCTCTTTCCAGGGCTGGTTC

TTGCCGCCAGAGGGGCGCGCGCTGCTCCACGAAGCCAAGACCYCCGCC

CGGGCCCTGGGACGTGCCCAGCCCCGGCCTGCCGGTCTCGGCCCCCAT

TCTCGTACGGAGGGATGCGGCGCCTGGGGCCTCGAAGCTCCGGCGGT

TTTGGAGAAGTTGAAGCTCAGCCGCGATGATATCTCCACGGCGGCGGG

GATGGTGAAAGGGGTTGTGGACCACCTGCTGCTCAGACTGAAGTGCGA

CTCCGCGTTCAGAGGCGTCGGGCTGCTGAACACCGGGAGCTACTATGA

GCACGTGAAGGTGAGCTGCTTGGCGCCCTCCCGCCGAGCCCCGCTGCT

CGGCCTTCCGCAATCCGCAGTCCCTACCTTCCCCGGGTCGCGCCCCTC

ACTTCCCTTCGGAAGTAACTTAGACTTTTGCATGTTTTCGGTAGCCT

AGTCTAAGTAAAACGACAAACCGTTCGTTTATTCATCTACACATCCAA

CGAT
```

SEQ ID NO: 8

Corresponds to the bisulfite converted product of a fully methylated form of SEQ ID NO: 7.

(SEQ ID NO: 8)
```
ATTTCGAGATTTTTGTAGTTTTAGGAAAGGTCGCGGTTAGTTTTTTCG

CGGTATGGGCGTGGTTTTAGCGATTTTTTAGTTTGGGGTTTTTTTTC

GGGTCGTAGATTTTTGTGTGTTCGTTAGTAGTGTTTGGTTTTTAATAG

TTGTTGTTGGTTTTTTTTTTGCGGTTTTTTTTTGAAACGGATTTTTT

TTTCGGGGAATAGAAAGCGTTAGTTATGTAGTTTTGGTACGGAAAGGT

TRTGTAGAGAGTTTTCGAGGTCGGAGTTATTGTTTTTAAGGTTTTCGT

ACGGAATGTTAGGGGCGTTTCGATGGATTTTAMCGAGTTTTCGGTTGT

TTTCGAGGTCGTTTTGTTTAAGGMGGGAAAGTTCGGTTTCGTTAGRAA
```

-continued
GTCGGGATTTCGGTAGAAAAAGAGCGTTTCGGATATTTAGGAGAGG<u>TC</u>

<u>GTTCGTTCGCGTAATTGGGG</u>TTCGCGTTAAAAAGGTTTTTTAGCGCGT

TTAGGATACGTAGTCGTTTGACGTTATTAGCGTTTTTGGGGTAGAGGG

GTTGGAGTTTTTTGCGGTTCGGGAGTCGGTTTTTTTAGGGTTGGTTT

TTGTCGTTAGAGGGGCGCGCGTTGTTTTACGAAGTTAAGATTCTCGTT

CGGGTTTTGGGACGTGTTTAGTTTCGGTTTGTCGGTTTCGGTTTTTAT

TTTCGTACGGAGGGATGCGGCGTTTGGGGTTTCGAAGTTTCGGGCGGT

TTTGGAGAAGTTGAAGTTTAGTCGCGATGATATTTTTACGGCGGCGGG

GATGGTGAAAGGGGTTGTGGATTATTTGTTGTTTAGATTGAAGTGCGA

TTTCGCGTTTAGAGGCGTCGGGTTGTTGAATATCGGGAGTTATTATGA

GTACGTGAAGGTGAGTTGTTTGGCGTTTTTTCGTCGAGTTTCGTTGTT

CGGTTTTTCGTAATTCGTAGTTTTTATTTTTTCGGGTCGCGTTTTTT

ATTTTTTTTCGGAAGTAATTTAGATTTTGTATGTTTTCGGTAGTTT

AGTTTAAGTAAAACGATAAATCGTTCGTTTATTTATTTATATATTTAA

CGAT

SEQ ID NO: 9
Corresponds to the bisulfite converted product of a fully unmethylated form of SEQ ID NO: 7.

(SEQ ID NO: 9)
<u>AT</u>TTTGAGATTTTTGTAGTTTTAGGAAAGGTTGTGGTTAGTTTTTTG

TGGTATGGGTGTGGTTTTTAGTGATTTTTTAGTTTGGGGTTTTTTTTT

GGGTTGTAGATTTTTGTGTGTTTGTTAGTAGTGTTTGGTTTTTAATAG

TTGTTGTTGGTTTTTTTTTTGTGGTTTTTTTTGAAATGGATTTTTT

TTTTGGGGAATAGAAAGTGTTAGTTATGTAGTTTTGGTATGGAAAGGT

TRTGTAGAGAGTTTTTGAGGTTGGAGTTATTGTTTTTAAGGTTTTTGT

ATGGAATGTTAGGGGTGTTTTGATGGATTTTAMT<u>GAGTTTTTGGTTGT</u>

<u>TTTTGAGGTTGTTTTGTTTAAGGMGGGAAAGTTTGGTTTTGTTAGRAA</u>

GTTGGGATTTTGGTAGAAAAAGAGTGTTTTGGATATTTAGGAGAGG<u>TT</u>

<u>GTTTGTTTGTGTAATTGGGG</u>TTTGTTTAAAAAGGTTTTTTAGTGTGT

TTAGGATATGTAGTTGTTTGATGTTATTAGTGTTTTTGGGGTAGAGGG

GTTGGAGTTTTTTGTGGTTTGGGAGTTGGTTTTTTTAGGGTTGGTTT

TTGTTGTTAGAGGGTGTGTTGTTTTATGAAGTTAAGATTTTTGTT

TGGGTTTTGGATGTGTTTAGTTTTGGTTTGTTGGTTTTGGTTTTAT

TTTTGTATGGAGGGATGTGGTGTTTGGGGTTTTGAAGTTTGGGTGGT

TTTGGAGAAGTTGAAGTTTAGTTGTGATGATATTTTTATGGTGGTGGG

GATGGTGAAAGGGGTTGTGGATTATTTGTTGTTTAGATTGAAGTGTGA

TTTTGTGTTTAGAGGTGTTGGGTTGTTGAATATTGGGAGTTATTATGA

GTATGTGAAGGTGAGTTGTTTGGTGTTTTTTGTTGAGTTTTGTTGTT

TGGTTTTTTGTAATTTGTAGTTTTTATTTTTTTGGGTTGTGTTTTTT

ATTTTTTTTCGGAAGTAATTTAGATTTTGTATGTTTTTGGTAGTTT

AGTTTAAGTAAAATGATAAATTGTTTGTTTATTTATTTATATATTTAA

TGAT

SEQ ID NO: 10
Represents the C6Orf150 differentially methylated region (DMR), as aligned to the genomic (+) strand and the C6Orf150 anti-sense strand. This region also corresponds to the entire italicized region in SEQ ID NO: 4 above (i.e., the entire highlighted region in FIGS. 15A and B depicting SEQ ID NO: 4). The sequence is 1060 bp, with bp1=genomic bp 74,217,783 (hg18) and bp1060=74,218,842 bp (hg18). The double-underlined bases correspond to the locations of primers that amplify up the MSP-8 target region domain following bisulfite conversion.

(SEQ ID NO: 10)
ATCGTTGGATGTGTAGATGAATAAACGAACGGTTTGTCGTTTTACTTA

GACTAGGCTACCGAAAAACATGCAAAAGTCTAAGTTACTTCCGAAGGG

AAGTGAGGGGCGCGACCCGGGGAAGGTAGGGACTGCGGATTGCGGAAG

GCCGAGCAGCGGGGCTCGGCGGGAGGGCGCCAAGCAGCTCACCTTCAC

GTGCTCATAGTAGCTCCCGGTGTTCAGCAGCCCGACGCCTCTGAACGC

GGAGTCGCACTTCAGTCTGAGCAGCAGGTGGTCCACAACCCCTTTCAC

CATCCCCGCCGCCGTGGAGATATCATCGCGGCTGAGCTTCAACTTCTC

CAAAACCGCCCGGAGCTTCGAGGCCCCAGGCGCCGCATCCCTCCGTAC

GAGAATGGGGCCGAGACCGGCAGGCCGGGGCTGGGCACGTCCCAGGG

CCCGGGCGGRGGTCTTGGCTTCGTGGAGCAGCGCGCGCCCCTCTGGCG

GCAAGAACCAGCCCTGGAAAGAGCCGGCTCCCGAGCCGCAGGAGGCTC

CAGCCCCTCTGCCCCAGGGGCGCTGGTGGCGTCAGACGGCTGCGTGTC

CTGGGCGCGCTGAGGGGCCTTTTTGGCGCGGG<u>CCCCAGTTGCGCGGAC</u>

<u>GGGCGG</u>CCTCTCCTGGGTGTCCGGGGCGCTCTTTTTCTGCCGGGATCC

CGACTTYCTGGCGGGGCCGAACTTTCCCKCCTTAGGCAGG<u>GCGGCCTC</u>

<u>GGGGGCAGCCGGAGACTC</u>GKTGGGATCCATCGGGGCGCCCCTGGCATT

CCGTGCGGAAGCCTTGGGGGCAGTGGCTCCGGCCTCGGAAGCTCTCTG

CAYGGCCTTTCCGTGCCAAGGCTGCATGGCTGGCGCTTTCTGTTCCCC

GAAAGAAGAATCCGTTTCAGGAAAAGGCCGCAAGAGGAAGAGCCAGCA

GCAGCTGTTGGAAACCAAGCACTACTGGCGGGCACACAAGAGTCTGCG

ACCCGAAGGGGAACCCCAGGCTGGGAAGTCGCTGGGAGCCACGCCCAT

GCCGCGAAGAGGCTGGCCGCGGCCTTTCCTGAGGCTACAAAAGTCTCG

AA<u>GT</u>

SEQ ID NO: 11
Corresponds to the bisulfite converted product of a fully methylated form of SEQ ID NO: 10.

(SEQ ID NO: 11)
ATCGTTGGATGTGTAGATGAATAAACGAACGGTTTGTCGTTTTATTTA

GATTAGGTTATCGAAAAATATGTAAAAGTTTAAGTTATTTTCGAAGGG

AAGTGAGGGGCGCGATTCGGGGAAGGTAGGGATTGCGGATTGCGGAAG

GTCGAGTAGCGGGGTTCGGCGGGAGGGCGTTAAGTAGTTTATTTTTAC

-continued

```
GTGTTTATAGTAGTTTTCGGTGTTTAGTAGTTCGACGTTTTTGAACGC
GGAGTCGTATTTTAGTTTGAGTAGTAGGTGGTTTATAATTTTTTTTAT
TATTTTCGTCGTCGTGGAGATATTATCGCGGTTGAGTTTTAATTTTTT
TAAAATCGTTCGGAGTTTCGAGGTTTTAGGCGTCGTATTTTTCGTAC
GAGAATGGGGGTCGAGATCGGTAGGTCGGGGTTGGGTACGTTTTAGGG
TTCGGGCGGRGGTTTTGGTTTCGTGGAGTAGCGCGCGTTTTTTTGGCG
GTAAGAATTAGTTTTGGAAAGAGTCGGTTTTCGAGTCGTAGGAGGTTT
TAGTTTTTTTGTTTTAGGGGCGTTGGTGGCGTTAGACGGTTGCGTGTT
TTGGGCGCGTTGAGGGGTTTTTTTGGCGCGGGTTTTAGTTGCGCGGAC
GGGCGGTTTTTTTTGGGTGTTCGGGGCGTTTTTTTTTTGTCGGGATTT
CGATTTCTTGGCGGGGTCGAATTTTTTTKTTTTAGGTAGGGCGGTTTC
GGGGGTAGTCGGAGATTCGKTGGGATTTATCGGGGCGTTTTTGGTATT
TCGTGCGGAAGTTTTGGGGGTAGTGGTTTCGGTTTCGGAAGTTTTTG
TACGGTTTTTTCGTGTTAAGGTTGTATGGTTGGCGTTTTTTGTTTTTC
GAAAGAAGAATTCGTTTTAGGAAAAGGTCGTAAGAGGAAGAGTTAGTA
GTAGTTGTTGGAAATTAAGTATTATTGGCGGGTATATAAGAGTTTGCG
ATTCGAAGGGGAATTTTAGGTTGGGAAGTCGTTGGGAGTTACGTTTAT
GTCGCGAAGAGGTTGGTCGCGGTTTTTTTGAGGTTATAAAAGTTTCG
AAGT
```

SEQ ID NO: 12
Corresponds to the bisulfite converted product of a fully unmethylated from of SEQ ID NO: 10.

```
                                            (SEQ ID NO: 12)
ATTGTTGGATGTGTAGATGAATAAATGAATGGTTTGTTGTTTTATTTA

GATTAGGTTATTGAAAAATATGTAAAAGTTTAAGTTATTTTTGAAGGG

AAGTGAGGGGTGTGATTTGGGGAAGGTAGGGATTGTGGATTGTGGAAG

GTTGAGTAGTGGGGTTTGGTGGGAGGGTGTTAAGTAGTTTATTTTTAT

GTGTTTATAGTAGTTTTGGTGTTTAGTAGTTTGATGTTTTTGAATGT

GGAGTTGTATTTTAGTTTGAGTAGTAGGTGGTTTATAATTTTTTTTAT

TATTTTTGTTGTTGTGGAGATATTATTGTGGTTGAGTTTTAATTTTTT

TAAAATTGTTTGGAGTTTTGAGGTTTTAGGTGTTGTATTTTTTTGTAT

GAGAATGGGGGTTGAGATTGGTAGGTTGGGGTTGGGTATGTTTTAGGG

TTTGGGTGGRGGTTTTGGTTTTGTGGAGTAGTGTGTGTTTTTTGGTG

GTAAGAATTAGTTTTGGAAAGAGTTGGTTTTGAGTTGTAGGAGGTTT

TAGTTTTTTTGTTTTAGGGGTGTTGGTGGTGTTAGATGGTTGTGTGTT

TTGGGTGTGTTGAGGGGTTTTTTTGGTGTGGGTTTTAGTTGTGTGGAT

GGGTGGTTTTTTTGGGTGTTTGGGGTGTTTTTTTTTGTTGGGATTT

TGATTTTTTGGTGGGGTTGAATTTTTTTKTTTTAGGTAGGGTGGTTTT

GGGGGTAGTTGGAGATTTGKTGGGATTTATTGGGGTGTTTTGGTATT

TTGTGTGGAAGTTTTGGGGGTAGTGGTTTTGGTTTTGGAAGTTTTTG

TATGGTTTTTTGTGTTAAGGTTGTATGGTTGGTGTTTTTGTTTTTT
```

```
GAAAGAAGAATTTGTTTTAGGAAAAGGTTGTAAGAGGAAGAGTTAGTA

GTAGTTGTTGGAAATTAAGTATTATTGGTGGGTATATAAGAGTTTGTG

ATTTGAAGGGGAATTTTAGGTTGGGAAGTTGTTGGGAGTTATGTTTAT

GTTGTGAAGAGGTTGGTTGTGGTTTTTTTGAGGTTATAAAAGTTTTG

AAGT
```

SEQ ID NO: 13
Represents the C6Orf150 MSP8 target domain, as aligned to the genomic (−) strand and the C6Orf150 sense strand. This region also corresponds to a subregion within SEQ ID NO: 1 (see FIGS. 14A and B depicting SEQ ID NO: 1, the region beginning at the first red and underlined base through the last red and underlined based, 5' to 3', inclusive, of the highlighted region). The sequence is 130 bp, with bp1=genomic bp 74,218,520 (hg18) and bp130=genomic bp 74,218,391 (hg18).

```
                                            (SEQ ID NO: 13)
GAGTCTCCGGCTGCCCCCGAGGCCGCCCTGCCTAAGGMGGGAAAGTTC

GGCCCCGCCAGRAAGTCGGGATCCCGGCAGAAAAAGAGCGCCCCGGAC

ACCCAGGAGAGGCCGCCCGTCCGCGCAACTGGGG
```

SEQ ID NO: 14
Corresponds to the bisulfite converted product of a fully methylated form of SEQ ID NO: 13.

```
                                            (SEQ ID NO: 14)
GAGTTTTCGGTTGTTTTCGAGGTCGTTTTGTTTAAGGMGGGAAAGTTC

GGTTTCGTTAGRAAGTCGGGATTTCGGTAGAAAAAGAGCGTTTCGGAT

ATTTAGGAGAGGTCGTTCGTTCGCGTAATTGGGG
```

SEQ ID NO: 15
Corresponds to the bisulfite converted product of a fully unmethylated form of SEQ ID NO: 15.

```
                                            (SEQ ID NO: 15)
GAGTTTTTGGTTGTTTTTGAGGTTGTTTTGTTTAAGGMGGGAAAGTTT

GGTTTTGTTAGRAAGTTGGGATTTTGGTAGAAAAAGAGTGTTTTGGAT

ATTTAGGAGAGGTTGTTTGTTTGTGTAATTGGGG
```

SEQ ID NO: 16
Represents the C6Orf150 MSP8 target domain, as aligned to the genomic (+) strand and the C6Orf150 anti-sense strand. This region also corresponds to a subregion within SEQ ID NO: 4 (see FIGS. 15A and B depicting SEQ ID NO: 4, the region beginning at the first red and underlined base through the last red and underlined based, 5' to 3', inclusive, of the highlighted region). The sequence is 130 bp, with bp1=genomic bp 74,218,391 (hg18) and bp130=genomic 74,218,520 (hg18).

```
                                            (SEQ ID NO: 16)
CCCCAGTTGCGCGGACGGGCGGCCTCTCCTGGGTGTCCGGGGCGCTCT

TTTTCTGCCGGGATCCCGACTTYCTGGCGGGGCCGAACTTTCCCKCCT

TAGGCAGGGCGGCCTCGGGGGCAGCCGGAGACTC
```

SEQ ID NO: 17
Corresponds to the bisulfite converted product of a fully methylated form of SEQ ID NO: 16.

(SEQ ID NO: 17)
<u>TTTTAGTTGCGCGGACGGGCGG</u>TTTTTTTTGGGTGTTCGGGGCGTTTT
TTTTTTGTCGGGATTTCGATTTCTTGGCGGGGTCGAATTTTTTTKTTT
TAGGTAGGG<u>GCGGTTTCGGGGGTAGTCGGAGATTC</u>

SEQ ID NO: 18
Corresponds to the bisulfite converted product of a fully unmethylated form of SEQ ID NO: 16.

(SEQ ID NO: 18)
<u>TTTTAGTTGTGTGGATGGGTGG</u>TTTTTTTTGGGTGTTTGGGGTGTTTT
TTTTTTGTTGGGATTTTGATTTTTTGGTGGGGTTGAATTTTTTTKTTT
TAGGTAGG<u>GTGGTTTTGGGGGTAGTTGGAGATTT</u>

We claim:

1. A method for detecting the likelihood that a human patient has a gastrointestinal neoplasia, comprising:
   a) obtaining a human sample;
   b) assaying said sample for the presence or absence of methylation within a nucleotide sequence set forth in SEQ ID NOs: 2 or 5, or fragments thereof, wherein the fragment thereof contains at least one site of methylation and is of a length amenable to methylation specific-PCR and/or digestion by a methylation-sensitive restriction enzyme; wherein the presence of methylation within any one of said nucleotide sequences is indicative of the likelihood that the human patient has colon neoplasia;
   c) wherein if said patient is determined to be likely to have said colon neoplasia, treating said patient with a drug that targets said colon neoplasia.

2. The method of claim 1, wherein the gastrointestinal neoplasia is a colon neoplasia.

3. The method of claim 1, wherein the sample is a bodily fluid selected from blood, serum, plasma, a blood-derived fraction, stool, urine, and a colonic effluent.

4. The method of claim 1, wherein the assay is methylation-specific PCR.

5. The method of claim 4, wherein said step b) comprises:
   i) treating DNA from the sample to convert non-methylated cytosine bases in the DNA to a different base;
   ii) amplifying a region of the converted C6Orf150 nucleotide sequence with a forward primer and a reverse primer; and
   iii) analyzing the methylation patterns of said C6Orf150 nucleotide sequences.

6. The method of claim 4, wherein said step b) comprises:
   i) treating DNA from the sample to convert non-methylated cytosine bases in the DNA to a different base;
   ii) amplifying a region of the converted C6Orf150 nucleotide sequence with a forward primer and a reverse primer; and
   iii) detecting the presence and/or amount of the amplified product.

7. The method of claim 6, wherein the DNA is treated with a bisulfite compound.

8. The method of claim 4, wherein the forward primers are selected from SEQ ID NOs: 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, and 137.

9. The method of claim 4, wherein the reverse primers are selected from SEQ ID NOs: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, and 138.

10. The method of claim 4, wherein the method comprises PCR primer pairs selected from MSP8 (SEQ ID NOs: 31 and 32), MSP10 (SEQ ID NOs: 35 and 36), and MSP23 (SEQ ID NOs: 61 and 62).

11. The method of claim 10, wherein the primer pair is MSP8 (SEQ ID NOs: 31 and 32).

12. The method of claim 1, wherein the assay comprises using a methylation-specific restriction enzyme.

13. The method of claim 12, wherein said methylation-specific restriction enzyme is selected from HpaII, SmaI, SacII, EagI, MspI, BstUI, and BssHII.

14. The method of claim 12, further comprising a pair of primers selected from SEQ ID NOs: 139, 140, 141, 142, 143, 144, 145, and 146.

15. The method of claim 1, wherein if said patient is determined to be likely to have said colon neoplasia, said patient is treated with a methylation suppressive agent.

16. The method of claim 1, wherein the fragment thereof is 20-3000 nucleotides in length.

17. A method for detecting the likelihood that a human subject has colon neoplasia, comprising:
   a) detecting C6Orf150 protein or nucleic acid expression level in a sample from the human subject, wherein reduced expression level of C6Orf150 protein or nucleic acid relative to a control sample from a healthy subject is indicative of the likelihood that the human subject has colon neoplasia;
   b) wherein if said patient is determined to be likely to have said colon neoplasia, treating said patient with a drug that targets said colon neoplasia.

18. The method of claim 17, wherein if said patient is determined to be likely to have said colon neoplasia, said patient is treated with a methylation suppressive agent.

19. A method for identifying an agent which enhances C6Orf150 protein or nucleic acid expression in a diseased cell associated with C6Orf150 gene silencing, comprising:
   a) contacting the cell with a sufficient amount of the agent under suitable conditions;
   b) quantitatively determining the amount of C6Orf150 protein or nucleic acid; and
   c) comparing the amount of C6Orf150 protein or nucleic acid with the amount of C6Orf150 protein or nucleic acid in the absence of the agent, wherein a greater amount of C6Orf150 protein or nucleic acid in the presence of the agent than in the absence of the agent indicates that the agent enhances C6Orf150 protein or nucleic acid expression.

20. A method for monitoring over time colon neoplasia in a human subject, comprising:
   a) detecting the methylation status of a C6Orf150 nucleotide sequence selected from SEQ ID NOs: 2 or 5 or fragments thereof in a sample from the human subject for a first time; wherein said fragment thereof contains at least one site of methylation and is of a length amenable to methylation specific-PCR and/or digestion by a methylation-sensitive restriction enzyme; and
   b) detecting the methylation status of any one of said C6Orf150 nucleotide sequence of step (a) in a sample from the same human subject at a later time;
   wherein absence of methylation in the C6Orf150 nucleotide sequence taken at a later time and presence of methylation in the C6Orf150 nucleotide sequence taken at the first time is indicative of regression of colon neoplasia; and
   wherein presence of methylation in the C6Orf150 nucleotide sequence taken at a later time and absence of methylation in the C6Orf150 nucleotide sequence taken at the first time is indicative of progression of colon neoplasia;
   c) wherein if said patient is determined to be likely to have said colon neoplasia, treating said patient with a drug that targets said colon neoplasia.

21. The method of claim 20, wherein if said patient is determined to be likely to have said colon neoplasia, said patient is treated with a methylation suppressive agent.

22. The method of claim 20, wherein the fragment thereof is 20-3000 nucleotides in length.

23. A method for detecting colon cancer, comprising:
   a) obtaining a sample from a patient; and
   b) assaying said sample for the presence of methylation of nucleotide sequences within C6Orf150 and vimentin;

wherein methylation of nucleotide sequences within both C6Orf150 and vimentin is indicative of colon cancer;

c) wherein if said patient is found to have colon cancer, treating said patient with a drug that targets said colon cancer.

24. The method of claim 23, wherein if said patient is found to have colon cancer, treating said patient with a methylation suppressive agent.

* * * * *

```
                        SEQUENCE LISTING

<160> NUMBER OF SEQ ID NOS: 154

<210> SEQ ID NO 1
<211> LENGTH: 4000
<212> TYPE: DNA
<213> ORGANISM: Homo sapiens

<400> SEQUENCE: 1
agattgcgcc cccctaactc aaaccaaaat taaatttaaa aaaactttca cttgaaagag        60
aaaagtttct ctgtcaatgt ttttgttttg ttttgttttg ttttgtgatg gactcttttt       120
ctgttgccca ggctggagtg cagtggcgcg atctcggctc actgcaacct ctgcctcccg       180
ggttcaagca gttctctgtc tcggcctccc gagtagatgg gactacaggc gccaccaagc       240
ccggctaatt ttttgtattt ttagtagaga cggggtttca ccatgttggc caggaaggtc       300
tcgatgtctt ggcctcgtga tccgcccgcc tcggcctccc aaactgctga gattacaggc       360
gtgagccacc acgcctggcc tcttttttctt ttttgagaca gagtctcgct ctgtcgccca       420
ggctggagtg aagtggcacg tctcagctca ctgcaacctc crcctcccgg gttcaagtga       480
ttctccagcc tcagcctccc gagtagctgg gattacaggt gcccgccacc acgcctagct       540
aatatttgta tttttttagta gagacggggt ttctttcgcc ttgttggcca ggctggtctt       600
gaactcctga cctcaggtga tccgcccacc tcggtctccc agattgctgg gattacaggc       660
gtgagtcagt gtgcccaggc aacacacaca cacacatata tttaattata agaaagacca       720
ggtcttgctg ggttgcccag gctggtctca aactcctgag ctcaagcgac ccgcctgcct       780
cggcctctcg gatgctgagg ttacaggcgt gagccaccgc gcccggccct acctcatctt       840
cttaagacag gggcacggat tgcctggaga gttagaaact tcgagacttt tgtagcctca       900
ggaaaggccg cggccagcct cttcgcggca tgggcgtggc tcccagcgac ttcccagcct       960
ggggttcccc ttcgggtcgc agactcttgt gtgcccgcca gtagtgcttg gtttccaaca      1020
gctgctgctg gctcttcctc ttgcggcctt ttcctgaaac ggattcttct ttcggggaac      1080
agaaagcgcc agccatgcag ccttggcacg gaaaggccrt gcagagagct tccgaggccg      1140
gagccactgc ccccaaggct tccgcacgga atgccagggg cgccccgatg gatcccamcg      1200
agtctccggc tgcccccgag gccgccctgc ctaaggmggg aaagttcggc cccgccagra      1260
agtcgggatc ccggcagaaa aagagcgccc cggacaccca ggagaggccg cccgtccgcg      1320
caactggggc ccgcgccaaa aaggcccctc agcgcgccca ggacacgcag ccgtctgacg      1380
ccaccagcgc ccctggggca gaggggctgg agcctcctgc ggctcgggag ccggctcttt      1440
ccagggctgg ttcttgccgc cagaggggcg cgcgctgctc cacgaagcca agaccyccgc      1500
ccgggccctg gacgtgccc agcccggcc tgccggtctc ggccccccatt ctcgtacgga      1560 gggatgcggc gcctggggcc tcgaagctcc gggcggtttt ggagaagttg aagctcagcc      1620
```

```
gcgatgatat ctccacggcg gcggggatgg tgaaaggggt tgtggaccac ctgctgctca    1680
gactgaagtg cgactccgcg ttcagaggcg tcgggctgct gaacaccggg agctactatg    1740
agcacgtgaa ggtgagctgc ttggcgccct cccgccgagc ccgctgctc ggccttccgc     1800
aatccgcagt ccctaccttc cccggtcgc gcccctcact tcccttcgga agtaacttag     1860
acttttgcat gttttcggt agcctagtct aagtaaaacg acaaaccgtt cgtttattca     1920
tctacacatc caacgatcag acaaccaacc ggtactgatt gctggctaat ttcaagacac    1980
tgctcccggg ggaattcaaa tgtatgggtt cattcatgca agccgacatg tatcgagttt    2040
ccgtaacagg gcagtgtttg atggtgtgga cctgaggtcc cgagtcagat attgacttgg    2100
ataatttgaa gtggtctgtt aaaaattcca cgtagacttt ttcctatgag gaagacctct    2160
tactccatag aaaaaagat cttcagtttc tctccccctc ttcctccctg cccctctcc     2220
tgctatcccg tctgaccca atttctttt tttctttttt cttttctttt ctttttttt      2280
tttttgagg cggagtctcg ctgcgtcccc caggctggag tgcagtggcg ctatctcggc    2340
tcactgcaag ctccgcctcc cgggttcacg ccattctcct gcctcagctt cccgagtagc   2400
tgggactaca ggcgcccgcc accatgcccg gctaattttt tttgtatttt tagtagagac    2460
ggtgtttcac cgtgttagcc aggatggtct cgatctcctg acctcttgat cgctcgtct    2520
cggcctctca aagtgctggg attacaggcg tsagctaccg cgcccggccg tctgtcccca    2580
gtttcttaca cagaaatcat gggaagctta cagtataatg ttaaacaaac aaataagaat    2640
atctcctaca gatactaaaa cgcttttctag atacacattc cgtataattg cttcgacgtg   2700
tgtattacac agctccatt gcttgtgggt gattgagtca ttaatcattc ctgtgtaaat    2760
tgaaagttta gaagcaggtt cctgactgga gcgtgtttct tgcccagcaa gagatttgtt    2820
tcttttcctt tttctttctt tctttcttt tttttttt gagacggagt ttcgctcttg      2880
ttacccaggc tggagtgcaa tggcgcgatc tcagctcacc tcaacctcca cctcccaggt   2940
tcaagcgatt ctcctgtctc agcctcctga gtagatggga ttacaagcat gagcctccac    3000
cctggctaat tttgtatttt tagtagagac gggctttctc catgttggtc aggctggtct    3060
agaactcccg acctcaggtg atctgccagc ctcagcctcc caaagtgctg ggattacagg    3120
cgtgagccac cacacccggc ttctttctc ttcttttt tcttctcttc tcttctctct     3180
atctctctgt ctctctcttt tcctccctcc ctctcttcct ctctctctct ctctctttat   3240
tttgttcttt ctttcttttc tttcttcttt cttcttttt tgatggagtt tcactcttgt    3300
tgcccaggct gtagtgcagt ggtgccatct aggtttcgct gcaacctccg gcttccaggt    3360
tcaagcgatt ctccwgcttc agccttccaa atagcaggga ttacaggtgc ctgcccccac    3420
tcccggctaa tttatgtatt tttagtagag acggggtttc accatgttgg ccaggctggt   3480
ctcgaactct gacctcagat gatccacctg cctcggcctc cctaagtgct gggattacag    3540
gcttgagcca cggcacccag cccagactgt gtcttgagca tgattctttt taattaacta    3600
atttacttt cagcatcaga tatgtctctg attgagcatg attcttatta tgtaagtatc    3660
aattcagttc aattactgta tatggcgggt ccaaaggaaa aagaaagtta ctagttagaa    3720
ttagagaaca agacattcag aagacagtct ccattcagaa ccactttgtg tgtgtgtgtg    3780
tgtgtgtgtg tgtgtgtgtt tgagacagag tctcactctg tcacccaggc tggagtgcag    3840
tggcgcgatc tcggctcact gcaagccctg cctactgggt tcacaccatt ctcctgcctc    3900
agcctcccaa gtagctggga ctacaggcgc ccgccaccat gcccagctaa ttttttgtatt   3960
tttagtagag acggggtttc accgtgttag ccaggctggt                          4000
```

```
<210> SEQ ID NO 2
<211> LENGTH: 4000
<212> TYPE: DNA
<213> ORGANISM: Homo sapiens

<400> SEQUENCE: 2
agattgcgtt tttttaattt aaattaaaat taaatttaaa aaaattttta tttgaaagag     60
aaaagttttt ttgttaatgt ttttgttttg ttttgttttg ttttgtgatg gattttttt    120 ttgttgttta ggttggagtg tagtggcgcg atttcggttt attgtaattt ttgttttcg    180 ggtttaagta gttttttgtt tcggttttc gagtagatgg gattataggc gttattaagt    240
tcggttaatt ttttgtattt ttagtagaga cggggtttta ttatgttggt taggaaggtt    300
tcgatgtttt ggtttcgtga ttcgttcgtt tcggtttttt aaattgttga gattataggc    360
gtgagttatt acgtttggtt ttttttttt tttgagata gagtttcgtt ttgtcgttta    420
ggttggagtg aagtggtacg ttttagttta ttgtaatttt trttttttcgg gtttaagtga    480 ttttttagtt ttagtttttc gagtagttgg gattataggt gttcgttatt acgtttagtt    540
aatatttgta ttttttagta gagacggggt ttttttcgtt ttgttggtta ggttggtttt    600
gaatttttga ttttaggtga ttcgtttatt tcggtttttt agattgttgg gattataggc    660
gtgagttagt gtgtttaggt aatatatata tatatatata tttaattata agaaagatta    720
ggttttgttg ggttgtttag gttggtttta aattttttgag tttaagcgat tcgtttgttt    780 cggttttttcg gatgttgagg ttataggcgt gagttatcgc gttcggtttt attttatttt    840
tttaagatag gggtacggat tgtttggaga gttagaaatt tcgagatttt tgtagttttta    900 ggaaaggtcg cggttagttt tttcgcggta tgggcgtggt ttttagcgat ttttttagttt    960 ggggttttt ttcgggtcgt agattttgt gtgttcgtta gtagtgtttg gttttttaata   1020 gttgttgttg gtttttttt ttgcggtttt ttttgaaac ggattttttt ttcggggaat   1080
agaaagcgtt agttatgtag ttttggtacg gaaaggttrt gtagagagtt ttcgaggtcg   1140
gagttattgt tttaaggtt ttcgtacgga atgttagggg cgtttcgatg gattttamcg   1200
agttttcggt tgttttcgag gtcgtttttgt ttaaggmggg aaagttcggt ttcgttagra   1260
agtcgggatt tcggtagaaa aagagcgttt cggatattta ggagaggtcg ttcgttcgcg   1320
taattggggt tcgcgttaaa aaggttttt agcgcgttta ggatacgtag tcgtttgacg   1380
ttattagcgt ttttgggta gagggggttgg agttttttgc ggttcgggag tcggtttttt   1440 ttaggggttgg tttttgtcgt tagagggcg cgcgttgttt tacgaagtta agattctcgt   1500
tcgggttttg ggacgtgttt agtttcggtt tgtcggtttc ggtttttatt ttcgtacgga   1560
gggatgcggc gtttggggtt tcgaagtttc gggcggtttt ggagaagttg aagtttagtc   1620
gcgatgatat ttttacggcg gcggggatgg tgaaagggg tgtggattat ttgttgttta   1680
gattgaagtg cgatttcgcg tttagaggcg tcggttttgtt gaatatcggg agttattatg   1740
agtacgtgaa ggtgagttgt ttggcgtttt ttcgtcgagt ttcgttgttc ggttttttcgt   1800 aattcgtagt ttttatttttt ttcgggtcgc gtttttttatt tttttttcgga agtaatttag   1860 attttttgtat gttttttcggt agtttagttt aagtaaaacg ataaatcgtt cgtttattta   1920
tttatatatt taacgattag ataattaatc ggtattgatt gttggttaat tttaagatat   1980
tgttttcggg ggaatttaaa tgtatgggtt tatttatgta agtcgatatg tatcgagttt   2040
tcgtaatagg gtagtgtttg atggtgtgga tttgaggttt cgagttagat attgatttgg   2100
ataatttgaa gtggtttgtt aaaaatttta cgtagatttt tttttatgag gaagattttt   2160
```

-continued

```
tattttatag aaaaaaagat ttttagtttt tttttttttt tttttttttg tttttttttt    2220
tgttatttcg tttgatttta attttttttt tttttttttt tttttttttt tttttttttt    2280 tttttttgagg cggagtttcg ttgcgttttt taggttggag tgtagtggcg ttatttcggt    2340
ttattgtaag tttcgttttt cgggtttacg ttatttttt gttttagttt ttcgagtagt    2400
tgggattata ggcgttcgtt attatgttcg gttaattttt tttgtatttt tagtagagac    2460
ggtgttttat cgtgttagtt aggatggttt cgattttttg atttttgat tcgttcgttt    2520 cggttttta aagtgttggg attataggcg tsagttatcg cgttcggtcg tttgttttta    2580
gttttttata tagaaattat gggaagttta tagtataatg ttaaataaat aaataagaat    2640
attttttata gatattaaaa cgttttttag atatatattt cgtataattg tttcgacgtg    2700
tgtattatat agttttattt gtttgtgggt gattgagtta ttaattattt ttgtgtaaat    2760
tgaaagttta gaagtaggtt tttgattgga gcgtgttttt tgtttagtaa gagatttgtt    2820
tttttttttt tttttttttt tttttttttt tttttttttt gagacggagt ttcgtttttg    2880
ttatttaggt tggagtgtaa tggcgcgatt ttagtttatt ttaattttta ttttttaggt    2940
ttaagcgatt tttttgtttt agttttttga gtagatggga ttataagtat gagttttat    3000 tttggttaat tttgtatttt tagtagagac gggtttttt tatgttggtt aggttggttt    3060
agaattttcg attttaggtg atttgttagt tttagttttt taaagtgttg ggattatagg    3120
cgtgagttat tatattcggt tttttttttt tttttttttt tttttttttt tttttttttt    3180 attttttgt tttttttttt tttttttttt tttttttttt tttttttttt ttttttttat    3240 tttgttttt tttttttttt tttttttttt tttttttttt tgatggagtt ttattttgt    3300 tgtttaggtt gtagtgtagt ggtgttattt aggtttcgtt gtaattttcg gttttaggt    3360 ttaagcgatt ttttwgtttt agttttttaa atagtaggga ttataggtgt ttgttttat    3420 tttcggttaa tttatgtatt tttagtagag acggggtttt attatgttgg ttaggttggt    3480
ttcgaatttt gattttagat gatttatttg tttcggtttt tttaagtgtt gggattatag    3540
gtttgagtta cggtatttag tttagattgt gttttgagta tgatttttt taattaatta    3600 atttatttt tagtattaga tatgttttg attgagtatg atttttatta tgtaagtatt    3660
aatttagttt aattattgta tatggcgggt ttaaaggaaa agaaagtta ttagttagaa    3720 ttagagaata agatatttag aagatagttt ttatttagaa ttattttgtg tgtgtgtgtg    3780
tgtgtgtgtg tgtgtgtgtt tgagatagag ttttattttg ttatttaggt tggagtgtag    3840
tggcgcgatt tcggtttatt gtaagtttg tttattgggt ttatattatt tttttgtttt    3900 agtttttaa gtagttggga ttataggcgt tcgttattat gtttagttaa ttttttgtatt    3960 tttagtagag acggggtttt atcgtgttag ttaggttggt                          4000
```

<210> SEQ ID NO 3
<211> LENGTH: 4000
<212> TYPE: DNA
<213> ORGANISM: Homo sapiens

<400> SEQUENCE: 3

```
agattgtgtt ttttaatttt aaattaaaat taaatttaaa aaaattttta tttgaaagag      60
aaaagttttt ttgttaatgt tttttgtttg ttttgttttg ttttgtgatg gatttttttt     120
ttgttgttta ggttggagtg tagtggtgtg attttggttt attgtaattt ttgttttttg     180
ggtttaagta gttttttgtt ttggtttttt gagtagatgg gattataggt gttattaagt     240
ttggttaatt tttgtatttt ttagtagaga tggggtttta ttatgttggt taggaaggtt     300
```

```
ttgatgtttt ggttttgtga tttgtttgtt ttggtttttt aaattgttga gattataggt    360
gtgagttatt atgtttggtt ttttttttttt ttttgagata gagttttgtt ttgttgttta    420
ggttggagtg aagtggtatg tttagttta ttgtaatttt trtttttttgg gtttaagtga    480 tttttttagtt ttagttttt gagtagttgg gattataggt gtttgttatt atgtttagtt    540
aatatttgta tttttttagta gagatggggt ttttttttgtt ttgttggtta ggttggtttt    600 gaattttttga tttaggtga tttgtttatt tggtttttt agattgttgg gattataggt    660
gtgagttagt gtgtttaggt aatatatata tatatatata tttaattata agaaagatta    720
ggttttgttg ggttgtttag gttggtttta aattttttgag tttaagtgat ttgtttgttt    780 tggtttttttg gatgttgagg ttataggtgt gagttattgt gtttggtttt attttatttt    840
tttaagatag gggtatggat tgtttggaga gttagaaatt ttgagatttt tgtagtttta    900
ggaaaggttg tggttagttt ttttgtggta tgggtgtggt ttttagtgat tttttagttt    960
ggggtttttt tttgggttgt agattttttgt gtgtttgtta gtagtgtttg gttttttaata   1020 gttgttgttg gttttttttt ttgtggtttt tttttgaaat ggattttttt tttggggaat   1080
agaaagtgtt agttatgtag ttttggtatg gaaaggttrt gtagagagtt tttgaggttg   1140
gagttattgt tttaaggtt tttgtatgga atgttagggg tgttttgatg gattttamtg   1200 agttttggt tgttttttgag gttgttttgt ttaaggmggg aaagtttggt tttgttagra   1260
agttgggatt ttggtagaaa aagagtgttt tggatatttta ggagaggttg tttgtttgtg   1320
taattggggt ttgtgttaaa aaggttttttt agtgtgttta ggatatgtag ttgtttgatg   1380
ttattagtgt ttttggggta gagggggttgg agtttttttgt ggtttgggag ttggttttttt   1440 ttagggttgg ttttttgttgt tagagggggtg tgtgttgttt tatgaagtta agattttttgt   1500 ttgggttttg ggatgtgttt agtttggttt tgttggtttt ggttttttatt tttgtatgga   1560 gggatgtggt gtttggggtt ttgaagttttt gggtggtttt ggagaagttg aagtttagtt   1620
gtgatgatat tttattatggtg gtggggatgg tgaaagggggt tgtggattat ttgttgttta   1680
gattgaagtg tgattttgtg tttagaggtg ttgggttgtt gaatattggg agttattatg   1740
agtatgtgaa ggtgagttgt ttggtgtttt tttgttgagt tttgttgttt ggttttttgt    1800
aatttgtagt tttatttttt tttgggttgt gtttttttatt tttttttttgga agtaatttag   1860 atttttgtat gtttttttggt agtttagttt aagtaaaatg ataaattgtt tgtttatttta   1920 tttatatatt taatgattag ataattaatt ggtattgatt gttggttaat tttaagatat   1980 tgttttttggg ggaatttaaa tgtatggggtt tatttatgta agttgatatg tattgagttt   2040 ttgtaataggg gtagtgtttg atggtgtgga tttgaggttt tgagttagat attgatttgg   2100
ataatttgaa gtggtttgtt aaaaatttta tgtagatttt ttttttatgag gaagattttt   2160 tatttttatag aaaaaaagat tttagttttt tttttttttt ttttttttttg ttttttttttt   2220 tgttatttttg tttgatttta atttttttttt ttttttttttt ttttttttttt ttttttttt   2280 tttttttgagg tggagttttg ttgtgttttt taggttggag tgtagtggtg ttattttggt   2340
ttattgtaag ttttgttttt tgggtttatg ttatttttttt gttttagttt ttttgagtagt   2400 tgggattata ggtgtttgtt attatgtttg gttaattttt tttgtatttt tagtagagat   2460
ggtgttttat tgtgttagtt aggatggttt tgatttttg attttttgat ttgtttgttt   2520
tggtttttta aagtgttggg attataggtg tsagttattg tgtttggttg tttgttttta   2580 gtttttttata tagaaattat gggaagttta tagtataatg ttaaataaat aaataagaat   2640
attttttata gatattaaaa tgttttttag atatatattt tgtataattg ttttgatgtg   2700
```

| | |
|---|---|
| tgtattatat agtttttattt gtttgtgggt gattgagtta ttaattattt ttgtgtaaat | 2760 |
| tgaaagttta gaagtaggtt tttgattgga gtgtgttttt tgtttagtaa gagatttgtt | 2820 |
| tttttttttt tttttttttt tttttttttt tttttttttt gagatggagt tttgtttttg | 2880 |
| ttatttaggt tggagtgtaa tggtgtgatt ttagtttatt ttaattttta tttttttaggt | 2940 |
| ttaagtgatt ttttttgtttt agtttttttga gtagatggga ttataagtat gagtttttat | 3000 |
| tttggttaat tttgtatttt tagtagagat gggtttttttt tatgttggtt aggttggttt | 3060 |
| agaattttttg atttttaggtg atttgttagt tttagttttt taaagtgttg ggattatagg | 3120 |
| tgtgagttat tatatttggt tttttttttt tttttttttt tttttttttt tttttttttt | 3180 |
| atttttttgt tttttttttt tttttttttt tttttttttt tttttttttt ttttttttat | 3240 |
| tttgtttttt tttttttttt tttttttttt tttttttttt tgatggagtt ttattttttgt | 3300 |
| tgtttaggtt gtagtgtagt ggtgttatttt aggttttgtt gtaattttttg gttttttaggt | 3360 |
| ttaagtgatt ttttwgtttt agtttttttaa atagtaggga ttataggtgt ttgttttttat | 3420 |
| ttttggttaa tttatgtatt tttagtagag atggggtttt attatgttgg ttaggttggt | 3480 |
| tttgaattttt gattttagat gatttatttg ttttggttttt tttaagtgtt gggattatag | 3540 |
| gtttgagtta tggtatttag tttagattgt gttttgagta tgattttttt taattaatta | 3600 |
| atttatttttt tagtattaga tatgtttttg attgagtatg atttttatta tgtaagtatt | 3660 |
| aatttagttt aattattgta tatggtgggt ttaaaggaaa agaaagtta ttagttagaa | 3720 |
| ttagagaata agatatttag aagatagttt ttatttagaa ttatttttgtg tgtgtgtgtg | 3780 |
| tgtgtgtgtg tgtgtgtgtt tgagatagag ttttattttg ttatttaggt tggagtgtag | 3840 |
| tggtgtgatt ttggtttatt gtaagttttg tttattgggt ttatattatt ttttttgtttt | 3900 |
| agttttttaa gtagttggga ttataggtgt ttgttattat gtttagttaa tttttgtatt | 3960 |
| tttagtagag atggggtttt attgtgttag ttaggttggt | 4000 |

<210> SEQ ID NO 4
<211> LENGTH: 4000
<212> TYPE: DNA
<213> ORGANISM: Homo sapiens

<400> SEQUENCE: 4

| | |
|---|---|
| accagcctgg ctaacacggt gaaacccccgt ctctactaaa aatacaaaaa ttagctgggc | 60 |
| atggtggcgg gcgcctgtag tcccagctac ttgggaggct gaggcaggag aatggtgtga | 120 |
| acccagtagg cagggcttgc agtgagccga gatcgcgcca ctgcactcca gcctgggtga | 180 |
| cagagtgaga ctctgtctca aacacacaca cacacacaca cacacacaca cacaaagtgg | 240 |
| ttctgaatgg agactgtctt ctgaatgtct tgttctctaa ttctaactag taactttctt | 300 |
| tttcctttgg acccgccata tacagtaatt gaactgaatt gatacttaca taataagaat | 360 |
| catgctcaat cagagacata tctgatgctg aaaagtaaat tagttaatta aaaagaatca | 420 |
| tgctcaagac acagtctggg ctgggtgccg tggctcaagc ctgtaatccc agcacttagg | 480 |
| gaggccgagg caggtggatc atctgaggtc agagttcgag accagcctgg ccaacatggt | 540 |
| gaaacccccgt ctctactaaa aatacataaa ttagccggga gtggggcag gcacctgtaa | 600 |
| tccctgctat ttggaaggct gaagcwggag aatcgcttga acctggaagc cggaggttgc | 660 |
| agcgaaacct agatggcacc actgcactac agcctgggca acaagagtga aactccatca | 720 |
| aaaaaagaag aaagaagaaa gaaaagaaag aaagaacaaa ataaagagag agagagagag | 780 |
| aggaagagag ggagggagga aaagagagag acagagagat agagagaaga gaagagaaga | 840 |

```
gaaaaaagaa gagaaaagaa gccgggtgtg gtggctcacg cctgtaatcc cagcactttg    900
ggaggctgag gctggcagat cacctgaggt cgggagttct agaccagcct gaccaacatg    960
gagaaagccc gtctctacta aaaatacaaa attagccagg gtggaggctc atgcttgtaa   1020
tcccatctac tcaggaggct gagacaggag aatcgcttga acctgggagg tggaggttga   1080
ggtgagctga gatcgcgcca ttgcactcca gcctgggtaa caagagcgaa actccgtctc   1140
aaaaaaaaaa aaaagaaaga aagaaagaaa agaaaaaga aacaaatctc ttgctgggca    1200
agaaacacgc tccagtcagg aacctgcttc taaactttca atttacacag gaatgattaa   1260
tgactcaatc acccacaagc aaatggagct gtgtaataca cacgtcgaag caattatacg   1320
gaatgtgtat ctagaaagcg ttttagtatc tgtaggagat attcttattt gtttgtttaa   1380
cattatactg taagcttccc atgatttctg tgtaagaaac tggggacaga cggccgggcg   1440
cggtagctsa cgcctgtaat cccagcactt tgagaggccg agacgagcga atcaagaggt   1500
caggagatcg agaccatcct ggctaacacg gtgaaacacc gtctctacta aaaatacaaa   1560
aaaaattagc cgggcatggt ggcgggcgcc tgtagtccca gctactcggg aagctgaggc   1620
aggagaatgg cgtgaacccg ggaggcggag cttgcagtga ccgagatag cgccactgca    1680
ctccagcctg ggggacgcag cgagactccg cctcaaaaaa aaaaaaaag aaaagaaaag    1740
aaaaaagaaa aaaagaaat tggggtcaga cgggatagca ggagagggg cagggaggaa     1800
gaggggggaga gaaactgaag atcttttttt ctatggagta agaggtcttc ctcataggaa  1860
aaagtctacg tggaattttt aacagaccac ttcaaattat ccaagtcaat atctgactcg   1920
ggacctcagg tccacaccat caaacactgc cctgttacgg aaactcgata catgtcggct   1980
tgcatgaatg aacccataca tttgaattcc cccgggagca gtgtcttgaa attagccagc   2040
aatcagtacc ggttggttgt ctgatcgttg gatgtgtaga tgaataaacg aacggtttgt   2100
cgttttactt agactaggct accgaaaaac atgcaaaagt ctaagttact tccgaaggga   2160
agtgaggggc gcgacccggg gaaggtaggg actgcggatt gcggaaggcc gagcagcggg   2220
gctcggcggg agggcgccaa gcagctcacc ttcacgtgct catagtagct cccggtgttc   2280
agcagcccga cgcctctgaa cgcggagtcg cacttcagtc tgagcagcag gtggtccaca   2340
accccttttca ccatccccgc cgccgtggag atatcatcgc ggctgagctt caacttctcc  2400
aaaaccgccc ggagcttcga ggccccaggc gccgcatccc tccgtacgag aatgggggcc   2460
gagaccggca ggccggggct gggcacgtcc cagggcccgg gcggrggtct tggcttcgtg   2520
gagcagcgcg cgccctctg gcggcaagaa ccagccctgg aaagagccgg ctcccgagcc    2580
gcaggaggct ccagcccctc tgccccaggg gcgctggtgg cgtcagacgg ctgcgtgtcc   2640
tgggcgcgct gagggccttt tttgcgcgcg gccccagttg cgcggacggg cggcctctcc   2700
tgggtgtccg gggcgctctt tttctgccgg gatcccgact tyctggcggg gccgaacttt   2760
ccckccttag gcagggcggc ctcggggcca gccgagact cgktgggatc catcggggcg    2820
cccctggcat tccgtgcgga agccttgggg gcagtggctc cggcctcgga agctctctgc   2880
ayggcctttc cgtgccaagg ctgcatggct ggcgctttct gttccccgaa agaagaatcc   2940
gtttcaggaa aaggccgcaa gaggaagagc cagcagcagc tgttggaaac caagcactac   3000
tggcgggcac acaagagtct gcgacccgaa ggggaacccc aggctgggaa gtcgctggga   3060
gccacgccca tgccgcgaag aggctggccg cggcctttcc tgaggctaca aaagtctcga   3120
agtttctaac tctccaggca atccgtgccc ctgtcttaag aagatgaggt agggccgggc   3180
gcggtggctc acgcctgtaa cctcagcatc cgagaggccg aggcaggcgg gtcgcttgag   3240
```

| ctcaggagtt | tgagaccagc | ctgggcaacc | cagcaagacc | tggtctttct | tataattaaa | 3300 |
| tatatgtgtg | tgtgtgtgtt | gcctgggcac | actgactcac | gcctgtaatc | ccagcaatct | 3360 |
| gggagaccga | ggtgggcgga | tcacctgagg | tcaggagttc | aagaccagcc | tggccaacaa | 3420 |
| ggcgaaagaa | accccgtctc | tactaaaaaa | tacaaatatt | agctaggcgt | ggtggcgggc | 3480 |
| acctgtaatc | ccagctactc | gggaggctga | ggctggagaa | tcacttgaac | ccgggaggyg | 3540 |
| gaggttgcag | tgagctgaga | cgtgccactt | cactccagcc | tgggcgacag | agcgagactc | 3600 |
| tgtctcaaaa | aagaaaaaga | ggccaggcgt | ggtggctcac | gcctgtaatc | tcagcagttt | 3660 |
| gggaggccga | ggcgggcgga | tcacgaggcc | aagacatcga | gaccttcctg | gccaacatgg | 3720 |
| tgaaaccccg | tctctactaa | aaatacaaaa | aattagccgg | gcttggtggc | gcctgtagtc | 3780 |
| ccatctactc | gggaggccga | gacagagaac | tgcttgaacc | cggggaggcag | aggttgcagt | 3840 |
| gagccgagat | cgcgccactg | cactccagcc | tgggcaacag | aaaaagagtc | catcacaaaa | 3900 |
| caaaacaaaa | caaaacaaaa | acattgacag | agaaactttt | ctctttcaag | tgaaagtttt | 3960 |
| tttaaattta | attttggttt | gagttagggg | ggcgcaatct |           |           | 4000 |

<210> SEQ ID NO 5
<211> LENGTH: 4000
<212> TYPE: DNA
<213> ORGANISM: Homo sapiens

<400> SEQUENCE: 5

| attagtttgg | ttaatacggt | gaaatttcgt | ttttattaaa | aatataaaaa | ttagttgggt |   60 |
| atggtggcgg | gcgtttgtag | ttttagttat | ttgggaggtt | gaggtaggag | aatggtgtga |  120 |
| atttagtagg | tagggtttgt | agtgagtcga | gatcgcgtta | ttgtatttta | gtttgggtga |  180 |
| tagagtgaga | ttttgtttta | aatatatata | tatatatata | tatatatata | tataaagtgg |  240 |
| ttttgaatgg | agattgtttt | ttgaatgttt | tgttttttaa | ttttaattag | taattttttt |  300 |
| ttttttttgg | attcgttata | tatagtaatt | gaattgaatt | gatatttata | taataagaat |  360 |
| tatgtttaat | tagagatata | tttgatgttg | aaaagtaaat | tagttaatta | aaaagaatta |  420 |
| tgtttaagat | atagtttggg | ttgggtgtcg | tggtttaagt | ttgtaatttt | agtatttagg |  480 |
| gaggtcgagg | taggtggatt | atttgaggtt | agagttcgag | attagtttgg | ttaatatggt |  540 |
| gaaatttcgt | ttttattaaa | aatatataaa | ttagtcggga | gtgggggtag | gtatttgtaa |  600 |
| tttttgttat | ttggaaggtt | gaagtwggag | aatcgtttga | atttggaagt | cggaggttgt |  660 |
| agcgaaattt | agatggtatt | attgtattat | agtttgggta | ataagagtga | aattttatta |  720 |
| aaaaaagaag | aaagaagaaa | gaaaagaaag | aagaataaaa | ataaagagag | agagagagag |  780 |
| aggaagagag | ggagggagga | aaagagagag | atagagagat | agagagaaga | gaagagaaga |  840 |
| gaaaaaagaa | gagaaaagaa | gtcgggtgtg | gtggtttacg | tttgtaattt | tagtattttg |  900 |
| ggaggttgag | gttggtagat | tatttgaggt | cgggagtttt | agattagttt | gattaatatg |  960 |
| gagaaagttc | gttttattta | aaaatataaa | attagttagg | gtggaggttt | atgtttgtaa | 1020 |
| ttttatttat | ttaggaggtt | gagataggag | aatcgtttga | atttgggagg | tggaggttga | 1080 |
| ggtgagttga | gatcgcgtta | ttgtatttta | gtttgggtaa | taagagcgaa | atttcgtttt | 1140 |
| aaaaaaaaaa | aaaagaaaga | aagaagaaa | agaaaaaga | aataaatttt | ttgttgggta | 1200 |
| agaaatacgt | tttagttagg | aatttgtttt | taaatttta | atttatatag | gaatgattaa | 1260 |
| tgatttaatt | atttataagt | aaatggagtt | gtgtaatata | tacgtcgaag | taattatacg | 1320 |
| gaatgtgtat | ttagaaagcg | ttttagtatt | tgtaggagat | attttatttt | gtttgtttaa | 1380 |

```
tattatattg taagttttt atgatttttg tgtaagaaat tggggataga cggtcgggcg      1440
cggtagttsa cgtttgtaat tttagtattt tgagaggtcg agacgagcga attaagaggt      1500
taggagatcg agattatttt ggttaatacg gtgaaatatc gttttattat aaaatataaa      1560
aaaaattagt cgggtatggt ggcgggcgtt tgtagtttta gttattcggg aagttgaggt      1620
aggagaatgg cgtgaattcg ggaggcggag tttgtagtga gtcgagatag cgttattgta      1680
ttttagtttg ggggacgtag cgagatttcg ttttaaaaaa aaaaaaaaag aaaagaaaag      1740
aaaaagaaa aaaagaaat tggggttaga cgggatagta ggagaggggg tagggaggaa        1800
gagggggaga gaaattgaag attttttttt ttatggagta agaggttttt tttataggaa      1860
aaagtttacg tggaatttt aatagattat tttaaattat ttaagttaat atttgattcg       1920
ggatttagg tttatattat taaatattgt tttgttacgg aaattcgata tatgtcggtt       1980
tgtatgaatg aatttatata tttgaattt ttcgggagta gtgttttgaa attagttagt       2040
aattagtatc ggttggttgt ttgatcgttg gatgtgtaga tgaataaacg aacggtttgt      2100
cgttttattt agattaggtt atcgaaaaat atgtaaaagt ttaagttatt ttcgaaggga      2160
agtgaggggc gcgattcggg gaaggtaggg attgcggatt gcggaaggtc gagtagcggg      2220
gttcggcggg agggcgttaa gtagtttatt tttacgtgtt tatagtagtt ttcggtgttt      2280
agtagttcga cgttttgaa cgcggagtcg tattttagtt tgagtagtag gtggtttata      2340
atttttttta ttatttcgt cgtcgtggag atattatcgc ggttgagttt taattttttt      2400
aaaatcgttc ggagtttcga ggttttaggc gtcgtatttt ttcgtacgag aatgggggtc      2460
gagatcggta ggtcggggtt gggtacgttt tagggttcgg gcggrggttt tggtttcgtg      2520
gagtagcgcg cgtttttttg gcggtaagaa ttagttttgg aaagagtcgg ttttcgagtc      2580
gtaggaggtt ttagttttt tgtttttaggg gcgttggtgg cgttagacgg ttgcgtgttt      2640
tgggcgcgtt gagggttt tttggcgcg gttttagttg cgcggacggg cggttttttt        2700
tgggtgttcg gggcgttttt ttttgtcgg gatttcgatt tcttggcggg gtcgaatttt      2760
tttkttttag gtagggcggt ttcggggta gtcggagatt cgktggatt tatcggggcg      2820
tttttggtat ttcgtgcgga agttttgggg gtagtggttt cggtttcgga agttttttgt      2880
acggtttttt cgtgttaagg ttgtatggtt ggcgtttttt gttttcgaa agaagaattc      2940
gtttaggaa aaggtcgtaa gaggaagagt tagtagtagt tgttggaaat taagtattat      3000
tggcgggtat ataagagttt gcgattcgaa ggggaatttt aggttgggaa gtcgttggga      3060
gttacgttta tgtcgcgaag aggttggtcg cggttttttt tgaggttata aaagtttcga      3120
agttttaat ttttaggta attcgtgttt ttgttttaag aagatgaggt agggtcgggc       3180
gcggtggttt acgtttgtaa ttttagtatt cgagaggtcg aggtaggcgg gtcgtttgag      3240
tttaggagtt tgagattagt ttgggtaatt tagtaagatt tggttttttt tataattaaa      3300
tatatgtgtg tgtgtgtgtt gtttgggtat attgatttac gtttgtaatt ttagtaattt      3360
gggagatcga ggtgggcgga ttatttgagg ttaggagttt aagattagtt tggttaataa      3420
ggcgaaagaa atttcgtttt tattaaaaaa tataaatatt agttaggcgt ggtggcgggt      3480
atttgtaatt ttagttattc gggaggttga ggttggagaa ttatttgaat cgggaggcg      3540
gaggttgtag tgagttgaga cgtgttattt tattttagtt tgggcgatag agcgagattt      3600
tgttttaaaa aagaaaaaga ggttaggcgt ggtggtttac gtttgtaatt ttagtagttt      3660
gggaggtcga ggcgggcgga ttacgaggtt aagatatcga gatttttttg gttaatatgg      3720
tgaaatttcg tttttattaa aaatataaaa aattagtcgg gtttggtggc gtttgtagtt      3780
```

```
ttatttattc gggaggtcga gatagagaat tgtttgaatt cgggaggtag aggttgtagt    3840
gagtcgagat cgcgttattg tattttagtt tgggtaatag aaaaagagtt tattataaaa    3900
taaaataaaa taaaataaaa atattgatag agaaattttt ttttttttaag tgaaagtttt   3960 tttaaattta attttggttt gagttagggg ggcgtaattt                          4000

<210> SEQ ID NO 6
<211> LENGTH: 4000
<212> TYPE: DNA
<213> ORGANISM: Homo sapiens

<400> SEQUENCE: 6
attagtttgg ttaatatggt gaaattttgt ttttattaaa aatataaaaa ttagttgggt      60
atggtggtgg gtgtttgtag ttttagttat tgggaggtt gaggtaggag aatggtgtga     120
atttagtagg tagggtttgt agtgagttga gattgtgtta ttgtatttta gtttgggtga    180
tagagtgaga ttttgtttta aatatatata tatatatata tatatatata tataaagtgg    240
ttttgaatgg agattgtttt ttgaatgttt tgtttttta ttttaattag taattttttt    300 tttttttgg atttgttata tatagtaatt gaattgaatt gatatttata taataagaat    360
tatgtttaat tagagatata tttgatgttg aaaagtaaat tagttaatta aaaagaatta    420
tgtttaagat atagtttggg ttgggtgttg tggtttaagt ttgtaatttt agtatttagg    480
gaggttgagg taggtggatt atttgaggtt agagtttgag attagtttgg ttaatatggt    540
gaaattttgt ttttattaaa aatatataaa ttagttggga gtggggtag gtatttgtaa     600 tttttgttat ttggaaggtt gaagtwggag aattgtttga atttggaagt tggaggttgt    660
agtgaaattt agatggtatt attgtattat agtttgggta ataagagtga aattttatta    720 aaaaagaag aagaagaaa gaaagaaag aagaataaaa ataagagag agagagagag       780 aggaagagag ggagggagga aaagagagag atagagagat agagagaaga gaagagaaga    840 gaaaaagaa gagaaagaa gttgggtgtg gtggtttatg tttgtaatt tagtatttg        900 ggaggttgag gttggtagat tatttgaggt tgggagtttt agattagttt gattaatatg    960
gagaaagttt gttttatta aaaatataaa attagttagg gtggaggttt atgtttgtaa    1020
ttttatttat ttaggaggtt gagatagggag aattgtttga atttgggagg tggaggttga   1080
ggtgagttga gattgtgtta ttgtatttta gtttgggtaa taagagtgaa attttgtttt    1140
aaaaaaaaaa aaaagaaaga agaaagaaaa agaaaaaga ataaattttt tgttgggta     1200 agaaatatgt tttagttagg aatttgtttt taaatttta atttatatag gaatgattaa    1260
tgatttaatt atttataagt aaatggagtt gtgtaatata tatgttgaag taattatatg    1320
gaatgtgtat ttgaaagtg ttttagtatt tgtaggagat attttttatt gtttgtttaa    1380
tattatattg taagtttttt atgattttg tgtaagaaat tggggataga tggttgggtg    1440
tggtagttsa tgtttgtaat tttagtattt tgagaggttg agatgagtga attaagaggt    1500
taggagattg agattatttt ggttaatatg gtgaaatatt gtttttatta aaatataaaa    1560
aaaaattagt tgggtatggt ggtgggtgtt tgtagtttta gttatttggg aagttgaggt    1620
aggagaatgg tgtgaatttg ggaggtggag tttgtagtga gttgagatag tgttattgta    1680
ttttagttgg gggatgtag tgagattttg ttttaaaaaa aaaaaaaag aaaagaaaag      1740 aaaaagaaa aaaagaaat tggggttaga tgggatagta ggagagggggg tagggaggaa    1800 gaggggagga gaaattgaag atttttttt ttatggagta agaggttttt tttataggaa    1860
aaagtttatg tggaattttt aatagattat tttaaattat ttaagttaat atttgatttg    1920
```

-continued

| | |
|---|---|
| ggattttagg tttatattat taaatattgt tttgttatgg aaatttgata tatgttggtt | 1980 |
| tgtatgaatg aatttatata tttgaatttt tttgggagta gtgttttgaa attagttagt | 2040 |
| aattagtatt ggttggttgt ttgattgttg gatgtgtaga tgaataaatg aatggtttgt | 2100 |
| tgttttattt agattaggtt attgaaaaat atgtaaaagt ttaagttatt tttgaaggga | 2160 |
| agtgaggggt gtgatttggg gaaggtaggg attgtggatt gtggaaggtt gagtagtggg | 2220 |
| gtttggtggg agggtgttaa gtagtttatt tttatgtgtt tatagtagtt tttggtgttt | 2280 |
| agtagtttga tgttttgaa tgtggagttg tattttagtt tgagtagtag gtggtttata | 2340 |
| attttttta ttattttgt tgttgtggag atattattgt ggttgagttt taattttttt | 2400 |
| aaaattgttt ggagttttga ggttttaggt gttgtatttt tttgtatgag aatgggggtt | 2460 |
| gagattggta ggtggggtt gggtatgttt tagggtttgg gtggrggttt tggttttgtg | 2520 |
| gagtagtgtg tgtttttttg gtggtaagaa ttagttttgg aaagagttgg tttttgagtt | 2580 |
| gtaggaggtt ttagttttttt tgttttaggg gtgttggtgg tgttagatgg ttgtgtgttt | 2640 |
| tgggtgtgtt gaggggtttt tttggtgtgg gttttagttg tgtggatggg tggtttttt | 2700 |
| tgggtgtttg gggtgttttt ttttttgttgg gattttgatt tttggtggg gttgaatttt | 2760 |
| tttkttttag gtagggtggt tttgggggta gttggagatt tgktgggatt tattggggtg | 2820 |
| tttttggtat tttgtgtgga agttttgggg gtagtggttt tggttttgga agtttttgt | 2880 |
| atggttttt tgtgttaagg ttgtatggtt ggtgttttt gtttttgaa agaagaattt | 2940 |
| gttttaggaa aaggttgtaa gaggaagagt tagtagtagt tgttggaaat taagtattat | 3000 |
| tggtgggtat ataagagttt gtgatttgaa ggggaatttt aggttgggaa gttgttggga | 3060 |
| gttatgttta tgttgtgaag aggttggttg tggttttttt tgaggttata aaagttttga | 3120 |
| agttttaat tttttaggta atttgtgttt ttgttttaag aagatgaggt agggttgggt | 3180 |
| gtggtggttt atgtttgtaa ttttagtatt tgagaggttg aggtaggtgg gttgtttgag | 3240 |
| tttaggagtt tgagattagt ttgggtaatt tagtaagatt tggttttttt tataattaaa | 3300 |
| tatatgtgtg tgtgtgtgtt gtttgggtat attgatttat gtttgtaatt ttagtaattt | 3360 |
| gggagattga ggtgggtgga ttatttgagg ttaggagttt aagattagtt tggttaataa | 3420 |
| ggtgaaagaa attttgtttt tattaaaaaa tataaatatt agttaggtgt ggtggtgggt | 3480 |
| atttgtaatt ttagttattt gggaggttga ggttggagaa ttatttgaat ttgggaggtg | 3540 |
| gaggttgtag tgagttgaga tgtgttattt tatttagtt tgggtgatag agtgagattt | 3600 |
| tgttttaaaa aagaaaaaga ggttaggtgt ggtggtttat gtttgtaatt ttagtagttt | 3660 |
| gggaggttga ggtgggtgga ttatgaggtt aagatattga gattttttg gttaatatgg | 3720 |
| tgaaattttg ttttttattaa aaatataaaa aattagttgg gttggtggt gtttgtagtt | 3780 |
| ttatttattt gggaggttga gatagagaat tgtttgaatt tgggaggtag aggttgtagt | 3840 |
| gagttgagat tgtgttattg tattttagtt tgggtaatag aaaagagtt tattataaaa | 3900 |
| taaaataaaa taaaataaaa atattgatag agaaattttt ttttttaag tgaaagtttt | 3960 |
| tttaaatttta attttggttt gagttagggg ggtgtaattt | 4000 |

<210> SEQ ID NO 7
<211> LENGTH: 1060
<212> TYPE: DNA
<213> ORGANISM: Homo sapiens

<400> SEQUENCE: 7

| | |
|---|---|
| acttcgagac ttttgtagcc tcaggaaagg ccgcggccag cctcttcgcg gcatgggcgt | 60 |

```
ggctcccagc gacttcccag cctggggttc cccttcgggt cgcagactct tgtgtgcccg      120
ccagtagtgc ttggttttcca acagctgctg ctggctcttc ctcttgcggc cttttcctga     180
aacggattct tctttcgggg aacagaaagc gccagccatg cagccttggc acggaaaggc     240
crtgcagaga gcttccgagg ccggagccac tgccccaag gcttccgcac ggaatgccag      300
gggcgccccg atggatccca mcgagtctcc ggctgccccc gaggccgccc tgcctaaggm    360
gggaaagttc ggccccgcca graagtcggg atcccggcag aaaaagagcg ccccggacac     420
ccaggagagg ccgcccgtcc gcgcaactgg ggcccgcgcc aaaaaggccc ctcagcgcgc     480
ccaggacacg cagccgtctg acgccaccag cgccctggg gcagagggc tggagcctcc       540 tgcggctcgg gagccggctc ttttccaggc tggttcttgc cgccagaggg gcgcgcgctg    600
ctccacgaag ccaagaccyc cgccggggcc ctgggacgtg cccagccccg gcctgccggt   660
ctcggccccc attctcgtac ggagggatgc ggcgcctggg gcctcgaagc tccgggcggt   720
tttggagaag ttgaagctca gccgcgatga tatctccacg gcggcgggga tggtgaaagg    780
ggttgtggac cacctgctgc tcagactgaa gtgcgactcc gcgttcagag cgtcgggct     840 gctgaacacc gggagctact atgagcacgt gaaggtgagc tgcttggcgc cctcccgccg  900
agccccgctg ctcggccttc cgcaatccgc agtccctacc ttccccgggt cgcgcccctc    960
acttcccttc ggaagtaact tagactttttg catgtttttc ggtagcctag tctaagtaaa    1020
acgacaaacc gttcgtttat tcatctacac atccaacgat                           1060

<210> SEQ ID NO 8
<211> LENGTH: 1060
<212> TYPE: DNA
<213> ORGANISM: Homo sapiens

<400> SEQUENCE: 8
atttcgagat ttttgtagtt ttaggaaagg tcgcggttag ttttttcgcg gtatgggcgt     60 ggttttttagc gatttttttag tttggggttt ttttttcggggt cgtagatttt tgtgtgttcg   120
ttagtagtgt ttggttttta atagttgttg ttggtttttt tttttgcggt ttttttttga    180
aacggatttt ttttttcgggg aatagaaagc gttagttatg tagttttggt acggaaaggt     240
trtgtagaga gttttcgagg tcggagttat tgttttaag gttttcgtac ggaatgttag     300
gggcgtttcg atggatttta mcgagttttc ggttgtttc gaggtcgttt tgtttaaggm     360
gggaaagttc ggtttcgtta graagtcggg atttcggtag aaaaagagcg tttcggatat    420
ttaggagagg tcgttcgttc gcgtaattgg ggttcgcgtt aaaaaggttt tttagcgcgt    480
ttaggatacg tagtcgtttg acgttattag cgttttttggg gtagagggt tggagttttt   540 tgcggttcgg gagtcggttt ttttttagggt tggttttttgt cgttagaggg gcgcgcgttg   600
ttttacgaag ttaagattct cgttcggggtt ttgggacgtg tttagttttcg gtttgtcggt    660 ttcggtttttt attttcgtac ggagggatgc ggcgtttggg gttcgaagt ttcgggcggt    720 tttggagaag ttgaagttta gtcgcgatga tattttacg gcggcgggga tggtgaaagg    780
ggttgtggat tatttgttgt ttagattgaa gtgcgatttc gcgtttagag cgtcgggtt     840 gttgaatatc gggagttatt atgagtacgt gaaggtgagt tgtttggcgt ttttttcgtcg  900 agtttcgttg ttcggttttt cgtaattcgt agtttttatt tttttcgggt cgcgttttttt   960 attttttttc ggaagtaatt tagatttttg tatgtttttc ggtagtttag tttaagtaaa   1020
acgataaatc gttcgtttat ttatttatat atttaacgat                          1060

<210> SEQ ID NO 9
```

<211> LENGTH: 1060
<212> TYPE: DNA
<213> ORGANISM: Homo sapiens

<400> SEQUENCE: 9

```
attttgagat ttttgtagtt ttaggaaagg ttgtggttag ttttttttgtg gtatgggtgt      60
ggttttagt gattttttag tttggggttt ttttttgggt tgtagatttt tgtgtgtttg       120
ttagtagtgt ttggttttta atagttgttg ttggttttttt tttttgtggt ttttttttga    180
aatggatttt ttttttgggg aatagaaagt gttagttatg tagttttggt atggaaaggt      240
trtgtagaga gttttttgagg ttggagttat tgtttttaag gtttttgtat ggaatgttag    300
gggtgttttg atggatttta mtgagttttt ggttgttttt gaggttgttt tgtttaaggm     360
gggaaagttt ggttttgtta graagttggg attttggtag aaaagagtg ttttggatat      420
ttaggagagg ttgtttgttt gtgtaattgg ggtttgtgtt aaaaaggttt tttagtgtgt      480
ttaggatatg tagttgtttg atgttattag tgttttttggg gtagaggggt tggagttttt    540
tgtggtttgg gagttggttt ttttttagggt tggttttttgt tgttagaggg gtgtgtgttg    600
ttttatgaag ttaagatttt tgtttggggtt ttgggatgtg tttagtttttg gtttgttggt   660
tttggttttt attttttgtat ggagggatgt ggtgtttggg gttttgaagt tttgggtggt    720
tttggagaag ttgaagtttta gttgtgatga tattttttatg gtggtgggga tggtgaaagg  780
ggttgtggat tattttgttgt ttagattgaa gtgtgatttt tgtttagag gtgttgggtt   840
gttgaatatt gggagttatt atgagtatgt gaaggtgagt tgtttggtgt tttttttgttg   900
agttttgttg tttggttttt tgtaatttgt agttttttatt ttttttgggt tgtgttttttt    960
atttttttt ggaagtaatt tagatttttg tatgttttttt ggtagtttag tttaagtaaa    1020
atgataaatt gtttgtttat ttatttatat atttaatgat                          1060
```

<210> SEQ ID NO 10
<211> LENGTH: 1060
<212> TYPE: DNA
<213> ORGANISM: Homo sapiens

<400> SEQUENCE: 10

```
atcgttggat gtgtagatga ataaacgaac ggtttgtcgt tttacttaga ctaggctacc      60
gaaaaacatg caaaagtcta agttacttcc gaagggaagt gaggggcgcg acccggggaa   120
ggtagggact gcggattgcg gaaggccgag cagcggggct cggcgggagg gcgccaagca    180
gctcaccttc acgtgctcat agtagctccc ggtgttcagc agcccgacgc ctctgaacgc   240
ggagtcgcac ttcagtctga gcagcaggtg gtccacaacc cctttcacca tccccgccgc   300
cgtggagata tcatcgcggc tgagcttcaa cttctccaaa accgcccgga gcttcgaggc   360
cccaggcgcc gcatccctcc gtacgagaat gggggccgag accggcaggc cggggctggg  420
cacgtcccag ggcccgggcg grggtcttgg cttcgtggag cagcgcgcgc ccctctggcg   480
gcaagaacca gccctggaaa gagccggctc ccgagccgca ggaggctcca gccctctgc    540
cccagggcg ctggtggcgt cagacggctg cgtgtcctgg gcgcgctgag gggccttttt     600
ggcgcgggcc ccagttgcgc ggacgggcgg cctctcctgg gtgtccgggg cgctctttttt  660
ctgccgggat cccgacttyc tggcggggcc gaactttccc kccttaggca gggcggcctc   720
ggggggcagcc ggagactcgk tgggatccat cggggcgccc ctggcattcc gtgcggaagc  780
cttggggggca gtggctccgg cctcggaagc tctctgcayg gcctttccgt gcaaggctg    840
catggctggc gctttctgtt ccccgaaaga agaatccgtt tcaggaaaag gccgcaagag   900
```

-continued

| | |
|---|---|
| gaagagccag cagcagctgt tggaaaccaa gcactactgg cgggcacaca agagtctgcg | 960 |
| acccgaaggg gaaccccagg ctgggaagtc gctgggagcc acgcccatgc cgcgaagagg | 1020 |
| ctggccgcgg cctttcctga ggctacaaaa gtctcgaagt | 1060 |

<210> SEQ ID NO 11
<211> LENGTH: 1060
<212> TYPE: DNA
<213> ORGANISM: Homo sapiens

<400> SEQUENCE: 11

| | |
|---|---|
| atcgttggat gtgtagatga ataaacgaac ggtttgtcgt tttatttaga ttaggttatc | 60 |
| gaaaaatatg taaaagttta agttattttc gaagggaagt gaggggcgcg attcggggaa | 120 |
| ggtagggatt gcggattgcg gaaggtcgag tagcggggtt cggcgggagg gcgttaagta | 180 |
| gtttattttt acgtgtttat agtagttttc ggtgtttagt agttcgacgt ttttgaacgc | 240 |
| ggagtcgtat tttagtttga gtagtaggtg gtttataatt tttttatta ttttcgtcgt | 300 |
| cgtggagata ttatcgcggt tgagttttaa ttttttttaaa atcgttcgga gtttcgaggt | 360 |
| tttaggcgtc gtattttttc gtacgagaat ggggtcgag atcggtaggt cggggttggg | 420 |
| tacgttttag ggttcgggcg grggttttgg tttcgtggag tagcgcgcgt ttttttggcg | 480 |
| gtaagaatta gttttggaaa gagtcggttt tcgagtcgta ggaggtttta gtttttttgt | 540 |
| tttaggggcg ttggtggcgt tagacggttg cgtgttttgg gcgcgttgag gggttttttt | 600 |
| ggcgcgggtt ttagttgcgc ggacgggcgg tttttttttgg gtgttcgggg cgttttttt | 660 |
| ttgtcgggat ttcgatttct tggcggggtc gaattttttt kttttaggta gggcggtttc | 720 |
| gggggtagtc ggagattcgk tgggatttat cggggcgttt ttggtatttc gtgcggaagt | 780 |
| tttgggggta gtggtttcgg tttcggaagt tttttgtacg gttttttcgt gttaaggttg | 840 |
| tatggttggc gttttttgtt tttcgaaaga agaattcgtt ttaggaaaag gtcgtaagag | 900 |
| gaagagttag tagtagttgt tggaaattaa gtattattgg cgggtatata agagtttgcg | 960 |
| attcgaaggg gaattttagg ttgggaagtc gttgggagtt acgtttatgt cgcgaagagg | 1020 |
| ttggtcgcgg tttttttttga ggttataaaa gtttcgaagt | 1060 |

<210> SEQ ID NO 12
<211> LENGTH: 1060
<212> TYPE: DNA
<213> ORGANISM: Homo sapiens

<400> SEQUENCE: 12

| | |
|---|---|
| attgttggat gtgtagatga ataaatgaat ggtttgttgt tttatttaga ttaggttatt | 60 |
| gaaaaatatg taaaagttta agttattttt gaagggaagt gaggggtgtg atttggggaa | 120 |
| ggtagggatt gtggattgtg aaggttgag tagtggggtt tggtgggagg gtgttaagta | 180 |
| gtttattttt atgtgtttat agtagttttt ggtgtttagt agtttgatgt ttttgaatgt | 240 |
| ggagttgtat tttagtttga gtagtaggtg gtttataatt tttttatta tttttgttgt | 300 |
| tgtggagata ttattgtggt tgagttttaa ttttttttaaa attgtttgga gttttgaggt | 360 |
| tttaggtgtt gtattttttt gtatgagaat ggggttgag attggtaggt tggggttggg | 420 |
| tatgttttag ggtttgggtg grggttttgg ttttgtggag tagtgtgtgt tttttggtg | 480 |
| gtaagaatta gttttggaaa gagttggttt ttgagttgta ggaggtttta gtttttttgt | 540 |
| tttaggggtg ttggtggtgt tagatggttg tgtgttttgg gtgtgttgag gggttttttt | 600 |
| ggtgtgggtt ttagttgtgt ggatgggtgg tttttttttgg gtgtttgggg tgttttttt | 660 |

-continued

```
ttgttgggat tttgattttt tggtgggtt gaatttttt kttttaggta gggtggtttt      720 ggggtagtt ggagatttgk tgggatttat tggggtgttt ttggtatttt gtgtggaagt     780 tttggggta gtggttttgg ttttggaagt ttttgtatg gtttttttgt gttaaggttg      840
tatggttggt gtttttgtt ttttgaaaga agaatttgtt ttaggaaaag gttgtaagag     900
gaagagttag tagtagttgt tggaaattaa gtattattgg tgggtatata agagtttgtg   960
atttgaaggg gaattttagg ttgggaagtt gttgggagtt atgtttatgt tgtgaagagg   1020
ttggttgtgg ttttttttga ggttataaaa gttttgaagt                          1060

<210> SEQ ID NO 13
<211> LENGTH: 130
<212> TYPE: DNA
<213> ORGANISM: Homo sapiens

<400> SEQUENCE: 13
gagtctccgg ctgcccccga ggccgccctg cctaaggmgg gaaagttcgg ccccgccagr   60
aagtcgggat cccggcagaa aaagagcgcc ccggacaccc aggagaggcc gcccgtccgc   120
gcaactgggg                                                          130

<210> SEQ ID NO 14
<211> LENGTH: 130
<212> TYPE: DNA
<213> ORGANISM: Homo sapiens

<400> SEQUENCE: 14
gagttttcgg ttgttttcga ggtcgttttg tttaaggmgg gaaagttcgg tttcgttagr   60
aagtcgggat ttcggtagaa aaagagcgtt tcggatattt aggagaggtc gttcgttcgc   120
gtaattgggg                                                          130

<210> SEQ ID NO 15
<211> LENGTH: 130
<212> TYPE: DNA
<213> ORGANISM: Homo sapiens

<400> SEQUENCE: 15
gagtttttgg ttgtttttga ggttgttttg tttaaggmgg gaaagtttgg ttttgttagr   60
aagttgggat tttggtagaa aaagagtgtt tggatattt aggagaggtt gtttgtttgt    120
gtaattgggg                                                          130

<210> SEQ ID NO 16
<211> LENGTH: 130
<212> TYPE: DNA
<213> ORGANISM: Homo sapiens

<400> SEQUENCE: 16
ccccagttgc gcggacgggc ggcctctcct gggtgtccgg ggcgctcttt ttctgccggg    60
atcccgactt yctggcgggg ccgaactttc cckccttagg cagggcggcc tcggggggcag  120 ccggagactc                                                          130

<210> SEQ ID NO 17
<211> LENGTH: 130
<212> TYPE: DNA
<213> ORGANISM: Homo sapiens

<400> SEQUENCE: 17
ttttagttgc gcggacgggc ggttttttt gggtgttcgg ggcgtttttt ttttgtcggg    60
```

```
atttcgattt cttggcgggg tcgaattttt ttkttttagg tagggcggtt tcggggtag      120 tcggagattc                                                            130

<210> SEQ ID NO 18
<211> LENGTH: 130
<212> TYPE: DNA
<213> ORGANISM: Homo sapiens

<400> SEQUENCE: 18
ttttagttgt gtggatgggt ggttttttt gggtgtttgg ggtgttttt ttttgttggg       60 attttgattt tttggtgggg ttgaattttt ttkttttagg tagggtggtt ttgggggtag    120
ttggagattt                                                            130

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttggggttt tttttcgggt cgt                                             23

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaaacgcccc taacattccg tacga                                           25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtagagagt tttcgaggtc gg                                              22

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaacgcccc taacattccg tacga                                           25

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
```

```
tgtagagagt tttcgaggtc gg                                              22
```

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
acaaaacgac ctcgaaaaca accga                                           25
```

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gagttattgt ttttaaggtt ttcgtacgg                                       29
```

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
acaaaacgac ctcgaaaaca accga                                           25
```

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
gagttattgt ttttaaggtt ttcgtacgg                                       29
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
ccccaattac gcgaacgaac ga                                              22
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
acggaatgtt aggggcgttt cg                                              22
```

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccccaattac gcgaacgaac ga                                              22

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gagttttcgg ttgttttcga ggtcgt                                          26

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccccaattac gcgaacgaac ga                                              22

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gatttcggta gaaaagagc gtttcgg                                          27

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccccaattac gcgaacgaac ga                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acggaatgtt aggggcgttt cg                                              22

```
<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caaacgacta cgtatcctaa acgcgct                                         27

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gagttttcgg ttgttttcga ggtcgt                                          26

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caaacgacta cgtatcctaa acgcgct                                         27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gatttcggta gaaaagagc gtttcgg                                          27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caaacgacta cgtatcctaa acgcgct                                         27

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aggagaggtc gttcgttcgc gt                                              22

<210> SEQ ID NO 42
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caaacgacta cgtatcctaa acgcgct                                            27

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gagttttcgg ttgttttcga ggtcgt                                             26

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaacgctaat aacgtcaaac gactacgt                                           28

<210> SEQ ID NO 51
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatttcggta gaaaagagc gtttcgg                                          27

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaacgctaat aacgtcaaac gactacgt                                        28

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aggagaggtc gttcgttcgc gt                                              22

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaacgctaat aacgtcaaac gactacgt                                        28

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aggagaggtc gttcgttcgc gt                                              22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgtcccaaa acccgaacga ga                                              22

<210> SEQ ID NO 57
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 57
tagcgcgttt aggatacgta gtcgt                                            25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acgtcccaaa acccgaacga ga                                               22

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tttttgcggt tcgggagtcg g                                                21

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgtcccaaa acccgaacga ga                                               22

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tagcgcgttt aggatacgta gtcgt                                            25

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
taaaaaccga aaccgacaaa ccga                                             24

<210> SEQ ID NO 63
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 63
tttttgcggt tcgggagtcg g                                              21

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
taaaaaccga aaccgacaaa ccga                                           24

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtcgttagag gggcgcgcgt                                                20

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
taaaaaccga aaccgacaaa ccga                                           24

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tagcgcgttt aggatacgta gtcgt                                          25

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acgccgcatc cctccgtacg a                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 69
tttttgcggt cgggagtcg g                                         21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acgccgcatc cctccgtacg a                                        21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtcgttagag gggcgcgcgt                                          20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgccgcatc cctccgtacg a                                        21

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ttacgaagtt aagattctcg ttcgg                                    25

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acgccgcatc cctccgtacg a                                        21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
```

```
tttttgcggt tcgggagtcg g                                              21
```

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
ccaaaaccgc ccgaaacttc ga                                             22
```

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
gtcgttagag gggcgcgcgt                                                20
```

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

```
ccaaaaccgc ccgaaacttc ga                                             22
```

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
ttacgaagtt aagattctcg ttcgg                                          25
```

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
ccaaaaccgc ccgaaacttc ga                                             22
```

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
ggacgtgttt agtttcggtt tgtcgg                                         26
```

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccaaaaccgc ccgaaacttc ga                                              22

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtcgttagag gggcgcgcgt                                                 20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccgccgtaaa aatatcatcg cga                                             23

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttacgaagtt aagattctcg ttcgg                                           25

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccgccgtaaa aatatcatcg cga                                             23

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggacgtgttt agtttcggtt tgtcgg                                          26

```
<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccgccgtaaa aatatcatcg cga                                            23

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtcggtttcg gtttttattt tcgtacgg                                       28

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccgccgtaaa aatatcatcg cga                                            23

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ttcgtacgga gggatgcggc gt                                             22

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccgccgtaaa aatatcatcg cga                                            23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gtcgttagag gggcgcgcgt                                                20

<210> SEQ ID NO 94
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
caccatcccc gccgccgt                                               18

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ttacgaagtt aagattctcg ttcgg                                       25

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
caccatcccc gccgccgt                                               18

<210> SEQ ID NO 97
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggacgtgttt agtttcggtt tgtcgg                                      26

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
caccatcccc gccgccgt                                               18

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gtcggtttcg gtttttattt tcgtacgg                                    28

<210> SEQ ID NO 100
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 100
caccatcccc gccgccgt                                                      18

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ttcgtacgga gggatgcggc gt                                                 22

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
caccatcccc gccgccgt                                                      18

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gggtttcgaa gtttcgggcg g                                                  21

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
caccatcccc gccgccgt                                                      18

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggacgtgttt agtttcggtt tgtcgg                                             26

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 106
acccgacgcc tctaaacgcg a                                              21

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gtcggtttcg gtttttattt tcgtacgg                                       28

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acccgacgcc tctaaacgcg a                                              21

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttcgtacgga gggatgcggc gt                                             22

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acccgacgcc tctaaacgcg a                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggtttcgaa gtttcgggcg g                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 112
acccgacgcc tctaaacgcg a                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gggtttcgaa gtttcgggcg g                                              21

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cgaaaaaccg aacaacgaaa ctcga                                          25

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gtttagattg aagtgcgatt tcgcgt                                         26

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cgaaaaaccg aacaacgaaa ctcga                                          25

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
atttcgcgtt tagaggcgtc gg                                             22

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

```
cgaaaaaccg aacaacgaaa ctcga                                          25
```

<210> SEQ ID NO 119
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

```
gtttagattg aagtgcgatt tcgcgt                                         26
```

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
cgaattacga aaaccgaac aacga                                           25
```

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
atttcgcgtt tagaggcgtc gg                                             22
```

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
cgaattacga aaaccgaac aacga                                           25
```

<210> SEQ ID NO 123
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gtttagattg aagtgcgatt tcgcgt                                         26
```

<210> SEQ ID NO 124
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

```
cttccgaaaa aaataaaaa acgcgacccg a                                    31
```

```
<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
atttcgcgtt tagaggcgtc gg                                              22

<210> SEQ ID NO 126
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cttccgaaaa aaaataaaaa acgcgacccg a                                    31

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gagttgtttg gcgttttttc gtcga                                           25

<210> SEQ ID NO 128
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cttccgaaaa aaaataaaaa acgcgacccg a                                    31

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
atttcgcgtt tagaggcgtc gg                                              22

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
atatataaat aaataaacga acgatttatc gt                                   32

<210> SEQ ID NO 131
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gagttgtttg gcgttttttc gtcga                                            25

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
atatataaat aaataaacga acgatttatc gt                                    32

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tttttcgtcg agtttcgttg ttcgg                                            25

<210> SEQ ID NO 134
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
atatataaat aaataaacga acgatttatc gt                                    32

<210> SEQ ID NO 135
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tttcgttgtt cggttttttcg taattcgt                                        28

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
atatataaat aaataaacga acgatttatc gt                                    32

<210> SEQ ID NO 137
<211> LENGTH: 28
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 137
cgtagttttt attttttcg ggtcgcgt                                      28

<210> SEQ ID NO 138
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
atatataaat aaataaacga acgatttatc gt                                32

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ggattgtttg gagagttaga aat                                          23

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
actccaaccc ctctacccca aa                                           22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ttggggyaga ggggttggag tt                                           22

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tcaataccra ttaattatct a                                            21

<210> SEQ ID NO 143
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 143
craaccctaa aacrtaccca a                                              21

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
aaattygata tatgtyggtt tgt                                            23

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tccraaaccr aaaccacta                                                 19

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ttttygtayg agaatggggg t                                              21

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 147

His His His His His His
1               5

<210> SEQ ID NO 148
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
caagcagctc accttcacgt gctcatagta gctcccggtg ttcag                    45

<210> SEQ ID NO 149
<211> LENGTH: 45
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 149
ggtccacaac ccctttcacc atccccgccg ccgtggagat atcat     45

<210> SEQ ID NO 150
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
atccctccgt acgagaatgg gggccgagac cggcaggccg gggct     45

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ggattgcctg gagagttaga aac     23

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cagacaacca accggtactg a     21

<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gagtctccgg ctgcccccga ggccgc     26

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ccgcccgtcc gcgcaactgg gg     22